United States Patent
Schmitt et al.

(10) Patent No.: US 11,332,784 B2
(45) Date of Patent: May 17, 2022

(54) ADAPTERS, METHODS, AND COMPOSITIONS FOR DUPLEX SEQUENCING

(71) Applicant: TwinStrand Biosciences, Inc., Seattle, WA (US)

(72) Inventors: Michael W. Schmitt, Seattle, WA (US); Lawrence A. Loeb, Bellevue, WA (US); Jesse J. Salk, Seattle, WA (US)

(73) Assignee: TwinStrand Biosciences, Inc., Seattle, WA (US)

( * ) Notice: Subject to any disclaimer, the term of this patent is extended or adjusted under 35 U.S.C. 154(b) by 381 days.

(21) Appl. No.: 15/372,761

(22) Filed: Dec. 8, 2016

(65) Prior Publication Data
US 2017/0211140 A1    Jul. 27, 2017

Related U.S. Application Data

(60) Provisional application No. 62/264,822, filed on Dec. 8, 2015, provisional application No. 62/281,917, filed on Jan. 22, 2016.

(51) Int. Cl.
*C12Q 1/68* (2018.01)
*C12Q 1/6869* (2018.01)
*C12Q 1/6855* (2018.01)

(52) U.S. Cl.
CPC ......... *C12Q 1/6869* (2013.01); *C12Q 1/6855* (2013.01)

(58) Field of Classification Search
None
See application file for complete search history.

(56) References Cited

U.S. PATENT DOCUMENTS

| | | | |
|---|---|---|---|
| 5,308,751 A | 5/1994 | Ohkawa et al. | |
| 6,251,610 B1 | 6/2001 | Gupte | |
| 6,582,908 B2 | 6/2003 | Fodor et al. | |
| 6,958,225 B2 | 10/2005 | Dong | |
| 7,214,490 B2 | 5/2007 | Su et al. | |
| 7,267,966 B2 | 9/2007 | Dong et al. | |
| 7,297,778 B2 | 11/2007 | Matsuzaki et al. | |
| 7,406,385 B2 | 7/2008 | Sorenson | |
| 7,452,699 B2 | 11/2008 | Makrigiorgos et al. | |
| 7,459,273 B2 | 12/2008 | Jones et al. | |
| 7,537,897 B2 | 5/2009 | Brenner et al. | |
| 7,741,463 B2 | 6/2010 | Gormley et al. | |
| 8,029,993 B2 | 10/2011 | Mikawa | |
| 8,148,068 B2 | 4/2012 | Brenner et al. | |
| 8,153,375 B2 | 4/2012 | Travers et al. | |
| 8,318,434 B2 | 11/2012 | Cuppens | |
| 8,715,967 B2 | 5/2014 | Casbon et al. | |
| 8,741,606 B2 | 6/2014 | Casbon | |
| 9,080,210 B2 | 7/2015 | Van Eijk et al. | |
| 9,085,798 B2 | 7/2015 | Chee | |
| 9,249,460 B2 | 2/2016 | Pushkarev et al. | |
| 9,260,753 B2 | 2/2016 | Xie et al. | |
| 9,476,095 B2 | 10/2016 | Vogelstein et al. | |
| 9,487,829 B2 | 11/2016 | Vogelstein et al. | |
| 9,598,731 B2 | 3/2017 | Talasaz | |
| 9,745,627 B2 | 8/2017 | van Eijk et al. | |
| 9,752,188 B2 | 9/2017 | Schmitt et al. | |
| 9,783,847 B2 | 10/2017 | Chee | |
| 9,834,822 B2 | 12/2017 | Talasaz | |
| 9,840,743 B2 | 12/2017 | Talasaz | |
| 9,862,995 B2 | 1/2018 | Patel | |
| 9,898,577 B2 | 2/2018 | Van Eijk et al. | |
| 9,902,992 B2 | 2/2018 | Talasaz et al. | |
| 9,920,366 B2 | 3/2018 | Eltoukhy et al. | |
| 9,926,566 B2 * | 3/2018 | Ochsner ............... | C12N 15/115 |
| 9,970,054 B2 | 5/2018 | Otwinowski et al. | |
| 10,000,800 B2 | 6/2018 | Chee | |
| 10,011,871 B2 * | 7/2018 | Bielas ................... | C12N 15/81 |
| 10,023,907 B2 | 7/2018 | Van Eijk et al. | |
| 10,041,127 B2 | 8/2018 | Talasaz | |
| 10,119,165 B2 | 11/2018 | Chee | |
| 10,202,646 B2 | 2/2019 | Fodor et al. | |
| 10,266,883 B2 | 4/2019 | Chee | |
| 10,266,884 B2 | 4/2019 | Chee | |
| 10,287,630 B2 | 5/2019 | Xie et al. | |
| 10,287,631 B2 | 5/2019 | Salk et al. | |
| 10,370,713 B2 | 8/2019 | Salk et al. | |
| 10,385,393 B2 | 8/2019 | Salk et al. | |
| 10,501,793 B2 | 12/2019 | Chee | |
| 10,570,451 B2 | 2/2020 | Salk et al. | |
| 10,689,700 B2 | 6/2020 | Salk et al. | |

(Continued)

FOREIGN PATENT DOCUMENTS

| | | |
|---|---|---|
| CN | 102877136 B | 3/2014 |
| GB | 2533882 B | 10/2016 |

(Continued)

OTHER PUBLICATIONS

Ameur, A, et al. "UltraDeep Sequencing of Mouse Mitochondrial DNA: Mutational Patterns and Their Origins." PLoS Genet. (2011); 7.3: e1 002028.

Bainbridge, M.N., et al. "Whole exome capture in solution with 3 Gbp of data." Genome Biol. (2010); 11.6: R62:1-8.

Boyd, S.O., et al. "Measurement and Clinical Monitoring of Human Lymphocyte Clonality by Massively Parallel V-D-J Pyrosequencing." Science Translational Medicine (2009); 1.12: 12ra23-12ra23.

Campbell, P.J., et al. "Subclonal phylogenetic structures in cancer revealed by ultra-deep sequencing." Proc Natl Acad Sci USA (2008); 105.35: 13081-13086.

(Continued)

*Primary Examiner* — Suryaprabha Chunduru

(74) *Attorney, Agent, or Firm* — Sterne, Kessler, Goldstein & Fox P.L.L.C.

(57) ABSTRACT

Disclosed herein are adapter nucleic acid sequences, double-stranded complexed nucleic acids, compositions, and methods for sequencing a double-stranded target nucleic acid with applications to error correction by duplex sequencing.

40 Claims, 20 Drawing Sheets

Specification includes a Sequence Listing.

(56) References Cited

U.S. PATENT DOCUMENTS

| | | | |
|---|---|---|---|
| 10,711,304 B2 | 7/2020 | Salk et al. | |
| 10,752,951 B2 | 8/2020 | Salk et al. | |
| 10,760,127 B2 | 9/2020 | Salk et al. | |
| 10,870,882 B2 | 12/2020 | Otwinowski et al. | |
| 11,118,225 B2 | 9/2021 | Salk et al. | |
| 2003/0165923 A1 | 9/2003 | Li et al. | |
| 2004/0209299 A1 | 10/2004 | Pinter et al. | |
| 2005/0100900 A1* | 5/2005 | Kawashima | C12Q 1/6869 435/6.11 |
| 2007/0128624 A1 | 6/2007 | Gormley et al. | |
| 2007/0172839 A1 | 7/2007 | Smith et al. | |
| 2007/0172873 A1 | 7/2007 | Brenner et al. | |
| 2008/0167195 A1 | 7/2008 | Li et al. | |
| 2008/0261204 A1 | 10/2008 | Lexow | |
| 2009/0298075 A1 | 12/2009 | Travers et al. | |
| 2010/0069263 A1 | 3/2010 | Shendure | |
| 2010/0222238 A1 | 9/2010 | Smith et al. | |
| 2010/0331204 A1 | 12/2010 | Jeddeloh et al. | |
| 2011/0160078 A1 | 6/2011 | Fodor et al. | |
| 2011/0301042 A1 | 12/2011 | Steinman et al. | |
| 2012/0058468 A1 | 3/2012 | McKeown | |
| 2012/0094847 A1 | 4/2012 | Warthmann et al. | |
| 2012/0165202 A1 | 6/2012 | Porreca et al. | |
| 2012/0208724 A1* | 8/2012 | Steemers | C12Q 1/6869 506/26 |
| 2012/0220494 A1 | 8/2012 | Samuels et al. | |
| 2012/0238738 A1 | 9/2012 | Hendrickson | |
| 2012/0244525 A1 | 9/2012 | Hendrickson | |
| 2013/0079231 A1 | 3/2013 | Pushkarev et al. | |
| 2013/0142389 A1 | 6/2013 | Shimura | |
| 2013/0303461 A1 | 11/2013 | Iafrate et al. | |
| 2014/0030704 A1 | 1/2014 | Mikawa | |
| 2014/0057799 A1 | 2/2014 | Johnson et al. | |
| 2014/0134610 A1* | 5/2014 | Pham | C12N 15/1072 435/6.1 |
| 2014/0329282 A1 | 11/2014 | Nelson et al. | |
| 2014/0329698 A1 | 11/2014 | Bignell et al. | |
| 2015/0024950 A1 | 1/2015 | Bielas | |
| 2015/0044687 A1 | 2/2015 | Schmitt et al. | |
| 2015/0119261 A1 | 4/2015 | Richard | |
| 2015/0197786 A1 | 7/2015 | Osborne et al. | |
| 2016/0026758 A1 | 1/2016 | Jabara et al. | |
| 2016/0153039 A1 | 6/2016 | Amorese et al. | |
| 2016/0215333 A1 | 7/2016 | Vogelstein et al. | |
| 2016/0319345 A1 | 11/2016 | Gnerre et al. | |
| 2016/0362748 A1 | 12/2016 | Mongan et al. | |
| 2016/0362751 A1 | 12/2016 | Shin et al. | |
| 2017/0051347 A1 | 2/2017 | Vogelstein et al. | |
| 2017/0107560 A1 | 4/2017 | Peter et al. | |
| 2017/0136433 A1 | 5/2017 | Sun et al. | |
| 2017/0211140 A1 | 7/2017 | Schmitt et al. | |
| 2017/0213008 A1 | 7/2017 | Venn | |
| 2017/0247687 A1 | 8/2017 | Shendure et al. | |
| 2018/0002747 A1 | 1/2018 | Druley et al. | |
| 2018/0013598 A1 | 1/2018 | Futatsugi et al. | |
| 2018/0023135 A1 | 1/2018 | Van Eijk et al. | |
| 2018/0031588 A1 | 2/2018 | Nakajima et al. | |
| 2018/0087105 A1 | 3/2018 | Larson et al. | |
| 2018/0171415 A1 | 6/2018 | Talasaz et al. | |
| 2018/0216252 A1 | 8/2018 | Jung | |
| 2018/0251848 A1 | 9/2018 | Diehn et al. | |
| 2018/0291438 A1 | 10/2018 | Jamshidi et al. | |
| 2018/0363048 A1 | 12/2018 | Bielas | |
| 2018/0363049 A1 | 12/2018 | Bielas | |
| 2018/0363051 A1 | 12/2018 | Schmitt et al. | |
| 2018/0363052 A1 | 12/2018 | Schmitt et al. | |
| 2018/0363053 A1 | 12/2018 | Schmitt et al. | |
| 2019/0093160 A1 | 3/2019 | Schmitt et al. | |
| 2019/0093161 A1 | 3/2019 | Schmitt et al. | |
| 2019/0093162 A1 | 3/2019 | Schmitt et al. | |
| 2019/0119748 A1 | 4/2019 | Schmitt et al. | |
| 2019/0119749 A1 | 4/2019 | Schmitt et al. | |
| 2019/0271040 A1 | 9/2019 | Salk et al. | |
| 2019/0284626 A1 | 9/2019 | Salk et al. | |
| 2019/0284627 A1 | 9/2019 | Salk et al. | |
| 2019/0292597 A1 | 9/2019 | Salk et al. | |
| 2019/0323082 A1 | 10/2019 | Salk et al. | |
| 2019/0338358 A1 | 11/2019 | Salk et al. | |
| 2019/0352714 A1 | 11/2019 | Salk et al. | |
| 2020/0048701 A1 | 2/2020 | Chee | |
| 2020/0048702 A1 | 2/2020 | Chee | |
| 2020/0048703 A1 | 2/2020 | Chee | |
| 2020/0131561 A1 | 4/2020 | Kennedy et al. | |
| 2020/0318185 A1 | 10/2020 | Salk et al. | |
| 2020/0362390 A1 | 11/2020 | Salk et al. | |
| 2020/0392580 A1 | 12/2020 | Salk et al. | |
| 2021/0002711 A1 | 1/2021 | Otwinowski et al. | |
| 2021/0010065 A1 | 1/2021 | Salk et al. | |
| 2021/0371922 A1 | 2/2021 | Salk et al. | |
| 2021/0020721 A1 | 7/2021 | Otwinowski et al. | |
| 2021/0269873 A1 | 9/2021 | Salk et al. | |
| 2021/0292836 A1 | 9/2021 | Salk et al. | |
| 2021/0324470 A1 | 10/2021 | Salk et al. | |
| 2021/0355532 A1 | 11/2021 | Salk et al. | |
| 2021/0371920 A1 | 12/2021 | Salk et al. | |
| 2021/0371921 A1 | 12/2021 | Salk et al. | |
| 2021/0371923 A1 | 12/2021 | Salk et al. | |
| 2021/0371924 A1 | 12/2021 | Salk et al. | |
| 2021/0381048 A1 | 12/2021 | Salk et al. | |

FOREIGN PATENT DOCUMENTS

| | | | |
|---|---|---|---|
| WO | WO 2006/113422 A2 | 10/2006 | |
| WO | WO-2011/021102 A2 | 2/2011 | |
| WO | WO-2012/038839 A2 | 3/2012 | |
| WO | WO-2012042374 A2 | 4/2012 | |
| WO | WO-2012/061832 A1 | 5/2012 | |
| WO | WO-2012129363 A2 | 9/2012 | |
| WO | WO-2012142213 A2 | 10/2012 | |
| WO | WO-2013123442 A1 | 8/2013 | |
| WO | WO 2013/142389 A1 | 9/2013 | |
| WO | WO-2013142389 A1 * | 9/2013 | ........... C12Q 1/6869 |
| WO | WO-2013181170 A1 | 12/2013 | |
| WO | WO 2014/142850 A1 | 9/2014 | |
| WO | WO 2015/100427 A1 | 7/2015 | |
| WO | WO-2015100427 A1 * | 7/2015 | ........... C12Q 1/6886 |
| WO | WO 2015117040 A1 | 8/2015 | |
| WO | WO-2016/040901 A1 | 3/2016 | |
| WO | WO 2017037656 A1 | 3/2017 | |
| WO | WO-2017/100441 A1 | 6/2017 | |
| WO | WO-2017/127741 A1 | 7/2017 | |
| WO | WO-2018013598 A1 | 1/2018 | |
| WO | WO-2018031588 A1 | 2/2018 | |

OTHER PUBLICATIONS

Carlson, C.A., et al. "Decoding cell lineage from acquired mutations using arbitrary deep sequencing." Nat Methods (2012); 9.1: 78-80.

Casbon, J.A., et al. "A method for counting PCR template molecules with application to next-generation sequencing." Nucleic Acids Research (2011); 39:e81-e.

Cervantes, R.B., et al. "Embryonic stem cells and somatic cells differ in mutation frequency and type." Proc Natl Acad Sci USA (2002); 99: 3586-3590.

Chiu, R.W.K., et al. "Noninvasive prenatal assessment of trisomy 21 by multiplexed maternal plasma DNA sequencing: large scale validity study." BMJ (2011); 342:c7401.

De Grassi, A., et al. "Ultradeep Sequencing of a Human Ultraconserved Region Reveals Somatic and Constitutional Genomic Instability." PLoS Biol. (2010); 8:e1000275.

Ding, L., et al. "Clonal evolution in relapsed acute myeloid leukaemia revealed by whole-genome sequencing." Nature (2012); 481.7382: 506-510.

Druley, T.E., et al. "Quantification of rare allelic variants from pooled genomic DNA." Nat Methods (2009); 6: 263-265.

Ehrich, M., et al. "Noninvasive detection of fetal trisomy 21 by sequencing of DNA in maternal blood: a study in a clinical setting." Am J Obsbet Gynecol (2011); 204.3: 205e1-11.

European Application No. 13764186.6, Extended European Search Report for dated Sep. 16, 2015, 4 pages.

(56) References Cited

OTHER PUBLICATIONS

Fan, H.C., et al. "Noninvasive diagnosis of fetal aneuploidy by shotgun sequencing DNA from maternal blood." Proc Natl Acad Sci USA (2008); 105.42: 16266-16271.

Flaherty, P., et al. "Ultrasensitive detection of rare mutations using next-generation targeted resequencing." Nucleic Acids Research (2012); 40.1: e2-e.

Fordyce, S.L., et al. "High-throughput sequencing of core STR loci for forensic genetic investigations using the Roche Genome Sequencer FLX platform." BioTechniques (2011); 51.2:127-133.

Fu, G.K., et al. "Counting individual DNA molecules by the stochastic attachment of diverse labels." Proc Natl Acad Sci USA. 2011; 108.22: 9026-9031.

Garcia-Garcera, M., et al. "Fragmentation of contaminant and endogenous DNA in ancient samples determined by shotgun sequencing; prospects for human palaeogenomics." PLoS ONE (2011); 6.8: e24161.

Greaves, L.C., et al. "Quantification of mitochondrial DNA mutation load." Aging Cell (2009); 8.5: 566-572.

Haag-Liautard, C., et al. "Direct estimation of the mitochondrial DNA mutation rate in *Drosophila melanogaster*." PLoS Biol (2008); 6.8 :e204.

He, Y., et al. "Heteroplasmic mitochondrial DNA mutations in normal and tumour cells." Nature (2010); 464.7288: 610-614.

Holt and Jones. "The new paradigm of flow cell sequencing." Genome Research (2008); 18.6: 839-846.

Howell, N., et al. "How rapidly does the human mitochondrial genome evolve?" Am J Hum Genet (1996); 59.3: 501-509.

Hummelen, Ruben, et al. "Deep sequencing of the vaginal microbiota of women with HIV." PLoS One (2010); 5.8: e12078.

Hyman, R.W., et al. "The dynamics of the vaginal microbiome during infertility therapy with in vitro fertilization embryo transfer." J Assist Reorod Genet. (2012); 29.2: 105-115.

International Application No. PCT/US2013/032665, International Preliminary Report on Patentability dated Sep. 23, 2014, 10 pages.

International Application No. PCT/US2013/032665, International Search Report dated Jul. 9, 2013, 4 pages.

International Application No. PCT/US2013/032665, Written Opinion dated Jul. 9, 2013, 9 pages.

International Application No. PCT/US2016/065605, International Search Report and Written Opinion dated Mar. 3, 2017, 17 pages.

Jabara, C.B., et al. "Accurate sampling and deep sequencing of the HIV-1 protease gene using a Primer ID." Proc Natl Acad Sci USA (2011); 108.50: 20166-20171.

Jazin, E.E., et al. "Human brain contains high levels of heteroplasmy in the noncoding regions of mitochondrial DNA." Proc Natl Acad Sci USA (1996); 93.22: 12382-12387.

Kanagawa, T., "Bias and artifacts in multitemplate polymerase chain reactions (PCR)." J Biosci Bioeng. (2003); 96.4: 317-323.

Kasai, H., et al. "Formation, inhibition of formation, and repair of oxidative 8-hydroxyguanine DNA damage." Basic Life Sci (1993); 61:257-262.

Kaur, M., et al. Novel amplification of DNA in a hairpin structure: towards a radical elimination of PCR errors from amplified DNA. Nucleic Acids Res. (2003); 31.6: 26e, 1-7.

Kennedy, S.R., et al., "Somatic mutations in aging, cancer and neurodeaeneration." Mech Ageing Dev (2012); 133(4): 118-126.

Khaidakov, M., et al. "Accumulation of point mutations in mitochondrial DNA of aging mice." Mutat Res (2003); 526.1: 1-7.

Kinde, I., et al., "Detection and quantification of rare mutations with massively parallel sequencing." Proc Natl Acad Sci USA (2011); 108.23: 9530-9535.

Kircher, Martin, et al. "Double indexing overcomes inaccuracies in multiplex sequencing on the Illumina platform." Nucleic Acids Research (2012); 40.1: e3-e3.

Kivioja, T., et al. "Counting absolute numbers of molecules using unique molecular identifiers." Nat Methods (2011); 9.1: 72-74.

Kozarewa, I., et al. "Amplification free Illumina sequencing-library preparation facilitates improved mapping and assembly of (G+C)-biased genomes." Nat Methods (2009); 6.4: 291-295.

Kraytsberg, Y., et al. "Single molecule PCR in mtDNA mutational analysis: Genuine mutations vs. damage bypass-derived artifacts." Methods (2008); 46(4): 269-273.

Kunkel, T.A. "Mutational specificity of depurination." Proc Natl Acad Sci USA (1984); 81.5: 1494-1498.

LaTuga, M.S., et al. "Beyond bacteria: a study of the enteric microbial consortium in extremely low birth weight infants." PLoS ONE (2011); 6.12: e27858.

Lecroq, B., et al. "Ultradeep sequencing of foraminiferal microbarcodes unveils hidden richness of early monothalamous lineages in deep-sea sediments." Proc Natl Acad Sci USA (2011); 108(32): 13177-13182.

Lin, M.T., et al. "High aggregate burden of somatic mtDNA point mutations in aging and Alzheimer's disease brain." Hum Mol Genet (2002); 11.2: 133-145.

Lindahl, T and Wood, R.D. "Quality control by DNA repair." Science (1999); 286.5446: 1897-1905.

Lynch, A.M., et al. "New and emerging technologies for genetic toxicity testing." Environ Mol Mutagen. (2011); 52(3): 205-223.

Mackelprang, R., et al. "Metagenomic analysis of a permafrost microbial community reveals a rapid response to thaw." Nature (2011); 480.7377: 368-371.

McBride, T.J., et al. "Mutagenic spectrum resulting from DNA damage by oxygen radicals." Biochemistry (1991); 30.1: 207-213.

McCloskey, M.L., et al. "Encoding PCR products with batch-stamps and barcodes." Biochem Genet. (2007); 45(11-12): 761-767.

McCulloch, Scott D., and Kunkel, Thomas A. "The fidelity of DNA synthesis by eukaryotic replicative and translesion synthesis polymerases." Cell Research (2008); 18.1: 148-161.

Metzker, M.L. "Sequencing technologies-the next generation." Nat Rev Genet. (2010); 11.1: 31-46.

Meyerhans, A., et al. "DNA recombination during PCR." Nucleic Acids Research (1990);18.1: 1687-1691.

Miner, B.E., et al. "Molecular barcodes detect redundancy and contamination in hairpin-bisulfite PCR." Nucleic Acids Research (2004); 32.17: e135.

Minot, S., et al. "The human gut virome: interindividual variation and dynamic response to diet." Genome Research (2011); 21.10: 1616-1625.

Mitchell, P.S., et al. "Circulating microRNAs as stable blood-based markers for cancer detection." Proc Natl Acad Sci USA (2008); 105.30: 10513-10518.

Nasu, A., et al. Genetic heterogeneity of hepatitis C virus in association with antiviral therapy determined by ultra-deep sequencing. PLoS ONE (2011); 6.9: e24907.

Out, A.A., et al. "Deep sequencing to reveal new variants in pooled DNA samples." Hum Mutat. (2009); 30.12: 1703-1712.

Ozsolak, F., et al. "Direct RNA sequencing." Nature (2009); 461.7265: 814-818.

Parsons, T. J., et al. "A high observed substitution rate in the human mitochondrial DNA control region." Nat Genet (1997); 15.4: 363-368.

Quail, M.A., et al. A large genome center's improvements to the Illumina sequencing system. Nat Methods. (2008); 5.12: 1005-1010.

Roberts, C.H., et al. "Short template amplicon and multiplex megaprimer-enabled relay (STAMMER) sequencing, a simultaneous approach to higher throughput sequence-based typing of polymorphic genes." Immunogenetics (2010); 62(4): 253-260.

Salk, J., et al. "Mutational heterogeneity in human cancers: origin and conseauences." Annual Review of Pathology (2010); 5: 51-75.

Schmitt, Michael W., et al. "Detection of ultra-rare mutations by next-generation sequencing." Proceedings of the National Academy of Sciences (2012); 109.36: 14508-14513.

Shen, Y., et al. "A SNP discovery method to assess variant allele probability from next-generation resequencing data." Genome Res. (2010); 20.2 :273-280.

Shendure, J. and Ji, H. "Next-generation DNA sequencing." Nat Biotechnol. (2008); 26.10:1135-1145.

Shibutani, S., et al. "Insertion of specific bases during DNA synthesis past the oxidation-damaged base 8-oxodG." Nature (1991); 349: 431-434.

(56) References Cited

OTHER PUBLICATIONS

Shiroguchi, K., et al. "Digital RNA sequencing minimizes sequence-dependent bias and amplification noise with optimized single-molecule barcodes." Proc Natl Acad Sci USA. (2012); 109.4: 1347-1352.
Sikorsky, Jan A., et al. "DNA damage reduces Taq DNA polymerase fidelity and PCR amplification efficiency." Biochemical and Biophysical Research Communications (2007); 355.2: 431-437.
Song, S., et al. "DNA precursor asymmetries in mammalian tissue mitochondria and possible contribution to mutagenesis through reduced replication fidelity." Proc Natl Acad Sci USA (2005); 102.14: 4990-4995.
Stiller, M., et al. "Patterns of nucleotide misincorporations during enzymatic amplification and direct large-scale sequencing of ancient DNA." Proc Natl Acad Sci USA (2006); 103.37: 13578-13584.
Stoneking, M. "Hypervariable sites in the mtDNA control region are mutational hotspots." Am J Hum Genet (2000); 67.4: 1029-1032.
Thomas, D.C., et al. "Fidelity of mammalian DNA replication and replicative DNA polymerases." Biochemistry (1991); 30.51: 11751-11759.
Travers, K.J., et al. "A flexible and efficient template format for circular consensus sequencing and SNP detection." Nucleic Acids Res. (2010); 38: 159e1-8.
Vandenbroucke, I., et al. "Minor variant detection in amplicons using 454 massive parallel pyrosequencing: experiences and considerations for successful applications." Bio Techniques.(2011); 51: 167-177.
Vermulst, M., et al. "Mitochondrial point mutations do not limit the natural lifespan of mice." Nat Genet (2007); 39.4: 540-543.
Wang, C., et al. "Characterization of mutation spectra with ultra-deep pyrosequencing: application to HIV-1 drug resistance." Genome Res. (2007);-17.8: 1195-1201.
Yang, J., et al. "Unbiased parallel detection of viral pathogens in clinical samples by use of a metagenomic approach." J Clin Microbial. (2011); 49.10: 3463-3469.
Zagordi, O., et al. "Error correction of next-generation sequencing data and reliable estimation of HIV quasispecies." Nucleic Acids Research (2010); 38.21: 7400-7409.
Belousova, E.A. et al., Thermostable DNA polymerases can perform translesion synthesis using 8-oxoguanine and tetrahydrofuran-containing DNA templates, Biochimica et Biophysica Acta (BBA)—Proteins and Proteomics, 1764(1):97-104 (2006).
Bentley, D. et al., Accurate whole human genome sequencing using reversible terminator chemistry, Nature, 456:53-59 (2008).
Chiu, R.W.K. et al., Noninvasive prenatal diagnosis of fetal chromosomal aneuploidy by massively parallel genomic sequencing of DNA in maternal plasma, PNAS, 105:20458-20463 (2008).
Diehl, F. et al., Basic—Alimentary Tract—Analysis of Mutations in DNA Isolated From Plasma and Stool of Colorectal Cancer Patients, Gastroenterology, 135:489-498 (2008).
Diehl, F. et al., Detection and quantification of mutations in the plasma of patients with colorectal tumors, PNAS, 102:16368-16373 (2005).
Ding, Li et al., Analysis of next-generation genomic data in cancer: accomplishments and challenges, Human Molecular Genetics, 19:R188-R196 (2010).
Ewing, B. et al. Base-Calling of Automated Sequencer Traces Using Phred. II. Error Probabilities, Genome Research, 8:186-194 (1998).
Fleischhacker, M. et al., Circulating nucleic acids (CNAs) and cancer—A survey, Biochimica et Biophysica Acta. 1775:181-232 (2007).
Fong, Siew Lee et al., Comparison of 7 Methods for Extracting Cell-Free DNA from Serum Samples of Colorectal Cancer Patients, Clinical Chemistry, 55:587-598 (2009).
Forshew, T. et al., Noninvasive Identification and Monitoring of Cancer Mutations by Targeted Deep Sequencing of Plasma DNA, Science Translational Medicine, 4(136) 136ra68 (2012).
Gordon, David J. et al., Causes and consequences of aneuploidy in cancer, Nature Reviews Genetics 13:189-203 (2012).

International Search Report and Written Opinion for PCT/US2013/032665, 14 pages (dated Jul. 9, 2013).
Jiang, Hui et al., SeqMap: mapping massive amount of oligonucleotides to the genome, Bioinformatics, 24:2395-2396 (2008).
Kao, Wei-Chun et al., BayesCall: A model-based base-calling algorithm for high-throughput short-read sequencing, Genome Research 19:1884-1895 (2009).
Kircher, M. et al., Improved base calling for the Illumina Genome Analyzer using machine learning strategies, Genome Biology, 10:R83 (2009).
Kirsch, S. et al., Sequence error storms and the landscape of mutations in cancer, PNAS 109:14289-14290 (2012).
Ledergerber, C. et al., Base-calling for next-generation sequencing platforms, Briefings in Bioinformatics 12:489-497 (2011).
Li, H. et al., Fast and accurate short read alignment with Burrows-Wheeler transform, Bioinformatics, 25:1754-1760 (2009).
Li, H. et al., Mapping short DNA sequencing reads and calling variants using mapping quality scores, Genome Research, 18:1851-1858 (2008).
Liang, K. et al., Bayesian Basecalling for DNA Sequence Analysis Using Hidden Markov Models, IEEE/ACM Transactions on Computational Biology and Bioinformatics, 4:430-440 (2007).
Liao, G. et al., Targeted Massively Parallel Sequencing of Maternal Plasma DNA Permits Efficient and Unbiased Detection of Fetal Alleles, Clinical Chemistry, 57:92-101 (2011).
Lo, Y.M. Dennis et al., Quantitative Analysis of Fetal DNA in Maternal Plasma and Serum: Implications for Noninvasive Prenatal Diagnosis, Am. J. Hum. Genet., 62:768-775 (1998).
Lunter, G. et al., Stampy: A statistical algorithm for sensitive and fast mapping of Illumina sequence reads, Genome Research, 21:936-939 (2011).
McKernan, K. et al., Sequence and structural variation in a human genome uncovered by short-read, massively parallel ligation sequencing using two-base encoding, Genome Research, 19:1527-1541 (2009).
Mertes, F. et al., Targeted enrichment of genomic DNA regions for next-generation sequencing, Briefings in Functional Genomics, 10:374-386 (2011).
Meyer, M. et al., Targeted high-throughput sequencing of tagged nucleic acid samples, Nucleic Acids Research, 35(15) e97 (2007).
Meyerson, M. et al., Advances in understanding cancer genomes through second-generation sequencing, Nature Reviews Genetics, 11:685-696 (2010).
Nielsen, R. et al., Genotype and SNP calling from next-generation sequencing data, Nature Reviews Genetics, 12:443-451 (2011).
Quinlan, A. R. et al., Pyrobayes: an improved base caller for SNP discovery in pyrosequences, Nature Methods, 5:179-181 (2008).
Redon, R. et al., Global variation in copy number in the human genome, Nature, 444:444-454 (2006).
Rizzo, J. et al., Key Principles and Clinical Applications of Next-Generation DNA Sequencing, Cancer Prevention Research, 5(7):887-900 (2012).
Schwarzenbach, H. et al., Cell-free nucleic acids as biomarkers in cancer patients, Nature Reviews, 11:426-437 (2011).
Schweiger, M. R. et al., Genome-Wide Massively Parallel Sequencing of Formaldehyde Fixed-Paraffin Embedded (FFPE) Tumor Tissues for Copy-Number- and Mutation-Analysis, PLOS One, 4:e5548 (2009).
Sehnert, A. et al., Optimal Detection of Fetal Chromosomal Abnormalities by Massively Parallel DNA Sequencing of Cell-Free Fetal DNA from Maternal Blood, Clinical Chemistry, 57:1042-1049 (2011).
Sparks, A. et al., Selective analysis of cell-free DNA in maternal blood for evaluation of fetal trisomy, Prenatal Diagnosis, 32:3-9 (2012).
Wagle, N. et al., High-Throughput Detection of Actionable Genomic Alterations in Clinical Tumor Samples by Targeted, Massively Parallel Sequencing, AACR Cancer Discovery, 2:82-93 (2011).
Wiemann, S. et al., Simultaneous On-Line DNA Sequencing on Both Strands with Two Fluorescent Dyes Analytical Biochemistry, 224:117-121 (1995).
Ahn, E., et al., "Decreased Mitochondrial Mutagenesis during Transformation of Human Breast Stem Cells into Tumorigenic

(56) References Cited

OTHER PUBLICATIONS

Cells," Cancer Research 76(15); 4569-4578, American Association of Cancer Research, United States (Aug. 2016).

Akogwu, I., et al., "A comparative study of k-spectrum-based error correction methods for next-generation sequencing data analysis Human Genomics," 2(20); 50-59, Springer Nature, England (Jul. 2016).

Besaratinia, A., et al., "A high-throughput next-generation sequencing-based method for detecting the mutational fingerprint of carcinogens," Nucleic Acids Research 40(15); E116, Oxford Academic, United Kingdom (2012).

Bielas, J., et al., "Quantification of random genetic mutations," Nature Methods 2(4); 285-290, Nature Publishing Group, United Kingdom (2005).

Borodina, T., et al., "Chapter five—A Strand-Specific Library Preparation Protocol for RNA Sequencing," Methods in Enzymology 500; 79-98, Elsevier, Netherlands (2011).

Boyd, S., et al., "Measurement and Clinical Monitoring of Human Lymphocyte Clonality by Massively Parallel V-D-J Pyrosequencing," Science Translational Medicine 1:12ra23-12ra23, American Association for the Advancement of Science, United States (2009).

Chen, L., et al., "DNA damage is a pervasive cause of sequencing errors, directly confounding variant identification," Science 355;752-756, American Association for the Advancement of Science, United States (Feb. 2017).

Clark, T., et al., "Direct Detection and Sequencing of Damaged DNA Bases," Genome Integrity 2(10); 1-9, Biomed Central, Germany (2011).

Goodwin, S., et al., "Coming of age: ten years of next-generation sequencing technologies," Nature Reviews: Genetics 17;333-351, Nature Publishing Group, United Kingdom, (Jun. 2016).

Havens, J., "The technology and clinical applications of hybrid capture," NGSMedical Laboratory Observer retrieved from: https://www.mlo-online.com/home/article/13008809/the-technology-and-clinical-applications-of-hybrid-capture-ngs, published Jul. 2016, 5 pages.

Hiatt, J.B., et al., "Single molecule molecular inversion probes for targeted, high-accuracy detection of low-frequency variation," Genome Research 23;843-854, Cold Spring Harbor Laboratory Press, United States (2013).

Hodgkinson, A. et al., "Variation in the mutation rate across mammalian genomes," Nature Reviews Genetics 12; 756-766, Nature Publishing Group, United Kingdom (2011).

Jung, H., et al., "The DNA Integrity Number (DIN) Provided by the Genomic DNA Screen Tape Assay Allows for Streamlining of NGS of FPFE Tissue Samples Application Note Nucleic Acid Analysis," Agilent Technologies, 4 pages, Korea (Dec. 2015).

Kebschull, J.M., et al., "Sources of PCR-induced distortions in high-throughput sequencing data sets," Nucleic Acids Research 43(21);e143, Oxford Academic, United Kingdom (Jul. 2015).

Kennedy, S.R., et al., "Ultra-Sensitive Sequencing Reveals an Age-Related Increase in Somatic Mitochondrial Mutations That Are Inconsistent with Oxidative Damage, " PLOS Genetics, 9(9);e1003794 , PLOS, United States (Sep. 2013).

Kennedy, S.R., et al., "Detecting ultralow-frequency mutations by Duplex Sequencing," Nature Protocols 9(11); 2586-2606, Nature Publishing Group, England (Oct. 2014).

Krimmel, J.D., et al., "Ultra-deep sequencing detects ovarian cancer cells in peritoneal fluid and reveals somatic TP53 mutations in noncancerous tissues," PNAS, 113(21), 6005-6010, United States National Academy of the Sciences, United States (May 2016).

Liang, K-C., et al., "Bayesian Basecalling for DNA Sequence Analysis Using Hidden Markov Models," IEEE/ACM Transactions on Computational Biology and Bioinformatics 4:430-440, Institute of Electrical and Electronics Engineers and Association for Computing Machinery, United States (2007).

Lou, D., et al., High-throughput DNA sequencing errors are deduced by orders of magnitude using circle sequencing, PNAS 110(49); 19872-19877, United States National Academy of the Sciences, United States (Dec. 2013).

Lynch, M., et a., "Rate, molecular spectrum, and consequences of human mutation," PNAS 107(3); 961-968, United States National Academy of the Sciences, United States (2010).

Nachmanson, D., et al., "Targeted genome fragmentation with CRISPR/Cas9 improves hybridization capture, reduces PCR bias, and enables efficient high-accuracy sequencing of small targets," Genome Res. 28(10):1589-1599, Cold Spring Harbor Laboratory Press, United States (Oct. 2017).

Narayan, A., et al., "Ultrasensitive Measurement of Hotspot Mutations in Tumor DNA in Blood Using Error-Suppressed Multiplexed Deep Sequencing," Cancer Research 72(14); 3492-3498, American Association of Cancer Research, United States (2012).

Park, G., et al., "Characterization of background noise in capture-based targeted sequencing data," Genome Biology 18(136); 1-13, Biomed Central, Germany (Jul. 2017).

Pecuchet, N., et al., "Analysis of Base-Position Error Rate of Next-Generation Sequencing to Detect Tumor Mutations in Circulating DNA," Clinical Chemistry 62(11); 1492-1503, Oxford Academic, England (Nov. 2016).

Ran, F.A., et al., "Genome engineering using the CRISPR-Cas9 system," Nature Protocols, 8(11); 2281-2308, Nature Publishing Group, United Kingdom (Oct. 2013).

Robinson, J.T., et al., "Integrative genomics viewer," Nature Biotechnology 29(1); 24-26, Nature Publishing Group, United Kingdom (Jan. 2011).

Salk, J., et al., "Enhancing the accuracy of next-generation sequencing for detecting rare and subclonal mutation," Nature Reviews Genetics 19; 269-285, Nature Publishing Group, United Kingdom (May 2018).

Salk, J., et al., "Next-Generation Genotoxicology: Using Modern Sequencing Technologies to Assess Somatic Metagenesis and Cancer Risk," Environmental and Molecular Mutagenesis 61(1):135-151, Wiley Online Library, United States (2019).

Salk, J., et al., "Passenger mutations as a marker of clonal cell lineages in emerging neoplasia," Seminars in Cancer Biology 20;294-303, Elsevier, Netherlands (2010).

Schmitt, M.W., et al., "Sequencing small genomic targets with high efficiency and extreme accuracy," Nature Methods 12(5); 423-425, Nature Publishing Group, England (May 2015).

Shin, GW., et al., "CRISPR-Cas9-targeted fragmentation and selective sequencing enable massively parallel microsatellite analysis," Nature Communications 8;14291, Nature Publishing Group, England (2017).

Summerer, D., "Enabling technologies of genomic-scale sequence enrichment for targeted high-throughput sequencing," Genomics 94; 363-368, Elsevier, Netherlands (2009).

Teer, J-K., et al, "Sequence and structural variation in a human genome uncovered by short-read, massively parallel ligation sequencing using two-base encoding," Genome Research 20:1420-1431, Cold Spring Harbor Research, United States (2010).

International Search Report and Written Opinion for PCT/US2018/024194, dated Jul. 7, 2018. 10 pages.

Winters, M., et al., "Are we fishing or catching? Evaluating the efficiency of bait capture of CODIS fragments," Forensic Science International: Genetics 29; 61-70, Elsevier, Netherlands (Jul. 2017).

Yuan, B., et al., "High-throughput analysis of the mutagenic and cytotoxic properties of DNA lesions by next-generation sequencing," Nucleic Acids Research 39(14); 5945-5954, Oxford University Press, England (2011).

Zheng, Z., et al., "Anchored multiplex PCR for targeted next-generation sequencing," Nature Medicine 20(12); 1479-1484, Nature Publishing Group, England (Dec. 2014).

Makarova, K.S., et al., "Annotation and Classification of CRISPR-CAS Systems," Methods. Mol. Bio. 1311:47-75, Humana Press, United States (2015).

\* cited by examiner

Figure 1A
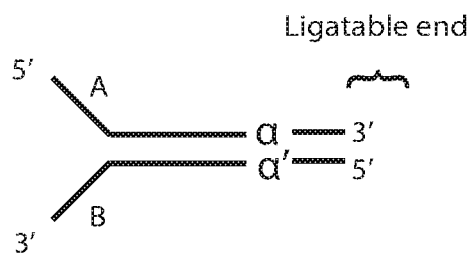
Figure 1B
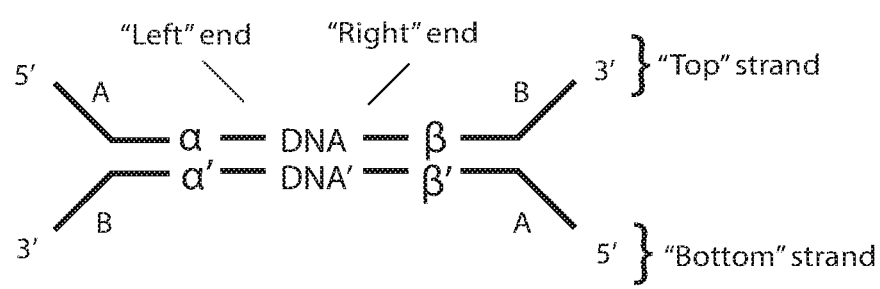
Figure 1C
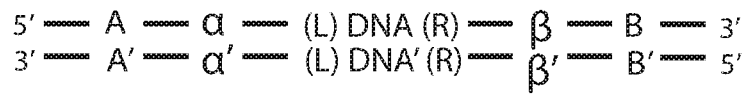
Figure 1D
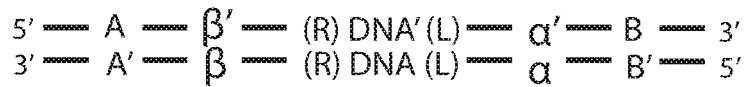
Figure 1E
|  | Read A | Read B |
|---|---|---|
| "Top" | α —— (L) DNA | β' —— (R) DNA' |
| "Bottom" | β' —— (R) DNA' | α —— (L) DNA |
Figure 1F
"Top"     α —— (L) DNA (R) —— β
"Bottom"  β' —— (R) DNA' (L) —— α'

Figure 1G

"Top"     β' —— (R) DNA'(L) —— α'

"Bottom"  α —— (L) DNA (R) —— β

Figure 1H

"Top"     α —— (L) DNA

"Bottom"  β' —— (R) DNA'

Figure 1I

"Top"     β' —— (R) DNA'

"Bottom"  α —— (L) DNA

Figure 3A
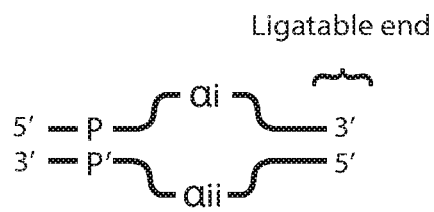
Figure 3B
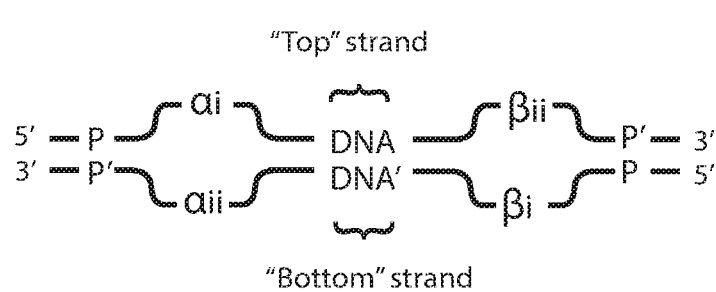
Figure 3C
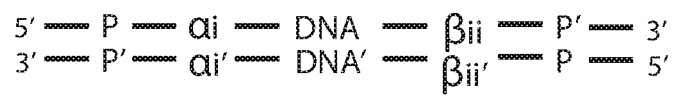
Figure 3D
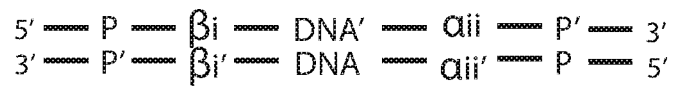
Figure 3E
$\alpha i$ —— DNA
$\beta ii'$ —— DNA'
Figure 3F
$\beta i$ —— DNA'
$\alpha ii'$ —— DNA
Figure 3G
$\alpha i$ —— DNA          $\beta i$ —— DNA'
$\alpha ii'$ —— DNA         $\beta ii'$ —— DNA'

Figure 4A
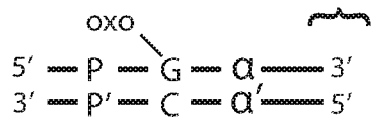
Figure 4B
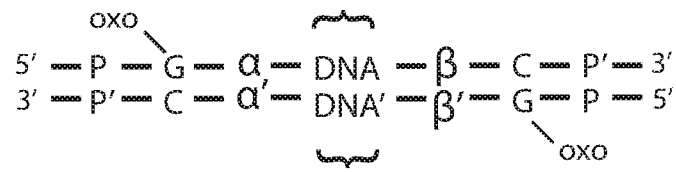
Figure 4C
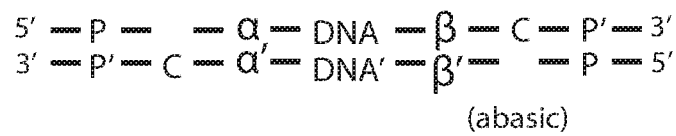
Figure 4D
Figure 4E
Figure 4F
T —— α —— DNA
G —— β' —— DNA'
Figure 4G
T —— β' —— DNA'
G —— α —— DNA
Figure 4H
T —— α —— DNA        G —— β' —— DNA'
G —— α —— DNA        T —— β' —— DNA'

Ligatable ends

"Top" strand

"Bottom" strand

Figure 6H                    Figure 6I read #1   DNA           read #1   DNA read #2   X — α         read #2   Y' — α

Figure 7A
Figure 7B
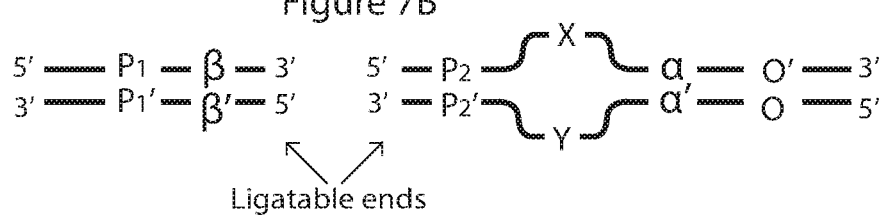
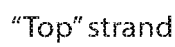
Ligatable ends
Figure 7C
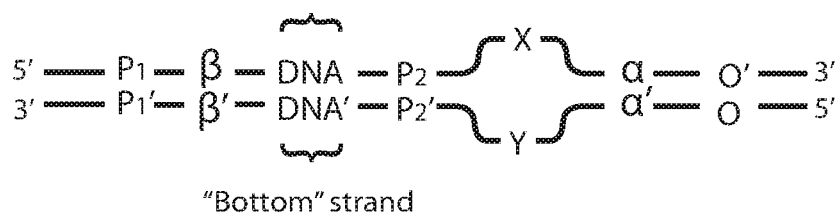
Figure 7D
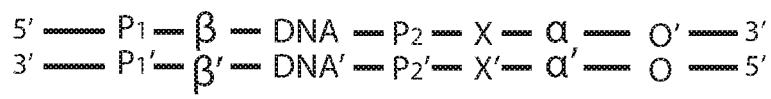
Figure 7E
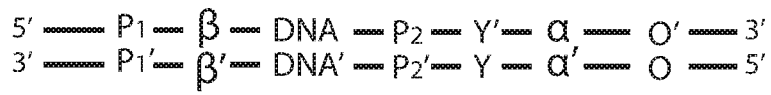
Figure 7F
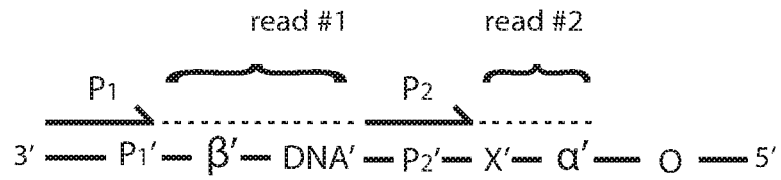
Figure 7G
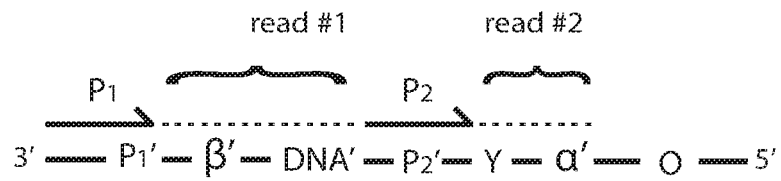
Figure 7H
read #1   β — DNA
read #2   X — α
Figure 7I
read #1   β — DNA
read #2   Y' — α

Figure 8A
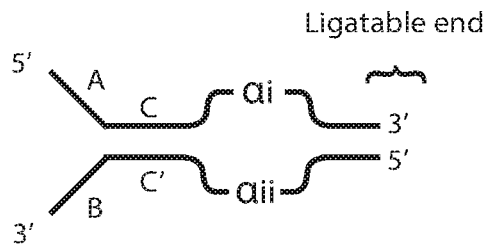
Figure 8B
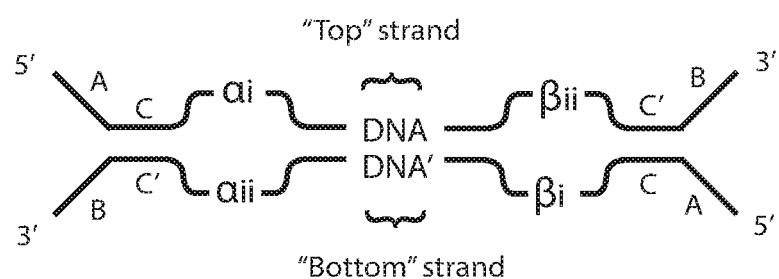
Figure 8C
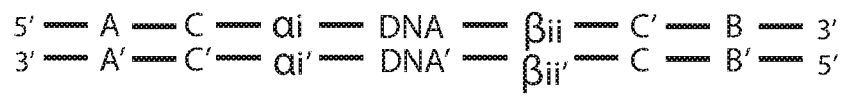
Figure 8D
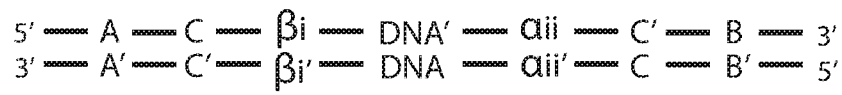
Figure 8E
$\alpha i$ —— DNA
$\beta ii'$ —— DNA'
Figure 8F
$\beta i$ —— DNA'
$\alpha ii'$ —— DNA
Figure 8G
$\alpha i$ —— DNA      $\beta i$ —— DNA'
$\alpha ii'$ —— DNA     $\beta ii'$ —— DNA'

| derived from "top" strand | | derived from "bottom" strand | |
|---|---|---|---|
| read #1 | DNA | read #1 | DNA' |
| read #2 | DNA' | read #2 | DNA |
| index #1 | βi | index #1 | αii |
| index #2 | αi' | index #2 | βii' |

Figure 11A
Figure 11B
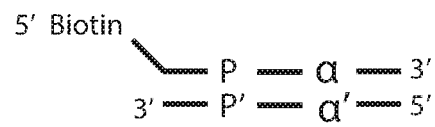
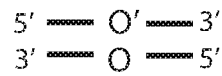
Ligatable ends
Figure 11C
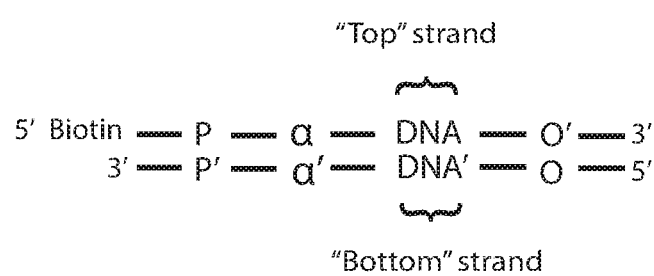
"Top" strand
"Bottom" strand
Figure 11D
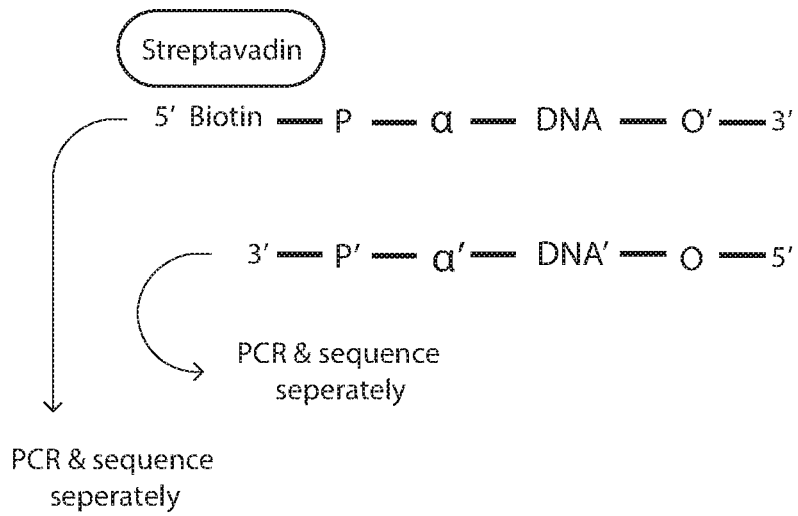

Ligatable ends

Figure 14G
Figure 14H
Figure 14I
"Top" strand    α ——— T ——— DNA
"Bottom" strand α ——— C ——— DNA

ADAPTERS, METHODS, AND COMPOSITIONS FOR DUPLEX SEQUENCING

CROSS-REFERENCE TO RELATED APPLICATIONS

This application is claims priority to and the benefit of U.S. Provisional Application No. 62/264,822, filed Dec. 8, 2015 and U.S. Provisional Application No. 62/281,917, filed Jan. 22, 2016. Each of the above-mentioned applications is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 8, 2016, is named TWIN-001_ST25.txt and is 11,778 bytes in size.

BACKGROUND OF THE INVENTION

Duplex Sequencing enables extreme improvements in the accuracy of high throughput DNA sequencing by separately amplifying and sequencing the two strands of duplex DNA; thus, amplification and sequencing errors can be eliminated as they will typically occur on only one of the two strands. Duplex Sequencing was initially described with asymmetric (i.e., non-complementary) PCR primer binding sites introduced into Y-shaped or "loop" adapters ligated to the ends of DNA fragments. The asymmetric primer binding sites present within the adapters themselves result in separate products from the two DNA strands, which enables error correction from each of the two DNA strands. Use of asymmetric primer binding sites may not be optimal in some circumstances; for example the free ends of the Y-adapters can be prone to degradation by exonucleases, and these free ends can also anneal to other molecules, resulting in "daisy-chaining" of molecules. Moreover, Duplex Sequencing with Y-shaped adapters or "loop" adaptors are most readily applied with paired-end sequencing approaches; alternative approaches applicable to single-end sequencing would simplify broader application of Duplex Sequencing on a variety of sequencing platforms.

Accordingly, an unmet need exists for approaches to Duplex Sequencing that do not involve use of asymmetric primer binding sites.

BRIEF SUMMARY OF THE INVENTION

Herein are described alternative and superior approaches to Duplex Sequencing that do not require use of asymmetric primer binding sites. Instead, asymmetry between the two strands can be introduced by creating a difference of at least one nucleotide in a DNA sequence between the two strands within an adaptor or elsewhere in the DNA molecule to be sequenced, or by differentially labeling the two strands in other ways, such as attachment of a molecule to at least one of the strands which enables physical separation of the two strands.

In a first aspect, the present invention relates to a pair of adapter nucleic acid sequences for use in sequencing a double-stranded target nucleic acid molecule including a first adapter nucleic acid sequence and a second adapter nucleic acid sequence, in which each adapter nucleic acid sequence includes a primer binding domain, a strand defining element (SDE), a single molecule identifier (SMI) domain, and a ligation domain. The SDE of the first adapter nucleic acid sequence may be at least partially non-complementary to the SDE of the second adapter nucleic acid sequence.

In embodiments of the first aspect, the two adapter sequences may include two separate DNA molecules that are at least partially annealed together. The first adapter nucleic acid sequence and the second adapter nucleic acid sequence may be linked via a linker domain. The linker domain may be comprised of nucleotides. The linker domain may include one or more modified nucleotide or non-nucleotide molecules. The one or more modified nucleotide or non-nucleotide molecule may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. The linker domain may form a loop. The SDE of the first adapter nucleic acid sequence may be non-complementary to the SDE of the second adapter nucleic acid sequence. The primer binding domain of the first adapter nucleic acid sequence may be at least partially complementary to the primer binding domain of the second adapter nucleic acid sequence. In embodiments, the primer binding domain of the first adapter nucleic acid sequence may be complementary to the primer binding domain of the second adapter nucleic acid sequence. The primer binding domain of the first adapter nucleic acid sequence may be at least partially non-complementary to the primer binding domain of the second adapter nucleic acid sequence. In embodiments, at least one SMI domain may be an endogenous SMI, e.g., is related to a shear point (e.g., using the shear point itself, using the actual mapping position of the shear point (e.g., chromosome 3, position 1,234,567), using a defined number of nucleotides in the DNA immediately adjacent to the shear point (e.g., ten nucleotides from the shear point, eight nucleotides that start seven nucleotides away from the shear point, and six nucleotides starting after the first incidence of "C" after the shear point)). In embodiments, the SMI domain includes at least one degenerate or semi-degenerate nucleic acid. In embodiments, the SMI domain may be non-degenerate. In embodiments, the sequence of the SMI domain may be considered in conjunction with the sequence corresponding to randomly or semi-randomly sheared ends of ligated DNA to obtain an SMI sequence capable of distinguishing single DNA molecules from one another. The SMI domain of the first adapter nucleic acid sequence may be at least partially complementary to the SMI domain of the second adapter nucleic acid sequence. The SMI domain of the first adapter nucleic acid sequence may be complementary to the SMI domain of the second adapter nucleic acid sequence. The SMI domain of the first adapter nucleic acid sequence may be at least partially non-complementary to the SMI domain of the second adapter nucleic acid sequence. In embodiments, each SMI domain includes a primer binding site. In embodiments, each SMI domain may be located distal to its ligation domain. The SMI domain of the first adapter nucleic acid sequence may be non-complementary to the SMI domain of the second adapter nucleic acid sequence. In embodiments, each SMI domain includes between about 1 to about 30 degenerate or semi-degenerate nucleic acids. The ligation domain of the first adapter nucleic acid sequence may be at least partially complementary to the ligation domain of the second adapter nucleic acid sequence. In embodiments, each ligation domain may be capable of being ligated to one strand of a double-stranded target nucleic acid sequence. In embodiments, one of the ligation domains includes a T-overhang, an A-overhang, a CG-overhang, a blunt end, or another ligateable nucleic acid sequence. In embodiments, both ligation domains comprise a blunt end. In embodiments, at least one of the ligation domains includes a modified nucleic acid. The modified nucleotide may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. In embodiments, at least one of the ligation domains includes a dephosphorylated base. In embodiments, at least one of the ligation domains includes a dehydroxylated base. In embodiments, at least one of the ligation domains has been chemically modified so as to render it unligateable. The SDE of the first adapter nucleic acid sequence differs by and/or may be non-complementary at at least one nucleotide from the SDE of the second adapter nucleic acid sequence. In embodiments, at least one nucleotide may be omitted from either the SDE of the first adapter nucleic acid sequence or from the SDE of the second adapter nucleic acid by an enzymatic reaction. The enzymatic reaction includes a polymerase, an endonuclease, a glycosylase, or a lyase. The at least one nucleotide may be a modified nucleotide or a nucleotide including a label. The modified nucleotide or a nucleotide including a label may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. The SDE of the first adapter nucleic acid sequence includes a self-complementary domain that may be capable of forming a hairpin loop. The end of first adapter nucleic acid sequence distal to its ligation domain may be ligated to the end of the second adapter nucleic acid sequence that may be distal to its ligation domain, thereby forming a loop. The loop includes a restriction enzyme recognition site. In embodiments, at least the first adapter nucleic acid sequence further includes a second SDE. The second SDE may be located at a terminus of the first adapter nucleic acid sequence. The second adapter nucleic acid sequence further includes a second SDE. The second SDE may be located at a terminus of the second adapter nucleic acid sequence. The second SDE of the first adapter nucleic acid sequence may be at least partially non-complementary to the second SDE of the second adapter nucleic acid sequence. The second SDE of the first adapter nucleic acid sequence differs by and/or may be non-complementary at at least one nucleotide from the second SDE of the second adapter nucleic acid sequence. In embodiments, at least one nucleotide may be omitted from either the second SDE of the first adapter nucleic acid sequence or from the second SDE of the second adapter nucleic acid by an enzymatic reaction. The enzymatic reaction includes a polymerase, an endonuclease, a glycosylase, or a lyase. The second SDE of the first adapter nucleic acid sequence may be non-complementary to the second SDE of the second adapter nucleic acid sequence. The SDE of the first adapter nucleic acid sequence may be directly linked to the second SDE of the second adapter nucleic acid sequence. The primer binding domain of the first adapter nucleic acid sequence may be located 5' to a first SDE. The first SDE of the first adapter nucleic acid sequence may be located 5' to the SMI domain. The first SDE of the first adapter nucleic acid sequence may be located 3' to the SMI domain. The first SDE of the first adapter nucleic acid sequence may be located 5' to the SMI domain and may be located 3' to the primer binding domain. The first SDE of the first adapter nucleic acid sequence may be located 3' to the SMI domain which may be located 3' to the primer binding domain. The SMI domain of the first adapter nucleic acid sequence may be located 5' to the ligation domain. The 3' terminus of the first adapter nucleic acid sequence includes the ligation domain. The first adapter nucleic acid sequence includes, from 5' to 3', the primer binding domain, the first SDE, the SMI domain, and the ligation domain. The first adapter nucleic acid sequence includes, from 5' to 3', the primer binding domain, the SMI domain, the first SDE, and the ligation domain. In embodiments, either the first adapter nucleic acid sequence or the second adapter nucleic acid sequence includes a modified nucleotide or a non-nucleotide molecule. The modified nucleotide or non-nucleotide molecule may be Colicin E2, Im2, Glutithione, glutathione-s-transferase (GST), Nickel, poly-histidine, FLAG-tag, myc-tag, or biotin. The biotin may be Biotin-16-Aminoallyl-2'-deoxyuridine-5'-Triphosphate, Biotin-16-Aminoallyl-2'-deoxycytidine-5'-Triphosphate, Biotin-16-Aminoallylcytidine-5'-Triphosphate, N4-Biotin-OBEA-2'-deoxycytidine-5'-Triphosphate, Biotin-16-Aminoallyluridine-5'-Triphosphate, Biotin-16-7-Deaza-7-Aminoallyl-2'-deoxyguanosine-5'-Triphosphate, Desthiobiotin-6-Aminoallyl-2'-deoxycytidine-5'-Triphosphate, 5'-Biotin-G-Monophosphate, 5'-Biotin-A-Monophosphate, 5'-Biotin-dG-Monophosphate, or 5'-Biotin-dA-Monophosphate. The biotin may be capable of being bound to a streptavidin attached to a substrate. In embodiments, when the biotin is bound to a streptavidin attached to a substrate, the first adapter nucleic acid sequence is capable of separating from the second adapter nucleic acid sequence. In embodiments, either the first adapter nucleic acid sequence or the second adapter nucleic acid sequence includes an affinity label selected from a small molecule, a nucleic acid, a peptide, and a uniquely bindeable moiety which may be capable of being bound by an affinity partner. In embodiments, when the affinity partner is attached to a solid substrate and bound to the affinity label the adapter nucleic acid sequence including the affinity label is capable of being separated from the adapter nucleic acid sequence not including the affinity label. The solid substrate may be a solid surface, a bead, or another fixed structure. The nucleic acid may be DNA, RNA, or a combination thereof, and optionally, including a peptide-nucleic acid or a locked nucleic acid. The affinity label may be located at a terminus of an adapter or within a domain in the first adapter nucleic acid sequence that may be not completely complementary to an opposing domain in the second adapter nucleic acid sequence. In embodiments, either the first adapter nucleic acid sequence or the second adapter nucleic acid sequence includes a physical group having a magnetic property, a charge property, or an insolubility property. In embodiments, when the physical group has a magnetic property and a magnetic field is applied, the adapter nucleic acid sequence including the physical group is separated from the adapter nucleic acid sequence not including the physical group. In embodiments, when the physical group has a charge property and an electric field is applied, the adapter nucleic acid sequence including the physical group is separated from the adapter nucleic acid sequence not including the physical group. In embodiments, when the physical group has an insolubility property and the pair of adapter nucleic acid sequences are contained in a solution for which the physical group is insoluble, the adapter nucleic acid sequence including the physical group is precipitated away from the adapter nucleic acid sequence not including the physical group which remains in solution. The physical group may be located at a terminus of an adapter or within a domain in the first adapter nucleic acid sequence that may be not completely complementary to an opposing domain in the second adapter nucleic acid sequence. The second adapter nucleic acid sequence includes at least one phosphorothioate bond. The double-stranded target nucleic acid sequence may be DNA or RNA. In embodiments, each adapter nucleic acid sequences includes a ligation domain at each of its termini. The first adapter nucleic acid sequence or the second adapter nucleic acid sequence may be at least partially single-stranded. The first adapter nucleic acid sequence or the second adapter nucleic acid sequence may be single-stranded. The first adapter nucleic acid sequence and the second adapter nucleic acid sequence may be single-stranded.

In a second aspect, the present invention relates to a composition including at least one pair of adapter nucleic acid sequences of the first aspect and a second pair of adapter nucleic acid sequences in which each strand of the second pair of adapter nucleic acid sequences includes at least a primer binding site and a ligation domain.

The second aspect further relates to a composition including at least two pairs of adapter nucleic acid sequences the first aspect, in which the SDE of a first adapter nucleic acid sequence from a first pair of adapter nucleic acid sequences differs from the SDE of a first adapter nucleic acid sequence from at least a second pair of adapter nucleic acid sequences.

The second aspect also relates to a composition including at least two pairs of adapter nucleic acid molecules of the first aspect, in which the SMI domain of a first adapter nucleic acid molecule from a first pair of adapter nucleic acid molecules differs from the SMI domain of a first adapter nucleic acid molecule from an at least second pair of adapter nucleic acid molecules.

In embodiments of the second aspect, the composition further includes an SMI domain in each strand of the second pair of adapter nucleic acid sequence. The composition may further include a primer binding site in each strand of the second pair of adapter nucleic acid sequence. The SMI domain of the first adapter nucleic acid molecule from the first pair of single-stranded adapter nucleic acid molecules may be the same length as the SMI domain of the first single-stranded adapter nucleic acid molecule from the at least second pair of single-stranded adapter nucleic acid molecules. The SMI domain of the first adapter nucleic acid molecule from the first pair of single-stranded adapter nucleic acid molecules may have a different length than the SMI domain of the first single-stranded adapter nucleic acid molecule from the at least second pair of single-stranded adapter nucleic acid molecules. In embodiments, each SMI domain includes one or more fixed bases at a site within or flanking the SMI. In embodiments, at least a first double-stranded complexed nucleic acid including a first pair of adapter nucleic acid molecules of the first aspect is ligated to a first terminus of a double-stranded target nucleic acid molecule and a second pair of adapter nucleic acid molecules of the first aspect is ligated to a second terminus of the double-stranded target nucleic acid molecule. The first pair of adapter nucleic acid molecules may be different from the second pair of adapter nucleic acid molecules. The first strand adapter-target nucleic acid molecule of the first pair of adapter nucleic acid molecules includes a first SMI domain and the first strand adapter-target nucleic acid molecule of the second pair of adapter nucleic acid molecules includes a second SMI domain. In embodiments, the composition includes at least a second double-stranded complexed nucleic acid.

In a third aspect, the present invention relates to a pair of adapter nucleic acid sequences for use in sequencing a double-stranded target nucleic acid molecule including a first adapter nucleic acid sequence and a second adapter nucleic acid sequence. In the third aspect, each adapter nucleic acid sequence includes a primer binding domain and a single molecule identifier (SMI) domain.

In embodiments of the third aspect, at least one of the first adapter nucleic acid sequence or the second adapter nucleic acid sequence further includes a domain including at least one modified nucleotide. The first adapter nucleic acid sequence and the second adapter nucleic acid sequence further comprise a domain including at least one modified nucleotide. In embodiments, at least one of the first adapter nucleic acid sequence or the second adapter nucleic acid sequence further includes a ligation domain. The first adapter nucleic acid sequence and the second adapter nucleic acid sequence may include a ligation domain. The at least one modified nucleotide may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. The two adapter sequences may include two separate DNA molecules that are at least partially annealed together. The first adapter nucleic acid sequence and the second adapter nucleic acid sequence may be linked via a linker domain. The linker domain may be comprised of nucleotides. The linker domain may include one or more modified nucleotide or non-nucleotide molecules. In embodiments, at least one modified nucleotide or non-nucleotide molecule may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. The linker domain may form a loop. The primer binding domain of the first adapter nucleic acid sequence may be at least partially complementary to the primer binding domain of the second adapter nucleic acid sequence. The primer binding domain of the first adapter nucleic acid sequence may be complementary to the primer binding domain of the second adapter nucleic acid sequence. The primer binding domain of the first adapter nucleic acid sequence may be non-complementary to the primer binding domain of the second adapter nucleic acid sequence. In embodiments, at least one SMI domain is an endogenous SMI, e.g., is related to a shear point (e.g., using the shear point itself, using the actual mapping position of the shear point (e.g., chromosome 3, position 1,234,567), using a defined number of nucleotides in the DNA immediately adjacent to the shear point (e.g., ten nucleotides from the shear point, eight nucleotides that start seven nucleotides away from the shear point, and six nucleotides starting after the first incidence of "C" after the shear point)). The SMI domain includes at least one degenerate or semi-degenerate nucleic acid. The SMI domain may be non-degenerate. The sequence of the SMI domain may be considered in conjunction with the sequence corresponding to randomly or semi-randomly sheared ends of ligated DNA to obtain an SMI sequence capable of distinguishing single DNA molecules from one another. The SMI domain of the first adapter nucleic acid sequence may be at least partially complementary to the SMI domain of the second adapter nucleic acid sequence. The SMI domain of the first adapter nucleic acid sequence may be complementary to the SMI domain of the second adapter nucleic acid sequence. The SMI domain of the first adapter nucleic acid sequence may be at least partially non-complementary to the SMI domain of the second adapter nucleic acid sequence. The SMI domain of the first adapter nucleic acid sequence may be non-complementary to the SMI domain of the second adapter nucleic acid sequence. In embodiments, each SMI domain includes between about 1 to about 30 degenerate or semi-degenerate nucleic acids. The ligation domain of the first adapter nucleic acid sequence may be at least partially complementary to the ligation domain of the second adapter nucleic acid sequence. In embodiments, each ligation domain may be capable of being ligated to one strand of a double-stranded target nucleic acid sequence. In embodiments, one of the ligation domains includes a T-overhang, an A-overhang, a CG-overhang, a blunt end, or another ligateable nucleic acid sequence. In embodiments, both ligation domains comprise a blunt end. In embodiments, each SMI domain includes a primer binding site. In embodiments, at least the first adapter nucleic acid sequence further includes an SDE. The SDE may be located at a terminus of the first adapter nucleic acid sequence. The second adapter nucleic acid sequence further includes an SDE. The SDE may be located at a terminus of the second adapter nucleic acid sequence. The SDE of the first adapter nucleic acid sequence may be at least partially non-complementary to the SDE of the second adapter nucleic acid sequence. The SDE of the first adapter nucleic acid sequence may be non-complementary to the SDE of the second adapter nucleic acid sequence. The SDE of the first adapter nucleic acid sequence may be directly linked to the SDE of the second adapter nucleic acid sequence. The SDE of the first adapter nucleic acid sequence differs by and/or may be non-complementary at at least one nucleotide from the SDE of the second adapter nucleic acid sequence. The least one nucleotide may be omitted from either the SDE of the first adapter nucleic acid sequence or from the SDE of the second adapter nucleic acid by an enzymatic reaction. The enzymatic reaction may include a polymerase or an endonuclease. The at least one nucleotide may be a modified nucleotide or a nucleotide including a label. The modified nucleotide or a nucleotide including a label may be an abasic site, a uracil, tetrahydrofuran, 8-oxo-7,8-dihydro-2'-deoxyadenosine (8-oxo-A), 8-oxo-7,8-dihydro-2'-deoxyguanosine (8-oxo-G), deoxyinosine, 5'-nitroindole, 5-Hydroxymethyl-2'-deoxycytidine, iso-cytosine, 5'-methyl-isocytosine, or iso-guanosine. The SDE of the first adapter nucleic acid sequence may comprise a self-complementary domain that is capable of forming a hairpin loop. The end of first adapter nucleic acid sequence distal to its ligation domain may be ligated to the end of the second adapter nucleic acid sequence that is distal to its ligation domain, thereby forming a loop. The loop may include a restriction enzyme recognition site. The primer binding domain of the first adapter nucleic acid sequence may be located 5' to the SMI domain. The domain including at least one modified nucleotide of the first adapter nucleic acid sequence may be located 5' to the SMI domain. The domain including at least one modified nucleotide of the first adapter nucleic acid sequence may be located 3' to the SMI domain. The domain including at least one modified nucleotide of the first adapter nucleic acid sequence may be located 5' to the SMI domain and may be located 3' to the primer binding domain. The domain including at least one modified nucleotide of the first adapter nucleic acid sequence may be located 3' to the SMI domain which may be located 3' to the primer binding domain. The SMI domain of the first adapter nucleic acid sequence may be located 5' to the ligation domain. The 3' terminus of the first adapter nucleic acid sequence may include the ligation domain. In embodiments, the first adapter nucleic acid sequence includes, from 5' to 3', the primer binding domain, the domain including at least one modified nucleotide, the SMI domain, and the ligation domain. In embodiments, the first adapter nucleic acid sequence includes, from 5' to 3', the primer binding domain, the SMI domain, the domain including at least one modified nucleotide, and the ligation domain. In embodiments, either the first adapter nucleic acid sequence or the second adapter nucleic acid sequence includes a modified nucleotide or a non-nucleotide molecule. The modified nucleotide or non-nucleotide molecule may be Colicin E2, Im2, Glutithione, glutathione-s-transferase (GST), Nickel, poly-histidine, FLAG-tag, myc-tag, or biotin. The biotin may be Biotin-16-Aminoallyl-2'-deoxyuridine-5'-Triphosphate, Biotin-16-Aminoallyl-2'-deoxycytidine-5'-Triphosphate, Biotin-16-Aminoallylcytidine-5'-Triphosphate, N4-Biotin-OBEA-2'-deoxycytidine-5'-Triphosphate, Biotin-16-Aminoallyluridine-5'-Triphosphate, Biotin-16-7-Deaza-7-Aminoallyl-2'-deoxyguanosine-5'-Triphosphate, Desthiobiotin-6-Aminoallyl-2'-deoxycytidine-5'-Triphosphate, 5'-Biotin-G-Monophosphate, 5'-Biotin-A-Monophosphate, 5'-Biotin-dG-Monophosphate, or 5'-Biotin-dA-Monophosphate. The biotin may be capable of being bound to a streptavidin attached to a substrate. In embodiments, when the biotin is bound to a streptavidin attached to a substrate, the first adapter nucleic acid sequence is capable of separating from the second adapter nucleic acid sequence. The second adapter nucleic acid sequence may include at least one phosphorothioate bond. The double-stranded target nucleic acid sequence may be DNA or RNA. In embodiments, either the first adapter nucleic acid sequence or the second adapter nucleic acid sequence includes an affinity label selected from a small molecule, a nucleic acid, a peptide, and a uniquely bindeable moiety which is capable of being bound by an affinity partner. In embodiments, when the affinity partner is attached to a solid substrate and bound to the affinity label the adapter nucleic acid sequence including the affinity label is capable of being separated from the adapter nucleic acid sequence not including the affinity label. The solid substrate may be a solid surface, a bead, or another fixed structure. The nucleic acid may be DNA, RNA, or a combination thereof, and optionally, including a peptide-nucleic acid or a locked nucleic acid. The affinity label may be located at a terminus of an adapter or within a domain in the first adapter nucleic acid sequence that may be not completely complementary to an opposing domain in the second adapter nucleic acid sequence. In embodiments, either the first adapter nucleic acid sequence or the second adapter nucleic acid sequence includes a physical group having a magnetic property, a charge property, or an insolubility property. In embodiments, when the physical group has a magnetic property and a magnetic field is applied, the adapter nucleic acid sequence including the physical group is separated from the adapter nucleic acid sequence not including the physical group. In embodiments, when the physical group has a charge property and an electric field is applied, the adapter nucleic acid sequence including the physical group is separated from the adapter nucleic acid sequence not including the physical group. In embodiments, when the physical group has an insolubility property and the pair of adapter nucleic acid sequences are contained in a solution for which the physical group is insoluble, the adapter nucleic acid sequence including the physical group is precipitated away from the adapter nucleic acid sequence not including the physical group which remains in solution. The physical group may be located at a terminus of an adapter or within a domain in the first adapter nucleic acid sequence that may be not completely complementary to an opposing domain in the second adapter nucleic acid sequence. The first adapter nucleic acid sequence or the second adapter nucleic acid sequence may be at least partially single-stranded. The first adapter nucleic acid sequence or the second adapter nucleic acid sequence may be single-stranded. The first adapter nucleic acid sequence and the second adapter nucleic acid sequence may be single-stranded. In embodiments, at least one of the ligation domains includes a dehydroxylated base. In embodiments, at least one of the ligation domains has been chemically modified so as to render it unligateable.

In a fourth aspect, the present invention relates to a composition including at least two pairs of adapter nucleic acid molecules of the third aspect in which the SMI domain of a first adapter nucleic acid molecule from a first pair of adapter nucleic acid molecules differs from the SMI domain of a first adapter nucleic acid molecule from an at least second pair of adapter nucleic acid molecules.

In embodiments of the fourth aspect, the SMI domain of the first adapter nucleic acid molecule from the first pair of single-stranded adapter nucleic acid molecules may be the same length as the SMI domain of the first single-stranded adapter nucleic acid molecule from the at least second pair of single-stranded adapter nucleic acid molecules. The SMI domain of the first adapter nucleic acid molecule from the first pair of single-stranded adapter nucleic acid molecules may have a different length than the SMI domain of the first single-stranded adapter nucleic acid molecule from the at least second pair of single-stranded adapter nucleic acid molecules. In embodiments, each SMI domain includes one or more fixed bases at a site within or flanking the SMI.

In a fifth aspect, the present invention relates to a composition including at least a first double-stranded complexed nucleic acid including a first pair of adapter nucleic acid molecules of the third aspect ligated to a first terminus of a double-stranded target nucleic acid molecule and a second pair of adapter nucleic acid molecules of the third aspect ligated to a second terminus of the double-stranded target nucleic acid molecule.

In embodiments of the fifth aspect, the first pair of adapter nucleic acid molecules may be different from the second pair of adapter nucleic acid molecules. The first strand adapter-target nucleic acid molecule of the first pair of adapter nucleic acid molecules may include a first SMI domain and the first strand adapter-target nucleic acid molecule of the second pair of adapter nucleic acid molecules may include a second SMI domain. The first strand adapter-target nucleic acid molecule of the first pair of adapter nucleic acid molecules may include a first SMI domain and the first strand adapter-target nucleic acid molecule of the second pair of adapter nucleic acid molecules includes a second SMI domain. In embodiments, the composition includes at least a second double-stranded complexed nucleic acid.

In a sixth aspect, the present invention relates to a composition including at least one pair of adapter nucleic acid molecules of the first aspect and at least one pair of adapter nucleic acid molecules of the third aspect.

In a seventh aspect, the present invention relates to a composition including at least a first double-stranded complexed nucleic acid including a first pair of adapter nucleic acid molecules of the first aspect ligated to a first terminus of a double-stranded target nucleic acid molecule and a second pair of adapter nucleic acid molecules of the third aspect ligated to a second terminus of the double-stranded target nucleic acid molecule.

In an eighth aspect, the present invention relates to a method of sequencing a double-stranded target nucleic acid including steps of: (1) ligating a pair of adapter nucleic acid sequences of the first aspect to at least one terminus of a double-stranded target nucleic acid molecule, thereby forming a double-stranded nucleic acid molecule including a first strand adapter-target nucleic acid sequence and a second strand adapter-target nucleic acid sequence, (2) amplifying the first strand adapter-target nucleic acid sequence, thereby producing a first set of amplified products including a plurality of first strand adapter-target nucleic acid sequences and a plurality of its complementary molecules, (3) amplifying the second strand adapter-target nucleic acid sequence, thereby producing a second set of amplified products including a plurality of second strand adapter-target nucleic acid sequences and a plurality of its complementary molecules, in which the second set of amplified products may be distinguishable from the first set of amplified products, (4) sequencing the first set of amplified products, and (5) sequencing the second set of amplified products.

In embodiments of the eighth aspect, the at least one terminus may be two termini. The amplification may be performed by PCR, by multiple displacement amplification, or by isothermal amplification. The pair of adapter nucleic acid sequences ligated to a first terminus of the double-stranded target nucleic acid sequence has an identical structure to the pair of adapter nucleic acid sequences ligated to a second terminus of the double-stranded target nucleic acid sequence. In embodiments of the eighth aspect, the first strand adapter-target nucleic acid sequence includes in 5' to 3' order: (a) a first adapter nucleic acid sequence, (b) a first strand of the double-stranded target nucleic acid, and (c) a second adapter nucleic acid sequence. In embodiments of the eighth aspect, the second strand adapter-target nucleic acid sequence may include in 3' to 5' order: (a) a first adapter nucleic acid sequence, (b) a second strand of the double-stranded target nucleic acid, and (c) a second adapter nucleic acid sequence. The pair of adapter nucleic acid sequences ligated to a first terminus of the double-stranded target nucleic acid sequence may be different from the pair of adapter nucleic acid sequences ligated to a second terminus of the double-stranded target nucleic acid sequence. The pair of adapter nucleic acid sequences ligated to a first terminus of the double-stranded target nucleic acid sequence has a first SMI domain and the pair of adapter nucleic acid sequences ligated to a second terminus of the double-stranded target nucleic acid sequence has a second SMI domain in which in which the first SMI domain may be different from the second SMI domain. In embodiments of the eighth aspect, the first strand adapter-target nucleic acid sequence may include in 5' to 3' order: (a) a first adapter nucleic acid sequence including the first SDE, (b) a first SMI domain, (c) a first strand of the double-stranded target nucleic acid, and (d) a second adapter nucleic acid sequence. In embodiments of the eighth aspect, the second strand adapter-target nucleic acid sequence may include in 5' to 3' order: (a) a first adapter nucleic acid sequence including the first SDE, (b) a second SMI domain, (c) a second strand of the double-stranded target nucleic acid, and (d) a second adapter nucleic acid sequence. In embodiments, the consensus sequence for the first set of amplified products may be compared to the consensus sequence for the second set of amplified products and a difference between the two consensus sequences may be considered an artifact.

In a ninth aspect, the present invention relates to a method of sequencing a double-stranded target nucleic acid including steps of: (1) ligating a pair of adapter nucleic acid sequences of the third aspect to at least one terminus of a double-stranded target nucleic acid molecule, thereby forming a double-stranded nucleic acid molecule including a first strand adapter-target nucleic acid sequence and a second strand adapter-target nucleic acid sequence, (2) amplifying the first strand adapter-target nucleic acid molecule, thereby producing a first set of amplified products including a plurality of first strand adapter-target nucleic acid molecules and a plurality of its complementary molecules, (3) amplifying the second strand adapter-target nucleic acid molecule, thereby producing a second set of amplified products including a plurality of second strand adapter-target nucleic acid molecules and a plurality of its complementary molecules, (4) sequencing the first set of amplified products, thereby obtaining a consensus sequence for the first set of amplified products, and (5) sequencing the second set of amplified products, thereby obtaining a consensus sequence for the second set of amplified products.

In embodiments of the ninth aspect, the second set of amplified products may be distinguishable from the first set of amplified products. The amplification may be performed by PCR, by multiple displacement amplification, or by isothermal amplification. In embodiments of the ninth aspect, the method further includes, after step (1), a step of contacting the double-stranded nucleic acid molecule with at least one enzyme (e.g., a glycosylase) that changes the at least one modified nucleotide to another chemical structure. The pair of adapter nucleic acid sequences ligated to a first terminus of the double-stranded target nucleic acid molecule may be identical to the pair of adapter nucleic acid sequences ligated to a second terminus of the double-stranded target nucleic acid molecule. The pair of adapter nucleic acid sequences ligated to a first terminus of the double-stranded target nucleic acid molecule may be different from to the pair of adapter nucleic acid sequences ligated to a second terminus of the double-stranded target nucleic acid molecule. In embodiments, a pair of adapter nucleic acid sequences may be ligated to a first terminus of a double-stranded target nucleic acid molecule and a primer corresponding to a portion of the DNA sequence of the target DNA molecule may be utilized to amplify the DNA molecule. In embodiments of the ninth aspect, the first strand adapter-target nucleic acid sequence includes in 5' to 3' order: (a) a first adapter nucleic acid sequence which includes the at least one modified nucleotide or the at least one abasic site, (b) a first strand of the double-stranded target nucleic acid, and (c) a second adapter nucleic acid sequence. In embodiments of the ninth aspect, the second strand adapter-target nucleic acid sequence includes in 3' to 5' order: (a) a first adapter nucleic acid sequence, (b) a second strand of the double-stranded target nucleic acid, and (c) a second adapter nucleic acid sequence. The pair of adapter nucleic acid sequences ligated to a first terminus of the double-stranded target nucleic acid molecule may be different from the pair of adapter nucleic acid sequences ligated to a second terminus of the double-stranded target nucleic acid molecule. The pair of adapter nucleic acid sequences ligated to a first terminus of the double-stranded target nucleic acid molecule has a first SMI domain and the pair of adapter nucleic acid sequences ligated to a second terminus of the double-stranded target nucleic acid sequence has a second SMI domain, in which the first SMI domain may be different from the second SMI domain. In embodiments of the ninth aspect, the first strand adapter-target nucleic acid sequence includes in 5' to 3' order: (a) a first adapter nucleic acid sequence including the at least one modified nucleotide or the at least one abasic site and the first SMI domain, (b) a first strand of the double-stranded target nucleic acid, and (c) a second adapter nucleic acid sequence including the second SMI domain. In embodiments, when the at least one modified nucleotide may be 8-oxo-G, and the second adapter nucleic acid sequence includes a cytosine at a position corresponding to the 8-oxo-G. In embodiments of the ninth aspect, the second strand adapter-target nucleic acid sequence includes in 3' to 5' order: (a) a first adapter nucleic acid sequence including the first SMI domain, (b) a second strand of the double-stranded target nucleic acid, and (c) a second adapter nucleic acid sequence including the second SMI domain. In embodiments, the at least one modified nucleotide may be 8-oxo-G, the second adapter nucleic acid sequence includes a cytidine at a position corresponding to the 8-oxo-G. In embodiments, during the amplification of step (2) or step (3), the at least one abasic site may be converted upon amplification into a thymidine in the corresponding amplified product, resulting in introduction of an SDE. In embodiments of the ninth aspect, during the amplification of step (2) or step (3), the at least one modified nucleotide site encodes an adenosine in the corresponding amplified product.

In a tenth aspect, the present invention relates to a method in which distinguishable amplification products may be obtained from each of the two strands of individual DNA molecules, and the consensus sequence for the first set of amplified products may be compared to the consensus sequence for the second set of amplified products, in which a difference between the two consensus sequences can be considered an artifact.

In embodiments of the tenth aspect, the amplified products may be determined to have arisen from the same initial DNA molecule by virtue of sharing the same SMI sequence. In embodiments, the amplified products may be determined to have arisen from the same initial DNA molecule by virtue carrying distinct SMI sequences that may be known to correspond to each other based upon a database produced at the time of and in conjunction with SMI adaptor library synthesis. In embodiments, amplified products may be determined to have arisen from distinct strands of the same initial double stranded DNA sequence via at least one nucleotide of sequence difference that was introduced by an SDE.

In an eleventh aspect, the present invention relates to a method in which distinguishable amplification products may be obtained from each of the two strands of individual DNA molecules, and the sequence obtained from an amplified product corresponding to one of the two initial DNA strands of a single DNA molecule is compared to an amplified product corresponding to the second of the two initial DNA strands, and a difference between the two sequences may be considered an artifact.

In a twelfth aspect, the present invention relates to a method in which indistinguishable amplification products may be obtained from the two strands of an individual DNA molecule when the sequence obtained from an amplified product corresponding to one of the two initial DNA strands of a single DNA molecule is compared to an amplified product corresponding to the second of the two initial DNA strands and no difference between the two sequences is identified.

In embodiments of the twelfth aspect, the amplified products may be determined to have arisen from the same initial double stranded DNA molecule by virtue of sharing the same SMI sequence based upon database produced at the time of and in conjunction with SMI adaptor library synthesis. In embodiments, the amplified products may be determined to have arisen from distinct strands of the same initial double stranded DNA sequence via at least one nucleotide of sequence difference that was introduced by an SDE. In embodiments, the method further includes a step of single-molecule dilution following thermal or chemical melting of DNA duplexes into their component single-strands. The single-strands may be diluted into multiple physically-separated reaction chambers such that the probability of the two originally paired strands sharing the same container may be small. The physically-separated reaction chambers may be selected from containers, tubes, wells, and at least a pair of non-communicating droplets. In embodiments, the PCR amplification may be carried out for each physically-separated reaction chamber, preferably using primers for each chamber carrying a different tag sequence. In embodiments, each tag sequence operates as an SDE. In embodiments, a series of paired sequences corresponding to the two strands of the same initial DNA may be compared to one another, and at least one sequence from the series of products may be selected as most likely to represent the correct sequence of the initial DNA molecule. The product selected as most likely to represent the correct sequence of the initial DNA molecule may be selected at least in part due to having the smallest number of mismatches between the products obtained from the two DNA strands. The product selected as most likely to represent the correct sequence of the initial DNA molecule may be selected at least in part due to having the smallest number of mismatches relative to the reference sequence.

In a thirteenth aspect, the present invention relates to a composition including at least two pairs of adapter nucleic acid sequences, in which a first pair of adapter nucleic acid sequences includes: a primer binding domain, a strand defining element (SDE), and a ligation domain, in which a second pair of adapter nucleic acid sequences includes: a primer binding domain, a single molecule identifier (SMI) domain, and a ligation domain.

In a fourteenth aspect, the present invention relates to a double-stranded complexed nucleic acid including: (1) a first pair of adapter nucleic acid sequences including: a primer binding domain, and an SDE, and (2) a double-stranded target nucleic acid, and (3) a second pair of adapter nucleic acid sequences including: a primer binding domain, and a single molecule identifier (SMI) domain, in which the first pair of adapter nucleic acid molecules may be ligated to a first terminus of the double-stranded target nucleic acid molecule and the second pair of adapter nucleic acid molecules may be ligated to a second terminus of the double-stranded target nucleic acid molecule. In embodiments of the fourteenth aspect, the first pair of adapter nucleic acid sequences and/or the second pair of adapter nucleic acid sequences may further include a ligation domain.

In a fifteenth aspect, the present invention relates to pair of adapter nucleic acid sequences for use in sequencing a double-stranded target nucleic acid molecule, including a first adapter nucleic acid sequence and a second adapter nucleic acid sequence, in which each adapter nucleic acid sequence includes: a primer binding domain, an SDE, a ligation domain, in which the SDE of the first adapter nucleic acid sequence may be at least partially non-complementary to the SDE of the second adapter nucleic acid sequence.

In a sixteenth aspect, the present invention relates to a double-stranded circular nucleic acid including a pair of adapter nucleic acid molecules of the first aspect ligated to a first terminus of a double-stranded target nucleic acid molecule and ligated to a second a second terminus of the double-stranded target nucleic acid molecule.

In a seventeenth aspect, the present invention relates to a double-stranded circular nucleic acid including a pair of adapter nucleic acid molecules of the third aspect ligated to a first terminus of a double-stranded target nucleic acid molecule and ligated to a second a second terminus of the double-stranded target nucleic acid molecule.

In a eighteenth aspect, the present invention relates to a double-stranded circular nucleic acid including a pair of adapter nucleic acid molecules of the first aspect ligated to a first terminus of a double-stranded target nucleic acid molecule and an annealed pair of primer binding domains ligated to a second terminus of the double-stranded target nucleic acid molecule, in which the annealed pair of primer binding domains may be ligated to the pair of adapter nucleic acid molecules.

In a nineteenth aspect, the present invention relates to a double-stranded circular nucleic acid including a pair of adapter nucleic acid molecules of the third aspect ligated to a first terminus of a double-stranded target nucleic acid molecule and an annealed pair of primer binding domains ligated to a second terminus of the double-stranded target nucleic acid molecule, in which the annealed pair of primer binding domains may be ligated to the pair of adapter nucleic acid molecules.

In a twentieth aspect, the present invention relates to a double-stranded complexed nucleic acid including: (1) a pair of adapter nucleic acid sequences including: a primer binding domain, a strand defining element (SDE), and a single molecule identifier (SMI) domain, (2) a double-stranded target nucleic acid, and (3) an annealed pair primer binding domains, in which the pair of adapter nucleic acid molecules may be ligated to a first terminus of the double-stranded target nucleic acid molecule and the annealed pair primer binding domains may be ligated to a second terminus of the double-stranded target nucleic acid molecule. In embodiments of the twentieth aspect, the pair of adapter nucleic acid sequences and/or the annealed pair primer binding domains further includes a ligation domain.

Duplex Sequencing is additionally described in WO2013142389A1 and in Schmitt et al, *PNAS* 2012, each of which is incorporated herein by reference in its entirety.

Any of the above aspects and embodiments can be combined with any other aspect or embodiment as disclosed here in the Summary, in the Drawings, and/or in the Detailed Description, including the below specific, non-limiting, examples/embodiments of the present invention.

Other features, advantages, and modifications of the invention will be apparent from the Drawings, Detailed Description, and claims. The foregoing description is intended to illustrate and not limit the scope of the disclosure.

BRIEF DESCRIPTION OF THE SEVERAL
VIEWS OF THE DRAWINGS

The above and further features will be more clearly appreciated from the following Detailed Description when taken in conjunction with the accompanying drawings.

FIG. 1A to FIG. 1I illustrate originally-described Duplex Sequencing using Y-shaped adaptors. Shown is an exemplary Y-shaped adapter (FIG. 1A), a double-stranded DNA molecule ligated to such an adaptor (FIG. 1B), PCR products derived therefrom (FIG. 1C and FIG. 1D), and sequencing reads thus produced (FIG. 1E to FIG. 1I).

FIG. 3A to FIG. 3G illustrate Duplex Sequencing of the present invention using adapters having a non-complementary "bubble" shaped Single Molecule Identifier (SMI) which jointly serves as a molecular identifier as well as an asymmetry-introducing Strand Defining Element (SDE). Shown is an exemplary "bubble" adaptor (FIG. 3A), a double-stranded DNA molecule ligated to the adaptor of FIG. 3A (FIG. 3B), PCR products derived therefrom (FIG. 3C and FIG. 3D), and sequencing reads thus produced (FIG. 3E and FIG. 3F). FIG. 3G shows the sequencing reads of FIG. 3E and FIG. 3F grouped by specific SMI sequences and their corresponding non-complementary partner.

FIG. 4A to FIG. 4H illustrate Duplex Sequencing of the present invention using adapters having a nucleotide or nucleotide analog which initially forms a paired strand DNA, but is then rendered into a DNA mismatch following a subsequent biochemical reaction. Shown is an exemplary adaptor (FIG. 4A) comprising 8-oxo-7,8-dihydro-2'-deoxyguanosine (8-oxo-G), a double-stranded DNA molecule ligated to the adaptor of FIG. 4A (FIG. 4B), FIG. 4C shows the double-stranded DNA molecule of FIG. 4B after treatment with a glycosylase which creates an abasic site that replaces the 8-oxo-G bases and, thereby, a mismatch in the adapter; PCR products derived therefrom (FIG. 4D and FIG. 4E), and sequencing reads thus produced (FIG. 4F to FIG. 4H).

Figure 5A:
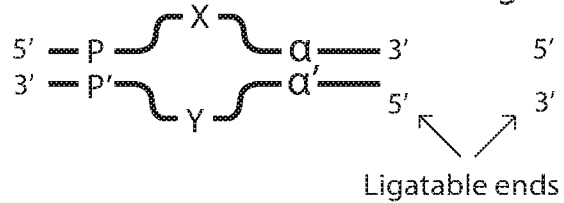
Figure 5B:
Figure 5C:
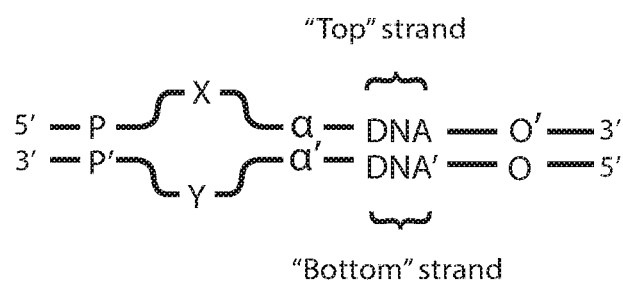
Figure 5D:
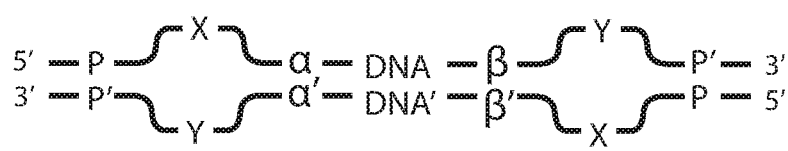
Figure 5E:
Figure 5F:
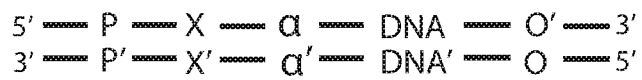
Figure 5G:
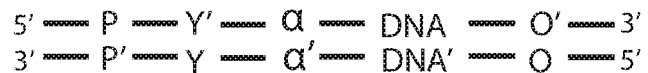
Figure 5H:
Figure 5H:
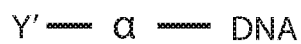

FIG. 5A to FIG. 5H illustrate Duplex Sequencing of the present invention using combinations of Duplex Sequencing adapter designs to introduce different primer sites on opposite ends of DNA molecules. Shown is an exemplary Duplex Sequencing adaptor (FIG. 5A) and a "standard" adapter (FIG. 5B), three types of a double-stranded DNA molecule are produced when the adaptors of FIG. 5A and FIG. 5B are ligated to the DNA molecule (FIG. 5C to FIG. 5E), PCR products derived therefrom (FIG. 5F and FIG. 5G), and sequencing reads thus produced (FIG. 5H).

Figures 6A, 6B:
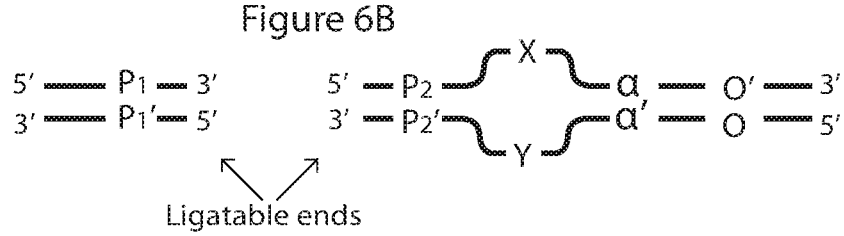

FIG. 6A to FIG. 6I illustrate Duplex Sequencing of the present invention using combinations of Duplex Sequencing adapter designs which allows two reads on non-paired-end platforms. Shown is a "standard" adapter (FIG. 6A) and an exemplary Duplex Sequencing adaptor (FIG. 6B), a preferred double-stranded DNA molecule produced when the adaptors of FIG. 6A and FIG. 6B are ligated to the DNA molecule (FIG. 6C), PCR products derived therefrom (FIG. 6D and FIG. 6E), the arrangement for the sequencing template strand derived from the "top" strand (FIG. 6F) and the "bottom" strand (FIG. 6G), and sequencing reads thus produced (FIG. 6H and FIG. 6I).

FIG. 7A to FIG. 7I illustrate Duplex Sequencing of the present invention using combinations of Duplex Sequencing adapter designs which allows two reads on non-paired-end platforms. Shown is an adapter (FIG. 7A) which additionally includes a degenerate or semi-degenerate SMI sequence and an exemplary Duplex Sequencing adaptor (FIG. 7B), a preferred double-stranded DNA molecule produced when the adaptors of FIG. 7A and FIG. 7B are ligated to the DNA molecule (FIG. 7C), PCR products derived therefrom (FIG. 7D and FIG. 7E, the arrangement for the sequencing template strand derived from the "top" strand (FIG. 7F) and the "bottom" strand (FIG. 7G), and sequencing reads thus produced (FIG. 7H and FIG. 7I).

Figure 8H:
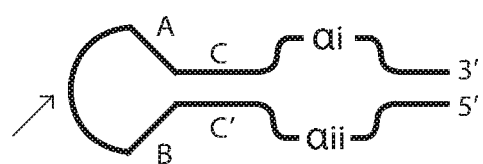
Figure 8I:
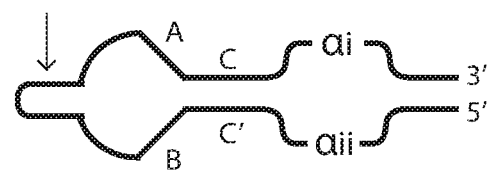
Figure 8J:
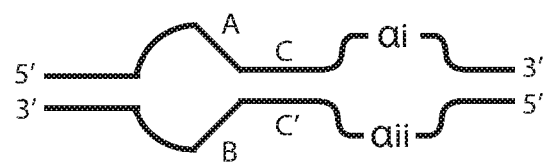

FIG. 8A to FIG. 8J illustrate Duplex Sequencing of the present invention using Y-shaped Duplex Sequencing adapters having asymmetric SMIs. Shown is an exemplary Duplex Sequencing adaptor (FIG. 8A), a double-stranded DNA molecule produced when the adaptor of FIG. 8A is ligated to the DNA molecule (FIG. 8B), PCR products derived therefrom (FIG. 8C and FIG. 8D), and sequencing reads thus produced (FIG. 8E and FIG. 8F). FIG. 8G shows the sequencing reads of FIG. 8E and FIG. 8F grouped by specific SMI sequences and their corresponding non-complementary partner. FIG. 8H to FIG. 8J show alternative adapter designs useful in this embodiment.

Figure 9A:
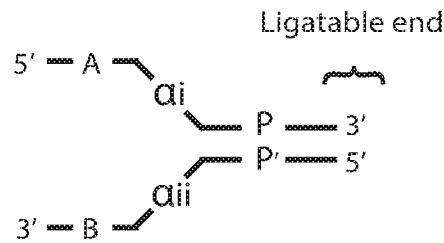
Figure 9B:
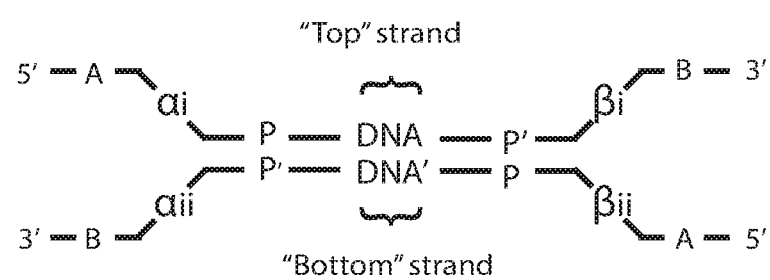
Figure 9C:
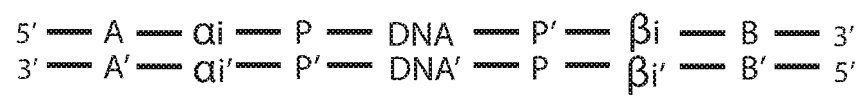
Figure 9D:
Figure 9E:
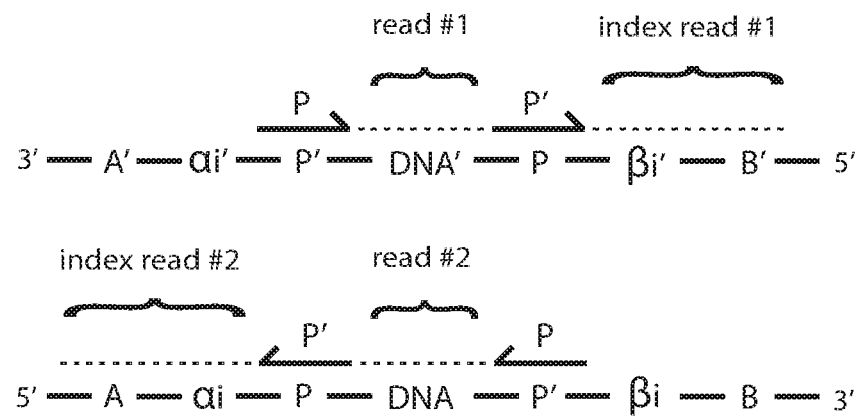
Figures 9F, 9G:
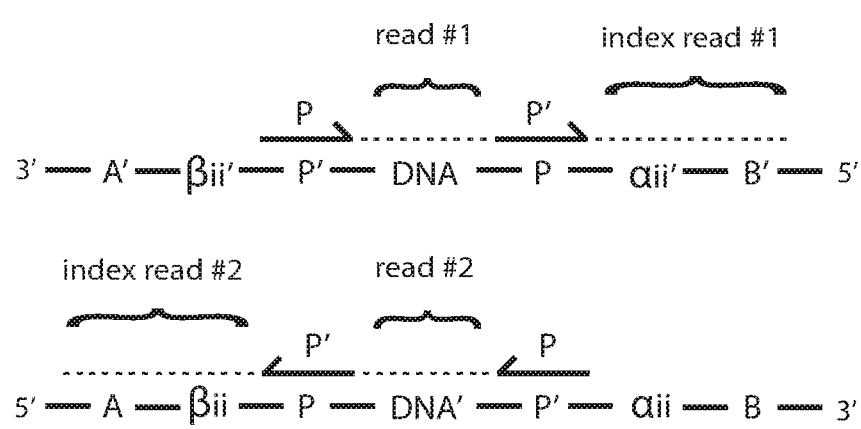

FIG. 9A to FIG. 9G illustrate Duplex Sequencing of the present invention using Y-shaped or loop-shaped Duplex Sequencing adapters having asymmetric SMIs located in the free single-stranded tail regions. Shown is an exemplary Duplex Sequencing adaptor (FIG. 9A), a preferred double-stranded DNA molecule produced when the adaptor of FIG. 9A is ligated to the DNA molecule (FIG. 9B), PCR products derived therefrom (FIG. 9C and FIG. 9D), the orientation of sequencing primer sites and indexing primer sites are shown in FIG. 9E and FIG. 9F. FIG. 9G shows the grouping sequencing reads obtained in the methods shown in FIG. 9E and FIG. 9F.

Figure 10A:
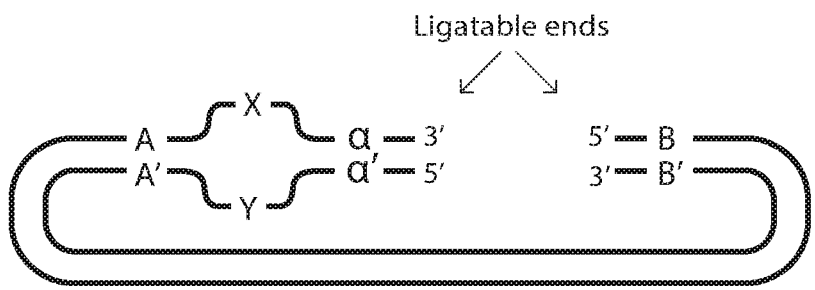
Figure 10B:
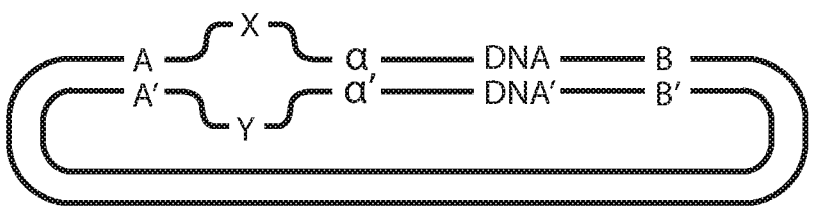
Figure 10C:
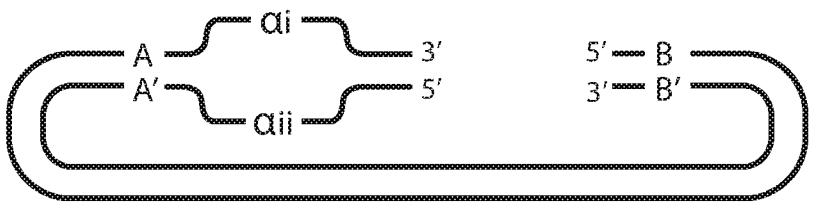
Figure 10D:
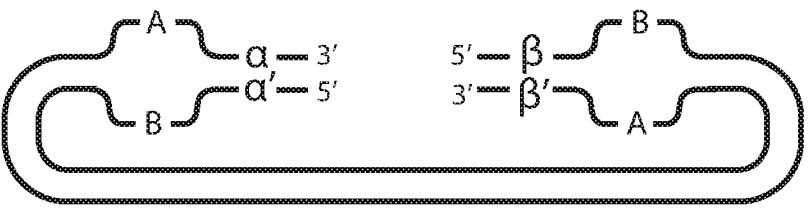
Figure 10E:
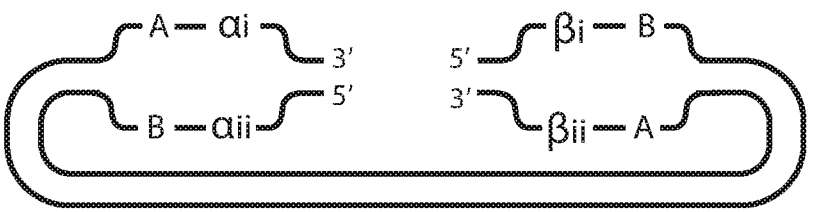

FIG. 10A to FIG. 10E illustrate Duplex Sequencing of the present invention in which all elements necessary for Duplex Sequencing are included in a single molecule rather than in two paired adapters. FIG. 10A shows such a configuration prior to ligation of a double-stranded DNA molecule and FIG. 10B shows the configuration of FIG. 10A after ligation of a double-stranded DNA molecule. FIG. 10C to FIG. 10E show some alternatives for this embodiment.

FIG. 11A to FIG. 11D illustrate Duplex Sequencing through asymmetric chemical labeling and strand isolation. Shown is an exemplary Duplex Sequencing adaptor (FIG. 11A) having a chemical tag (here, biotin) and a second adapter (FIG. 11B), a preferred double-stranded DNA molecule produced when the adaptor of FIG. 11A and the adapter of FIG. 11B is ligated to the DNA molecule (FIG. 11C), and further steps in the method in which the strand comprising the chemical tag is separated from the other strand and each are independently amplified and sequenced (FIG. 11D).

FIG. 12A to FIG. 12M illustrate Duplex Sequencing of the present invention in which an SDE is introduced by nick translation. FIG. 12A to FIG. 12D show an adapter design in which a SDE is lost following nick translation. Shown are Ion Torrent™-compatible adapters useful in this embodiment (FIG. 12E and FIG. 12F), a preferred double-stranded DNA molecule produced when the adaptors of FIG. 12E and FIG. 12F are ligated to a DNA molecule (FIG. 12G), mis-incorporation of terminal nucleotides (FIG. 12H), extension product derived therefrom and which show the mismatches (FIG. 12I), PCR products derived from the molecule of FIG. 12I (FIG. 12J and FIG. 12K), and sequencing reads thus produced (FIG. 12L and FIG. 12M).

Figure 13A:
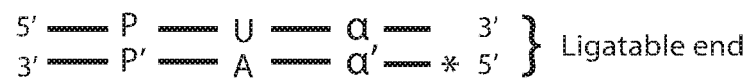
Figure 13B:
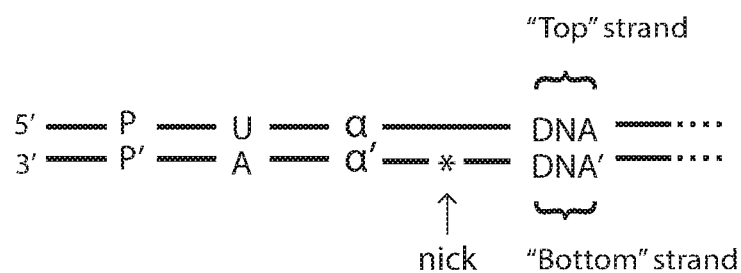
Figure 13C:
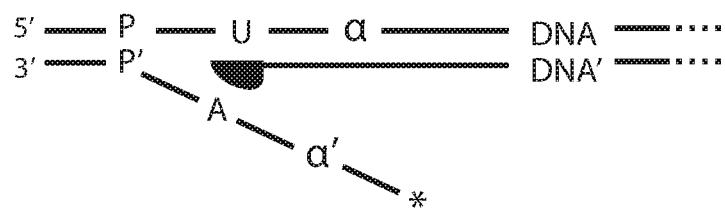
Figure 13D:
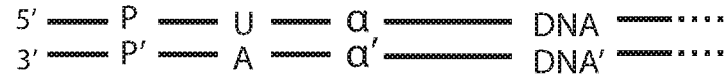
Figure 13E:
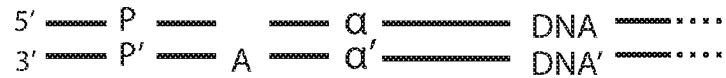
Figure 13F:
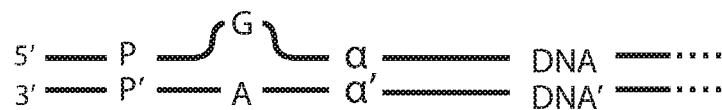
Figure 13G:
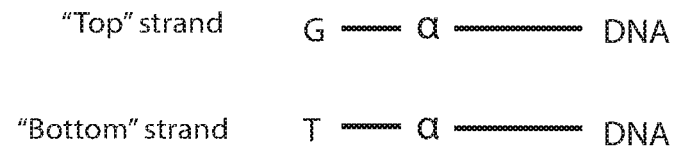

FIG. 13A to FIG. 13G illustrate Duplex Sequencing of the present invention in which an SDE is introduced following nick translation. Shown are a Duplex Sequencing adapter comprising a dephosphorylated 5' end (FIG. 13A), a double-stranded DNA molecule produced when the adaptor of FIG. 13A is ligated to a DNA molecule (FIG. 13B), a structure after strand displacement synthesis has occurred (FIG. 13C), an extension product of the structure of FIG. 13C (FIG. 13D) which shows no mismatches, a structure including a gap following treatment with uracil DNA glycosylase and an appropriate AP endonuclease (FIG. 13E), the structure of FIG. 13E after the gap has been filled in with a mis-matching nucleotide and ligated closed (FIG. 13F), and sequencing reads thus produced (FIG. 13G).

Figure 14A:
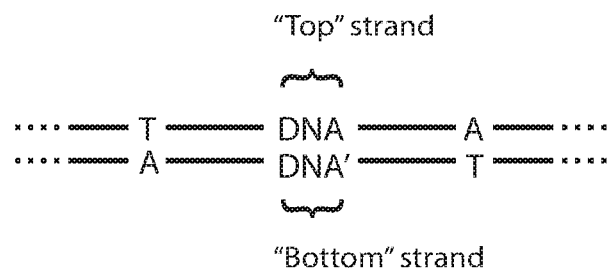
Figure 14B:
Figure 14C:
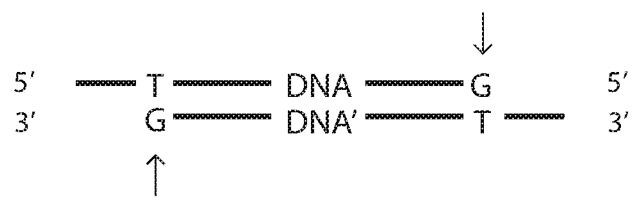
Figure 14D:
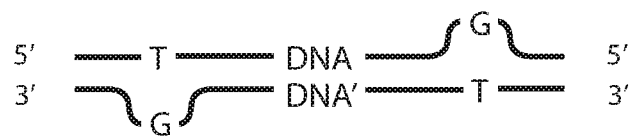
Figure 14E:
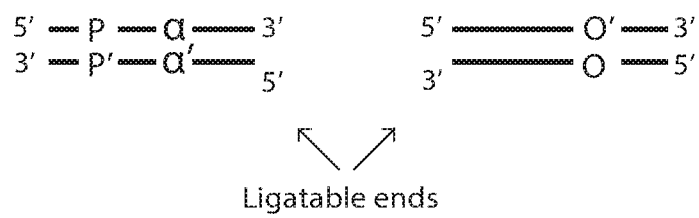
Figure 14F:

FIG. 14A to FIG. 14I illustrate Duplex Sequencing of the present invention in which a mismatch is introduced, by polymerase extension, into a DNA molecule to be sequenced. Shown are a double-stranded DNA molecule to be sequenced (FIG. 14A), the double stranded DNA molecule of FIG. 14A which has been treated with an endonuclease that leaves a 5' overhang (FIG. 14B); the partially double-stranded DNA molecule of FIG. 14B is treated to introduce two mismatches (FIG. 14C), the extension product of the structure of FIG. 14C (FIG. 14D) which now includes a "bubble" at each mismatch, a pair of adapters are shown in FIG. 14E, the structure of FIG. 14F is produced when the adaptors of FIG. 14E are ligated to a DNA molecule of FIG. 14D, PCR products derived from the molecule of FIG. 14F (FIG. 14G and FIG. 14H), and sequencing reads thus produced (FIG. 14I).

DETAILED DESCRIPTION OF THE INVENTION

Duplex Sequencing was initially described with use of asymmetric primer binding sites for separate amplification of the two DNA strands. Herein are described alternative and superior approaches to Duplex Sequencing that do not require use of asymmetric primer binding sites. Instead, asymmetry between the two strands can be introduced by creating a difference of at least one nucleotide in DNA sequence between the two strands within an adaptor or elsewhere in the DNA molecule to be sequenced (e.g., a mismatch, an additional nucleotide, and an omitted nucleotide), replacement of at least one nucleotide with a modified nucleotide (e.g., a nucleotide lacking a base or with an atypical base), and/or inclusion of at least one labeled nucleotide (e.g., a biotinylated nucleotide) which can physically separate the two strands. Table 1 illustrates exemplary options for assembling adapters for Duplex Sequencing as disclosed in the present invention.

TABLE 1

| Strand defining element (SDE) | Single molecule identifier (SMI) |
|---|---|
| Mismatch of at least one nucleotide is present internally within the adapter (i.e., "bubble adapter") | SMI adjacent to bubble<br>SMI within the bubble itself<br>SMI is in a second adapter<br>"endogenous SMI" (shear points) |
| A "matched" sequence is converted to a mismatch by a subsequent step<br>    mismatch is created by enzyme treatment (example: 8-oxo-G)<br>    mismatch is introduced by a polymerase (example: nick translation) | SMI adjacent to bubble<br>SMI within the bubble itself<br>SMI is in a second adapter<br>"endogenous SMI" (shear points) |
| Different sequences are present within adapter tails (i.e., "Y adapter") | SMI adjacent to adapter tails<br>SMI within the tails themselves<br>SMI is in a second adapter<br>"endogenous SMI" (shear points) |
| The two strands are physically separated (e.g., with biotin on one strand, but not the other) | SMI within the adapter itself<br>SMI is in a second adapter<br>"endogenous SMI" (shear points) |
| The two strands are different lengths<br>    internal "loop" within one adapter strand<br>    additional nucleotide is added to one strand but not the other | SMI within the adapter itself<br>SMI is in a second adapter<br>"endogenous SMI" (shear points) |

NOTES:

(i) All of these adapter designs may have additional, optional elements added (e.g., the two adapter strands are linked together and utilize PCR primer sites in various configurations)

(ii) Whenever an SMI is used, it can be random/degenerate, semi-random/semi-degenerate, or pre-defined. Also, if the SMI comprises two strands, the two strands can be either complementary, non-complementary, or partially complementary.

(iii) The complete adapted molecular complex, containing at least one SDE and at least one SMI, can be present in the adapters and/or the DNA to be ligated prior to attachment, may be generated following ligation, or may be a combination thereof.

The herein-described adapter designs and approaches for Duplex Sequencing are not dependent upon use of Y-adapters with complementary SMI sequences.

Some designs are directly applicable to single-end sequencing. The approaches disclosed herein share two general features: (1) each single stranded half of an individual duplex DNA molecule is labeled in such a way that the sequences that ultimately derive from each of the two strands can be recognized as being related to the same DNA duplex and (2) each single strand of an individual duplex DNA molecule is labeled in such a way that the sequences that ultimately derive from each of the two strands can be recognized as being distinct from those derived from the opposite strand. The molecular features that serve these respective functions are herein entitled Single Molecule Identifier (SMI) and Strand Defining Element (SDE).

This is the first disclosed introduction of strand-defining asymmetry via different versions of an internal non-complementary "bubble" sequence. One such embodiment involves introducing a non-complementary "bubble" sequence that is not located within the amplification primer sites; distinct sequences from the two strands of the "bubble" will then result in separate labeling of the two strands.

Disclosed herein is how strand-defining asymmetry can similarly be introduced into adapted DNA molecules through use of modified DNA bases as an SDE. In examples, asymmetry is introduced by including one or more nucleotide analogs that result in a complementary sequence initially, but which can subsequently be converted to a non-complementary sequence.

Also disclosed are ways in which non-Y-shaped asymmetric adaptor designs can be applied to sequencing platforms which require a different primer sequence on opposite ends of each DNA molecule.

Herein are disclosed alternate ways in which different types of SMI tags and SDEs can be distributed among two different primer-site containing adaptors for the benefit of maximizing read-length and SMI tagging diversity.

Also disclosed herein are additional designs for Duplex Sequencing adaptors that comprise Y or loop-shaped tails which are readily amenable to paired-end sequencing, but where SMI tags are not complementary sequences, and therefore allow significant design flexibility.

Demonstrated here is how such introduction of such asymmetry enables distinguishing products from the two DNA strands for purposes of error correction by Duplex Sequencing. Moreover, demonstrated herein are descriptions of how some embodiments facilitate performing Duplex Sequencing on single-end read platforms.

Further disclosed are methods for introducing primer sites and the SMI sites and the SDE sites for Duplex Sequencing with a single adapter to form a circular adapter-DNA molecule complex.

Additionally disclosed is a wholly different approach to introduction of an SDE that relies on asymmetric chemical tagging which allows physical/mechanical separation of paired strands into distinct reaction compartments for independent analysis, rather than differential sequence-based molecular tagging of the two strands.

Disclosed herein are examples of adapter designs specifically for the Ion Torrent™ (Life Technologies®) sequencing platform.

Disclosed herein are variants of adapters that can be ligated to both single strands at each end of a duplex molecule, as well as designs that allow single-stranded ligation followed by "nick translation" that retains both the necessary SMI and SDE elements in the final prepared molecule.

Disclosed herein is how an SDE can be incorporated into a DNA molecule itself in a way that is independent of adapter ligation.

Finally, disclosed herein are streamlined alternate algorithmic approaches for Duplex Sequencing that can be used with any Duplex Adaptor design that eliminates the need for preceding Single-Stranded Consensus Sequence (SSCS) generation.

In some embodiments, a portion of a nucleotide sequence may be "degenerate". In a degenerate sequence, each position may be any nucleotide, i.e., each position, represented by "X," "N", or "M", may be an adenine (A), cytosine (C), guanine (G), thymine (T), or uracil (U) or any other natural or non-natural DNA or RNA nucleotide or nucleotide-like substance or analog with base-pairing properties (e.g., xanthosine, inosine, hypoxanthine, xanthine, 7-methylguanine, 7-methylguanosine, 5,6-dihydrouracil, 5-methylcytosine, dihydouridine, isocytosine, isoguanine, deoxynucleosides, nucleosides, peptide nucleic acids, locked nucleic acids, glycol nucleic acids and threose nucleic acids). Alternately, a portion of a nucleotide sequence may be not entirely degenerate such that the sequence includes at least one pre-defined nucleotide or at least one pre-defined polynucleotides and positions that may be any nucleotide or one or more positions that includes only a subset combination of possible nucleotides. A subset combination of possible nucleotides could include: any three of the following: A, C, G, and T; any two of the following: A, C, G, T, and U; or U plus any three of the following: A, C, G, and T. Such subset combinations could additionally include or be substituted with any other natural or non-natural DNA or RNA nucleotide or nucleotide-like substance or analog with base-pairing properties. The stoichiometric ratio between any of these nucleotides in a population of molecules could be approximately 1:1 or any other ratio; herein such a sequence is referred to as "semi-degenerate". In certain embodiments, a "semi-degenerate" sequence refers to a set of two or more sequences, wherein the two or more sequences differ at at least one nucleotide position.

In embodiments, a semi-degenerate sequence is a sequence in which not every nucleotide is random with respect to its adjacent nucleotides (immediately adjacent or within two or more nucleotides). In embodiments, the term degenerate and semi-degenerate, as used herein, may have the same meaning as commonly understood by one of ordinary skill in the art to which this application belongs and as commonly used in the art to which this application belongs; such art is incorporated by reference in its entirety.

In embodiments, the sequences need not contain all possible bases at each position. The degenerate or semi-degenerate n-mer sequences may be generated by a polymerase-mediated method, or may be generated by preparing and annealing a library of individual oligonucleotides of known sequence. Alternatively, any degenerate or semi-degenerate n-mer sequences may be a randomly or non-randomly fragmented double stranded DNA molecule from any alternative source that differs from the target DNA source. In some embodiments, the alternative source is a genome or plasmid derived from bacteria, an organism other than that of the target DNA, or a combination of such alternative organisms or sources. Random or non-random fragmented DNA may be introduced into SMI adaptors to serve as variable tags. This may be accomplished through enzymatic ligation or any other method known in the art.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "one or more", "at least one", "more than one", and the like are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "about".

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting.

Unless otherwise defined, all technical and scientific terms used herein have the same meaning as commonly understood by one of ordinary skill in the art to which this application belongs and as commonly used in the art to which this application belongs; such art is incorporated by reference in its entirety.

Any of the above aspects and embodiments can be combined with any other aspect or embodiment as disclosed in the Summary, Drawings, and/or in the Detailed Description sections, including the below examples/embodiments.

SPECIFIC, NON-LIMITING, EXAMPLES/EMBODIMENTS OF THE PRESENT INVENTION

Disadvantages from Using Y-shaped Adapters for Duplex Sequencing

Duplex Sequencing with Y-shaped adapters is most readily performed with paired-end sequencing reads, as originally described (WO2013142389A1 and in Schmitt et al, PNAS 2012, each of which is incorporated herein by reference in its entirety). However not all sequencing platforms are compatible with paired end sequencing reads. When using previously-described Y- or loop-shaped adaptors where asymmetric primer sites are located in the single-stranded region opposite the adapter's ligateable end, Duplex Sequencing with single-end sequencing reads requires the sequencing read to fully extend through the DNA molecule. This is necessary to capture the SMI tag sequences at both ends of the molecule, which is required to able to distinguish sequencing reads from the two derivative strands. This requirement is illustrated as follows.

A previously-described Y-shaped Duplex Sequencing adaptor is shown in FIG. 1A. In FIG. 1A, features A and B represent different primer binding sites; α and α' represent a degenerate or semi-degenerate sequence and its reverse complement; β represents a different degenerate or semi-degenerate sequence; and α and β are two arbitrary sequences among a pool of degenerate or semi-degenerate sequences. Together, these serve as Single Molecule Identifiers (SMIs).

As originally described (e.g., WO2013142389A1), SMIs are used to distinguish individual molecules within a large pool. It is necessary to have a sufficiently large population of these encoded in the adapter library such that it is statistically unlikely that any two DNA molecules will be labeled with the same SMI sequences. Also, as previously described, the fragmentation sites introduced during library generation can be function as endogenous SMIs in certain situations, either independently, or in combination with a exogenous SMIs encoded in adapter sequences. In the present disclosure, only exogenous SMI domains are shown in examples of different adapter designs; however, it is understood (and included in the present invention) that exogenous SMI domains can be substituted with, or augmented by, DNA shear points acting as endogenous SMIs.

After adaptors are ligated to each end of a double-stranded DNA fragment from a library, the structure will appear shown in FIG. 1B. For clarity tracing derivatives in subsequent diagrams, the "left" and "right" ends of a particular DNA insert are noted as well as the "top" and "bottom" strands.

Following PCR, the double-stranded product derived from the "top" strand is shown in FIG. 1C. (L) and (R) indicate the respective "left" and "right" ends of the starting DNA molecule:

The double stranded PCR product derived from the "bottom" strand is shown in FIG. 1D.

The differing arrangements of α and β relative to A and B in the "top" strand and "bottom" strand products should be noted. With paired end sequencing reads (i.e., reading from both primer site A and B for each PCR product), it is possible to distinguish products derived from each strand because the α tag appears in the A read and β in the B read of one strand and the reciprocal case occurs in the other strand. See, FIG. 1E.

Use of paired-end reads, as described above, makes Duplex Sequence correction possible. However, with use of only single-end sequencing reads (i.e., only reading from primer site A or primer site B but not from both for a particular molecule), it is only possible to obtain Duplex Sequences if the sequencing reads are sufficiently long to capture the SMI sequences at both ends. If using sequencing primer A, full length sequencing reads (i.e., long enough to include both SMI sequences) derived from the different strands will yield the two sequences shown in FIG. 1F. Similarly, use of sequencing primer B with full length sequencing reads will produce the following two sequences shown in FIG. 1G. In both of the above cases, the "top" and bottom strand-derived products can be distinguished from each other by virtue of having SMIs in the opposite orientation (α-β in one and (β-α in the other). However, without sequencing reads that are long enough to capture both SMI sequences, Duplex Sequencing is not readily performed with single-ended sequencing. This is because the two sequencing reads do not each contain both the α and β tags. Another way of looking at this problem is that for parts of the ends of the DNA molecules, the complement may not be sequenced, such that there is no information about the second strand to make a comparison with.

To illustrate this, the two types of sequences produced when using a non-full length single ended sequencing reads from primer A are shown in FIG. 1H. Similarly, the corresponding sequences produced when using a non-full length single ended sequencing reads from primer B are shown in FIG. 1I. Note that for both of the sequencing reads shown in FIG. 1H and FIG. 1I, the "left" and "right" ends of each DNA fragment are only sequenced once with a given primer so Duplex Sequencing cannot be accomplished. That is because there is no opposite strand sequence to compare to. Thus, even if an amplified population of molecules were sequenced with each of the two different primers, there would be no information about the second strand which reveals that a particular set of read A and B sequences originated from the same derivative molecule.

The need for "read-through" of the full DNA molecule when using single-end sequencing can create technical challenges on some sequencing platforms where read-length is limited.

For Duplex Sequencing to be compatible with sub-full length sequencing reads with single-end sequencing, alternative adapter designs are necessary. In the absence of paired end sequencing reads and asymmetric primer sites on Y-shaped adapters, some other form of asymmetry must be introduced into adapted DNA molecules to be able to distinguish the strands. Examples of such design are disclosed below.

Introduction of Strand-Defining Asymmetry with a Non-Complementary "Bubble"

Figure 2A:
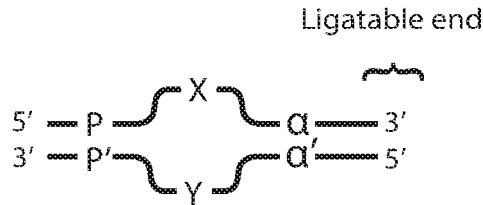
FIG. 2A to FIG. 2K illustrate Duplex Sequencing of the present invention using non-complementary "bubble" adaptors. Shown are an exemplary "bubble" adaptors (FIG. 2A and FIG. 2H to FIG. 2K), a double-stranded DNA molecule ligated to the adaptor of FIG. 2A (FIG. 2B), PCR products derived therefrom (FIG. 2C and FIG. 2D), and sequencing reads thus produced (FIG. 2E to FIG. 2G).

Disclosed in FIG. 2A is an exemplary design of a non-Y-shaped adapter (of the present invention) which allows Duplex Sequencing with non-paired end sequencing (i.e., a "bubble adapter"). Unlike previously-described Y-shaped adapters which have two primer sites, only a single primer site (P) with reverse complement (P') is present. α and its complement α' represent a degenerate or semi-degenerate Single Molecule Identifier (SMI) sequence; X and Y represent two halves of a Strand Defining Elements (SDE) which is a segment of non-complementary sequences which form an unpaired "bubble" in the middle of adjacent complementary sequences within the adapter. Finally, the adapter has a ligateable sequence. The asymmetry introduced by the SDE in this adapter design distinguishes sequencing reads derived from each strand as is illustrated in FIG. 2B to FIG. 2G.

Figure 2B:
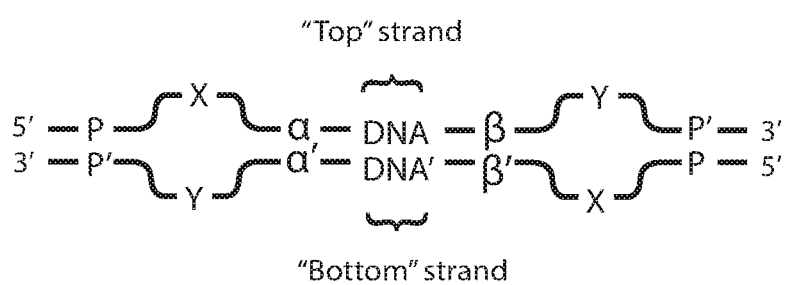

Following ligation of adapters similar to those shown in FIG. 2A to each end of a DNA fragment, the structure shown in FIG. 2B is produced. The second adapter is shown with SMI sequence β and β' to illustrate that the SMI sequence of the second ligated adapter is generally different from that of the first adapter. Alternately, an identical adapter may be ligated to both ends of a DNA molecule.

Figure 2C:
Figure 2D:

After PCR amplification, the double-stranded product derived from the "top" strand is shown in FIG. 2C and the double-stranded product derived from the "bottom" strand is shown in FIG. 2D.

Figure 2E:
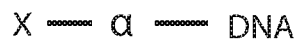
Figure 2E:
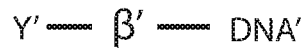
Figure 2F:
Figure 2F:
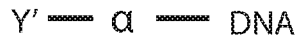

Because the primer site sequence is the same at both ends of the molecule in this example, two different types of sequence sequencing reads will be obtained from single-ended sequencing reads of the PCR product of each strand depending on which single-stranded half happens to be sequenced. The read derived from the "top" strand PCR product is shown in FIG. 2E and the read derived from the "bottom" strand PCR product is shown in FIG. 2F.

Figure 2G:
Figure 2G:
Figure 2G:
Figure 2G:
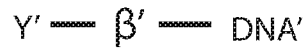

For analysis, as shown in FIG. 2G, sequencing reads are grouped by those containing a particular SMI, in this case either α or β. Sequences having arisen from a given single molecule of DNA can be grouped together by virtue of having the same SMI sequence. It is apparent that within each SMI group two types of sequences are seen: one is marked by SDE X and one by SDE Y. These define sequencing reads derived from opposite strands (i.e., "top" and "bottom"). For example, when sequences with SMI tag α are grouped together, the obtained sequences are X-α-DNA (FIG. 2E) and Y'-α-DNA (FIG. 2F). A consensus consisting of sequences arising from the "top" strand of the original DNA molecule can be made by grouping together the X-α-DNA sequences. Likewise, a consensus of the "bottom" strand can be made by grouping together the Y'-α-DNA sequences. Finally, a consensus of the two strands can be made by comparing together sequences arising from the two strands (i.e. those labeled sequence X will be compared with those labeled with sequence Y'). Together, these allow comparison as part of Duplex Sequencing analysis.

A similar outcome can be achieved by switching the order of the SMI and SDE sequences. One example of such an adapter is shown in FIG. 2H.

As articulated above and in WO2013142389A, in some embodiments, SMIs contained within the adapter sequences can be omitted in lieu of endogenous SMI sequences comprising the shear point sequences of the DNA molecule itself. The structure of one such adapter design would entail that shown FIG. 2A, but with exclusion of α and α'.

Figure 2H:
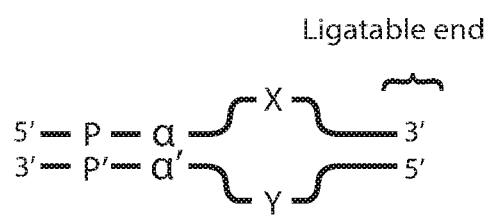
Figure 2I:
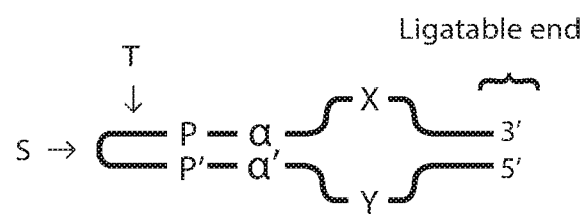

In some applications, the orientation shown in FIG. 2H is preferable. For example, in some sequencing platforms, such as those currently manufactured by Illumina®, a certain number of bases at the beginning of a sequencing run can be used for cluster identification and "invariant bases", that is, bases which are read as the same in all or in a substantial plurality of molecules being sequenced, can impact the efficiency of this process. A degenerate or semi-degenerate SMI sequence immediately at the beginning of the sequencing run may therefore be more desirable in this situation.

In other applications, the orientation shown in FIG. 2A is preferable. As described in the original description of Duplex Sequencing (i.e., WO2013142389A1), complementary double-stranded SMI sequences can most conveniently be produced by either primer extension with a polymerase across a single-stranded degenerate or semi-degenerate sequence or by individually synthesizing and annealing oligonucleotides containing different SMI sequences and then pooling these together to create a diverse adapter library. If the polymerase extension method is selected, having the SMI sequence on the ligation-domain end of the adaptor might be advantageous for facilitating the extension reaction. On certain sequencing platforms, such those manufactured by Ion Torrent™, a 3' overhang with modified bases at the non-ligateable end of the adaptor may not easily be compatible with synthesis by a polymerase; thus synthesis of an adapter by the polymerase extension approach is most readily performed with the SMI sequence located toward the ligateable end of the adapter, as shown in FIG. 2A.

As a specific example of how this approach would be brought into practice, consider the Ion Torrent™ sequencing platform, which can use the following pair of adaptors:

```
Adapter P1
                                              (SEQ ID NO: 1)
5' CCACTACGCCTCCGCTTTCCTCTCTATGGGCAGTCGGTGAT 3'

(SEQ ID NO: 2)
3' T*T*GGTGATGCGGAGGCGAAAGGAGAGATACCCGTCAGCCACTA
5'

Adapter A
                                              (SEQ ID NO: 3)
5' CCATCTCATCCCTGCGTGTCTCCGACTCAG 3'

(SEQ ID NO: 4)
3' T*T*GGTAGAGTAGGGACGCACAGAGGCTGAGTC 5'
```

Asterisks "*" represent phosphorothioate bonds.

The sequencing primer anneals to Adapter A, and thus sequence information is read out from the DNA fragment starting from the 3' end of Adapter A. Adapter A can be converted to a form applicable for the approach diagrammed in FIG. 2 with use of the following sequence:

```
                                              (SEQ ID NO: 5)
5'    CCATCTCATCCCTGCGTGTCTCCGACTCAG GCGC NNNN
G 3'

(SEQ ID NO: 6)
3' T*T*GGTAGAGTAGGGACGCACAGAGGCTGAGTC ATAT MMMM
C 5'
```

NNNN refers to a degenerate or semi-degenerate four-nucleotide sequence; MMMM refers to its complement; and a G-C base-pair is included downstream of the degenerate sequence to facilitate ligation, although other forms of ligation domains may be used.

In this illustration, adapter P1 and adapter A are both ligated to the target DNA molecule to be sequenced. For simplicity, the same adapter ligated to both ends of the DNA molecule can be ignored. However Ion Torrent™ adapters utilize a different adapter on each end of the molecule. Upon initial ligation, an individual DNA molecule may be ligated with adapters in various configurations, for example A-DNA-P1, A-DNA-A, or P1-DNA-P1. The correct configuration of A-DNA-P1 can be utilized for the sequencing reaction by virtue of being amplified in an emulsion PCR with primers directed against sites A and P1. Alternatively, other methods known in the art for selecting only molecules ligated to two different adapters can be used.

Upon amplification and sequencing, the following products will be obtained:

```
GCGC NNNN [DNA sequence]

TATA NNNN [DNA sequence]
```

Note that these correspond to products X-α-DNA and Y'-α-DNA as shown in FIG. 2G.

Products from the two strands can then be matched together for data processing via Duplex Sequencing as originally described (see, e.g., WO2013142389A1). Specifically, a consensus can be made from reads which begin with the sequence GCGC NNNN to obtain the consensus of the "top" strand. A separate consensus can be made from reads beginning with the sequence TATA NNNN to obtain the consensus of the "bottom" strand. The two Single-Strand Consensus Sequences can then be compared to obtain the Duplex Consensus Sequence of the starting DNA molecule. An alternative data processing approach is disclosed below; see, "Alternative data processing scheme for Duplex Sequencing".

The above approach enables Duplex Sequencing on platforms utilizing short reads which are not capable of paired-end reads, as in this embodiment, DNA sequence information is only needed from one of the two ends of the DNA fragment.

An alternate embodiment of this approach would be to introduce the asymmetry into the SMI sequence itself via use of a double-stranded, non-complementary or partially non-complementary SMI. While the SMI sequences themselves will not be complementary, products arising from the non-complementary SMI sequences could be determined to have arisen from the same starting double-stranded DNA molecule by virtue of having been pre-determined to form pairs.

As a specific example of this embodiment, consider a series of Ion Torrent™ "Adapter A" molecules having the following sequences:

```
Adapter 1:
                                              (SEQ ID NO: 7)
5'    CCATCTCATCCCTGCGTGTCTCCGACTCAG AAAT GCAGC
3'

(SEQ ID NO: 8)
3' T*T*GGTAGAGTAGGGACGCACAGAGGCTGAGTC GGGC CGTCG
5'

Adapter 2:
                                              (SEQ ID NO: 9)
5'    CCATCTCATCCCTGCGTGTCTCCGACTCAG ATAT GCAGC
3'
```

-continued (SEQ ID NO: 10)
3' T*T*GGTAGAGTAGGGACGCACAGAGGCTGAGTC GCGC CGTCG

5'

Adapter 3:

(SEQ ID NO: 11)
5'     CCATCTCATCCCTGCGTGTCTCCGACTCAG TATT GCAGC

3'

(SEQ ID NO: 12)
3' T*T*GGTAGAGTAGGGACGCACAGAGGCTGAGTC GGCC CGTCG

5'

Adapter 4:

(SEQ ID NO: 13)
5'     CCATCTCATCCCTGCGTGTCTCCGACTCAG ATTT GCAGC

3'

(SEQ ID NO: 14)
3' T*T*GGTAGAGTAGGGACGCACAGAGGCTGAGTC CGGG CGTCG

5'

For simplicity, only four adapters are listed above, although in practice it may be desirable to have a larger pool of such adapters. Note that, in this example, a complementary sequence is included downstream of the non-complementary sequence to form a double-stranded region that will facilitate ligation to the DNA molecule.

Individual DNA fragments are ligated to individual adapters, which results in asymmetric labeling of the two DNA strands. In particular, upon sequencing, the sequence of the "top strand" of the starting DNA molecule will be labeled with the sequence in the "top strand" of the adapter. The sequence of the "bottom strand" of the starting DNA molecule will be labeled with the reverse complement of the sequence in the "bottom strand" of the adapter.

As a particular example, the two DNA strands ligated to Adapter 1 will be labeled AAAT (top strand) and CCCG (bottom strand). Again, it should be noted that the bottom strand, upon sequencing, yields the reverse complement of the sequence initially present in the bottom strand of the adapter. Likewise, for sequences ligated to the other adapters, the molecular identifiers can be paired together by virtue of their paired tags. A computer program can then use a table of the known tag sequences from the adapters to assemble them into reads arising from complementary strands of single DNA molecules. Table 2 shows how the resultant sequence reads would be labeled based upon the specific non-complementary identifier sequences shown in the above example.

TABLE 2

| | First four nucleotides of sequencing read | |
|---|---|---|
| | Top strand | Bottom strand |
| Adapter 1 | AAAT | CCCG |
| Adapter 2 | ATAT | CGCG |
| Adapter 3 | TATT | CCGG |
| Adapter 4 | ATTT | GCCC |

These are only specific examples of particular embodiments. It will be apparent to one skilled in the art that SMI tags can be any arbitrary length, that SMI's can be completely random, or that consist entirely of pre-defined sequences. When an SMI sequence is in both strands of a double-stranded molecule, the two SMI sequences can be fully complementary (as described in the first instance mentioned example above), partially non-complementary, or entirely non-complementary. In some embodiments no exogenous molecular identifier tag is needed at all. In some cases, the randomly sheared ends of DNA molecules as unique identifiers can be used, so long as some sort of asymmetry (comprising an SDE) is present that allows one to distinguish products as arising from the two independent strands of a given single molecule of double-stranded DNA.

In any herein-disclosed aspect or embodiment of the present invention (and not limited to the currently-described embodiment), in both single-stranded and double-stranded SMIs, the set of SMI tags can be designed with an edit distance between distinct tags such that an error in synthesizing, amplifying, or sequencing the SMI sequence will not result in conversion of one SMI sequence to another (see, e.g., Shiroguchi et al, *Proc Nat Acad Sci USA*, 109(4):1347-1352). Incorporating an edit distance between SMI sequences allows SMI errors to be identified and removed, for example by using Hamming distance, Hamming codes, or another method of error correction that is known in the art. All SMIs from a set can be the same length; alternatively mixtures of SMIs of two or more different lengths can be employed within a set of SMIs. Using mixtures of SMI lengths can be advantageous for adapter designs that use an SMI sequence and additionally have one or more fixed bases at a site within or flanking the SMI, as utilizing more than one length of SMI within a set will cause the invariant base(s) to not all occur at the same read position during sequencing (see, e.g., Hummelen R et al, *PLoS One*, 5(8): e12078 (2010)). This approach can circumvent problems that may arise on sequencer platforms that may encounter sub-optimal performance (e.g., difficulty with cluster identification) in situations where invariant bases are present at a specific read position.

It will also be apparent to one skilled in the art that sequences that introduce asymmetry can be introduced anywhere within a sequencing adapter, including, for example, as an internal "bubble" sequence as shown above, before or after an SMI sequence, or within a single-stranded "tail" sequence in adapter designs that possess such a sequence. These sequences, as well as any associated SMI sequences, can be read directly as part of a sequencing read, or alternatively can be determined from an independent sequencing reaction (for example, in an index read). These sequences can moreover be used in conjunction with Y-shaped adapters, "loop" adapters, or any other adapter design known in the art.

Indeed, adaptors having different relative orientations of SMI sequences, SDE sequences, and primer binding sites are envisioned and included in the present invention.

The adaptor designs shown in FIG. 2A and FIG. 2H show the non-ligated end as being blunt-ended. However, this end can be overhung, recessed, or with a modified base or chemical group to prevent degradation or undesired ligation.

Additionally the two strands of the adapter can be connected to form a closed "loop", which may be desirable in some applications to prevent degradation or undesired ligation. See e.g., FIG. 2I. The closed "loop" linkage (marked at position "S") of FIG. 2I can be achieved by a conventional phosphodiester linkage or by any other natural or non-natural chemical linker group. This link may be chemically or enzymatically cleaved to achieve an "open" end before, during, or after ligation is carried out; cleaving the loop may be desirable prior to PCR amplification to prevent a rolling-circle-type amplicon. A non-standard base, such as a uracil, may be used here and before, during, or after adapter ligation, an enzymatic set of steps can be used to cleave the phosphodiester backbone. For example, in the case of uracil, using the combination of uracil DNA glycosylase to form an abasic site and endonuclease VIII to cleave the backbone would suffice. Alternatively, a bulky chemical group or other non-transversable modified base at this link site could be used to prevent a polymerase from traversing beyond the end of the loop and serve the same purpose.

In any herein-disclosed aspect or embodiment of the present invention (and not limited to the currently-described embodiment) for adapter designs that use a double-stranded SMI sequence, whether it is complementary, partially non-complementary, or fully non-complementary, a specific advantage of synthesizing the adapter as a linear molecule that is annealed into a "loop" form is that the "top" and "bottom" strand SMI sequences will be present at a 1:1 ratio within the molecule itself. This approach may be advantageous relative to annealing individual "top" and "bottom" oligonucleotide pairs to form double stranded SMIs, as in such an approach, if the concentration of oligonucleotide used for the "top" and "bottom" strands is not in a perfect 1:1 ratio, excess molecules of one adapter strand or the other may be present, and may be problematic to downstream steps (e.g., the additional single-stranded oligonucleotides may cause inappropriate priming during PCR amplification, or may anneal with other single-stranded oligonucleotides that might be present which could create adapter molecules wherein the two SMI strands are not appropriately paired).

It may in some instances be desirable to prevent replication of the full loop sequence itself, in which a modified sequence position can optionally be included as a replication block. This can be a base that can be enzymatically removed (e.g., uracil, which can be removed by uracil DNA glycosylase), or for example, a region which partially or fully inhibits DNA replication (e.g., an abasic site).

Alternatively or additionally, a restriction endonuclease site may be introduced (marked at position "T" in FIG. 2I) that could be used to achieve the "open" conformation, with resultant release of a small hairpin fragment.

Figure 2J:
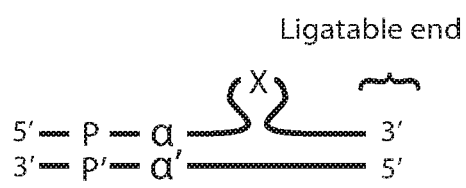
Figure 2K:
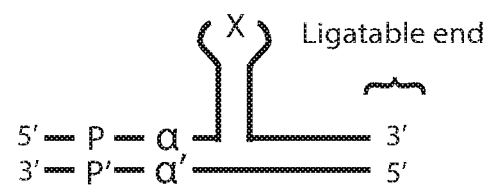

It is should be readily apparent that different arrangements of base asymmetry between the two adapter strands equally serve as a strand-defining element. A bubble can be formed in an adapter strand when there is insertion of one nucleotide or more than one nucleotide relative to the otherwise complementary strand is shown in the adapter of FIG. 2J. FIG. 2K shows an adapter where the more than one nucleotide insertion includes a portion that is self-complementary; this latter adapter offers similar functionality as a simple difference between the two strands involving one or more nucleotide positions.

Introduction of Strand-Defining Asymmetry Using a Non-Complementary SMI Sequence The adapter designs shown in FIGS. 2A to 2K contain two key features that enable tag-based Duplex Sequencing. One is a unique molecular identifier (i.e., an SMI) and the other is a means of introducing asymmetry in the two DNA strands (i.e., an SDE). In an initial description of Duplex Sequencing, Y-shaped adapters and paired-end sequencing reads were utilized. Introducing asymmetry in the two DNA strands was accomplished by virtue of the asymmetric tails themselves. A distinct and superior Duplex Sequencing adapter design, as shown in FIG. 3A, includes a non-complementary "bubble" shaped SMI which jointly serves as a molecular identifier as well as an asymmetry-introducing SDE.

In this design, P and P', respectively, represent a primer site and its complement and $\alpha i$ and $\alpha ii$ represent two degenerate or semi-degenerate sequences which are non-complementary for all or a portion of their length. The synthesis of this form of adapter is most readily accomplished by individually synthesizing and hybridizing pairs of oligonucleotides with different degenerate or semi-degenerate sequences prior to pooling two or more of these together to form a diverse pool. Because the oligonucleotides are individually synthesized and annealed, the relationship between a given $\alpha i$ and $\alpha ii$ sequence will be known and recorded in a database that can be searched for corresponding partner SMI sequences during post-sequencing analysis.

Following adaptor ligation to a double-stranded DNA fragment, the structure shown in FIG. 3B is produced. In this structure, $\beta i$ and $\beta ii$ a pair of non-complementary SMI sequences that are generally distinct from $\alpha i$ and $\alpha ii$, although the same adapter structure could be ligated to both ends.

After PCR amplification, the double-stranded product derived from the "top" strand is shown in FIG. 3C and the double-stranded product derived from the "bottom" strand is shown in FIG. 3D.

Because the primer site sequence is the same at both ends of the molecule (in this example), two different types of sequence reads will be obtained from single-ended sequencing reads of the PCR product of each strand and depending on which single-strand happens to be sequenced. The single-ended sequencing read from the "top" strand PCR product is shown in FIG. 3E and the single-ended sequencing read from the "bottom" strand is shown in FIG. 3F.

During analysis reads can then be grouped by specific SMI sequences and their corresponding non-complementary partner based on a relationship known from a database produced at the time of and in conjunction with SMI adaptor library synthesis. As shown in FIG. 3G, the paired "top" and "bottom" strand sequences of the original molecule are tagged with $\alpha i$ and $\alpha ii$ for the reads originating on one end of the molecule and $\beta i$ and $\beta ii$ for those on the opposite end.

Introduction of Strand-Defining Asymmetry Using Modified or Non-Standard Nucleotides Another way strand asymmetry can be introduced into a Duplex Sequencing adaptor is by a nucleotide or nucleotide analog which initially forms a paired strand DNA, but then results in a mismatch following a further biochemical step. One example of this is a DNA polymerase mis-incorporation. The mis-incorporation can occur during amplification, either inherently, or after conversion to a mismatched region via a chemical or enzymatic step.

For some applications, this form of SDE may be preferable to the "bubble type" sequences, disclosed above, since they avoid problems that may arise from free single-stranded regions, e.g., mis-annealing to other DNA oligonucleotides and exonuclease/endonuclease degradation.

Many non-standard nucleotides known in the art can serve this purpose. Non-limiting examples of such modified nucleotides include tetrahydrofuran; 8-oxo-7,8-dihydro-2'-deoxyadenosine (8-oxo-A); 8-oxo-7,8-dihydro-2'-deoxyguanosine (8-oxo-G); deoxyinosine; 5'-nitroindole; 5-Hydroxymethyl-2'-deoxycytidine; iso-cytosine; 5'-methyl-isocytosine; and iso-guanosine, and others known in the art.

An 8-oxo-G-containing Duplex Sequencing adapter is shown in FIG. 4A. The 8-oxo base is paired opposite to a complementary cytosine base and no bubble is formed. As with examples above and that follow, the relative order of the SMI sequence (in this case α) and the SDE site (in this case the 8-oxo-G site) can be switched as needed. P and P' represent a primer site and its complement.

Following adaptor ligation to a double-stranded DNA fragment, the structure shown in FIG. 4B is produced.

Treatment of double-stranded DNA of FIG. 4B with a glycosylase, such as oxoguanine glycosylase (OGG1), can then be performed (potentially in conjunction with a DNA ligase to repair the resultant nick that may occur with glycosylases which possess lyase activity). This treatment will result in an intact phosphodiester DNA backbone with introduction of an abasic site, as shown in FIG. 4C. Each of the two strands can then be copied, for example, with a polymerase. Under appropriate reaction conditions, certain thermostable polymerases preferentially insert A opposite abasic sites (Belousova E A et al, *Biochim Biophys Acta* 2006), resulting in a G→T mutation. The reciprocal strand, in contrast, retains the C nucleotide that was present in the adaptor at the time of ligation. This treatment leads to strand asymmetry that allows products of the two strands to be distinguished.

During PCR or other forms of DNA amplification, under certain conditions with particular polymerases, adenine will be preferentially inserted opposite the abasic when the strand is copied. With subsequent rounds of copying this adenine will be paired to a thymine, ultimately leading to replacement of the original 8-oxo-G site with a T. Moreover, treatment with a glycosylase is not mandatory. Under appropriate reaction conditions, polymerases can insert A opposite 8-oxo-G without the shown abasic intermediate (Sikorsky J A et al *Biochem Biophys Res Commun* 2007). In either case, after PCR amplification, the double-stranded product derived from the "top" strand will be as shown in FIG. 4D and the double-stranded product derived from the "bottom" strand will be as shown in FIG. 4E.

Because the primer site sequence is the same at both ends of the molecule in this (non-limiting) example, two different types of sequence reads will be obtained from single-ended sequencing reads of the PCR product of each strand depending on which single-strand happens to be sequenced. Those PCR products derived from the "top" strand PCR product will be as shown in FIG. 4F and those PCR products derived from the "bottom" strand will be as shown in FIG. 4G.

During analysis, sequencing reads can be grouped by those containing a particular SMI, in this case α or β. See, FIG. 4H. The T and G marked products within each SMI grouping define the strand of origin and allow Duplex Sequence comparison.

It will also be apparent to one skilled in the art that a modified nucleotide or another analog, as described above, may be placed anywhere within a sequencing adapter, so long as the sequence obtained from the modified nucleotide or the other analog can be recovered at the time of DNA sequencing.

It will be apparent to one skilled in the art that many other nucleotide analogs can be utilized to fulfill the same purpose. Other examples include tetrahydrofuran and 8-oxo-7, 8-dihydro-2'-deoxyadenosine (8-oxo-A). Any nucleotide modification which can inherently result in mis-incorporation of a different nucleotide by a DNA polymerase or which can be converted into a mis-coding lesion or a mismatched base by an enzymatic or chemical step or spontaneously with time can be used in adapters of this embodiment.

Moreover, a non-nucleotide molecule can be incorporated to asymmetrically label the two strands. For example, biotin can be incorporated into one of the two adapter strands, which would facilitate separate analysis of the two strands by utilizing streptavidin to physically separate biotin-containing strands from strands which lack biotin. This embodiment is disclosed in detail below.

Using Combinations of Duplex Sequencing Adapter Designs to Introduce Different Primer Sites on Opposite Ends of DNA Molecules The preceding examples of non-Y-shaped adapters show symmetric ligation of the same type of adaptor to both ends of DNA molecules. Currently, most sequencing platforms require that adapted DNA molecules have different primer sites on either end, for example, to allow cluster amplification on either surfaces or beads. For sequencing platforms that do not routinely use Y-shaped adapters to create these different primer sites (for example Ion Torrent™ (Thermo® Inc), SOLiD (Applied Biosystems® Inc.), and 454 (Roche® Inc.)) a mixture of two different adapters are ligated and then molecules containing one of each primer site are selected; most commonly through a bead-based emulsion PCR process.

Illustrated below is one simple approach for generating asymmetric primer sites using non-Y-shaped Duplex Sequencing adapters.

For this, a mixture of one Duplex Adapter and one standard adapter is produced in which each adapter contains a different PCR primer site. The Duplex Adapter may be any design described herein above or below or as known in the art.

An exemplary Duplex Adapter is shown in FIG. 5A, which has a primer site P with complement P' followed by an SDE comprised of mismatched sequences X and Y, each comprising one or more nucleotides, followed by a degenerate or semi-degenerate SMI sequence α. The other adapter, shown in FIG. 5B is a "standard" adapter which contains a different primer site O with complement O'.

Following ligation of this adapter mix to a DNA library, three different types of products are produced, as shown in FIG. 5C to FIG. 5E. On average, half of successfully adapted molecules will carry a different adapter sequence on each end (FIG. 5C), one-quarter will have two Duplex Adapters (FIG. 5D), and one-quarter will have two standard adapters (FIG. 5E). Under appropriate selection conditions, only molecules with one primer site P and one primer site O will cluster amplify. Thus, the latter two (non-useful) types of products can be ignored going forward, and are not shown in subsequent descriptions.

After PCR amplification, the double-stranded product derived from the "top" strand will be as shown in FIG. 5F and the double-stranded product derived from the "bottom" strand will be as shown in FIG. 5G.

Sequencing from primer site P will yield the following sequences that derive from the "top" and "bottom" strands. These can be distinguished by virtue of carrying either an SDE X or Y label. See, FIG. 5H.

It is readily apparent that any other form of non-Y-shaped Duplex Adaptor described herein or as known in the art could serve the same purpose as that used in this embodiment. For example, instead of one Duplex Adapter and one standard adapter, it is possible to use two Duplex Adapters carrying different primer sites. After ligation and PCR, the amplified product could be split and one portion sequenced with primer P and the other sequenced with primer O. This would enable Duplex Sequencing both ends of each adapted molecule. Because reads from different primer sites are not actually paired-end, they cannot readily be related together for any particular molecule. However, for applications where DNA to be sequenced is of very limited quantity, additional sequence information obtained from Duplex Sequencing of both ends of molecules may still be advantageous.

Use of Two Reads on Non-Paired-End Platforms Can Maximize Read Length During Duplex Sequencing Paired-end sequencing, such as that carried out on Illuminag® instruments, generally requires that a sequencing platform be able to sequence one strand from a primer site on one end of an adapter DNA molecule and then generates the reverse complement strand prior to sequencing the other end of the molecule from a different primer site. A technical challenge of this includes the process of complementary strand generation, which is a reason why not all platforms are easily compatible with this paired end sequencing.

However, the ability to sequence two different portions of an adapted DNA molecule can be accomplished, to a limited extent, without the need to generate a complementary strand. This may be accomplished by using a second primer site contained within a second adapter attached at the opposite end of the DNA molecule relative to the first adapter such that that sequencing read progresses away from the DNA molecule and the first adapter, thereby producing a sequencing read of the second adapter itself. In some situations such ability might be desirable. For example, because the SMI and SDE sequences required for Duplex Sequencing consume a portion of the inherently limited read-length that can be achieved, being able to move these elements to the opposite adapter to be read during a second shorter read could be helpful when maximum read length is required. A similar benefit could be realized by relocating the index barcode sequences often used for sample multiplexing.

To enable this process, two different adapters may be used. The first, as shown in FIG. 6A, contains a simple primer site P opposite its complement P'.

The other adapter sequence, as shown in FIG. 6B, contains features necessary for Duplex Sequencing without Y-shaped tails: an SMI and an SDE. This Duplex Adapter can be any of the designs described herein and in which the SMI and SDE are separate sequence elements, combined into the same sequence element as an unpaired SMI, or where the SDE is comprised of a modified base.

In the example shown in FIG. 6B, the SDE entails mismatched sequences X and Y adjacent to a degenerate or semi-degenerate SMI sequence α. PCR primer site O with complement O' is on the non-ligated end of the adapter. Unique to this adapter design is a second primer site P2 with complement P2' that is adjacent to the ligateable end but oriented such that an annealed primer will extend into the adapter molecule itself rather than toward the DNA fragment.

Figure 6C:
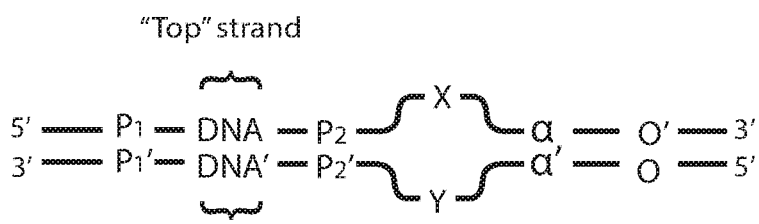

Following ligation of this adapter mix to a DNA library, three different products are produced. Those with two of the same adapter types on opposite ends can be ignored because only the product with one of each adapter (containing both primer sites P and O, as shown in FIG. 6C) will be successfully cluster amplified and sequenced.

Figure 6D:
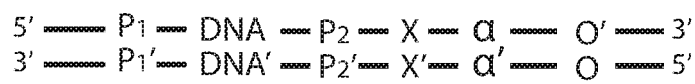
Figure 6E:
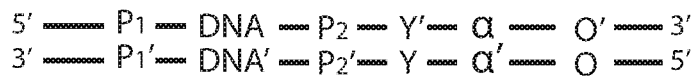

After PCR amplification the double-stranded product derived from the "top" strand will be as shown in FIG. 6D and the double-stranded product derived from the "bottom" strand will be as shown in FIG. 6E.

Figure 6F:
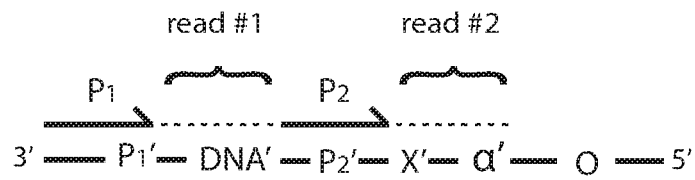
Figure 6G:
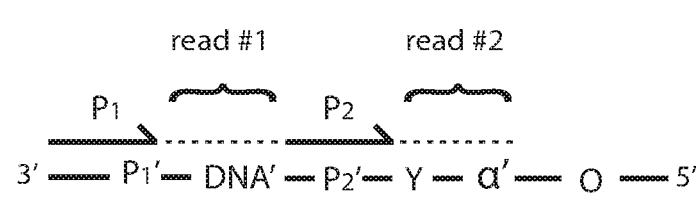

Shown below are the orientations of annealed sequencing primers P1 and P2 and regions that can be sequenced by each. These reads would most conveniently be sequenced with one before the other. This would be accomplished by introducing one sequencing primer and undergoing a first sequencing read; then, introducing the second after the first sequencing read is completed. If "read #2" (as shown in FIG. 6F and FIG. 6G) is carried out first, the sequencing could be run until the end of the molecule was reached and would self-terminate sequencing. If "read #1" is carried out first, it would be necessary to abort this sequencing reaction before adding primer P2 to begin the "read #2". This could be accomplished by either introduction of modified dNTPs which are not further extendable after incorporation or by melting the strand synthesized during the initial sequencing reaction away from the template strand, either thermally or chemically, and washing it away prior to adding the next sequencing primer.

The arrangement for the sequencing template strand derived from the "top" strand is as shown in FIG. 6F and the arrangement for the sequencing template strand derived from the "bottom" strand is as shown in FIG. 6G.

The sequencing reads from the "top" strand-derived template will be as shown in FIG. 6H and the sequencing reads from the "bottom" strand-derived template will be as shown in FIG. 6I.

It is readily apparent that the sequencing read pairs from the different original strand molecules are distinguishable by virtue of carrying either an SDE X label or SDE Y label.

Use of Two Reads on Non-Paired-End Platforms Maximizes Tag Diversity for Duplex Sequencing The potential advantages stemming from use of the above-disclosed form of double reading extends beyond simply conserving read length. In the original description of tag-based Duplex Sequencing with Y-shaped adapters, one SMI sequence was appended to each end of the adapted DNA molecule. This design has a practical advantage in certain situations for efficiently generating a sufficiently large population of diverse SMI-containing adapters to ensure every DNA molecule can be uniquely labeled.

As an illustration, if a fully degenerate four-nucleotide SMI sequence is introduced into the original Y-shaped adapter design and ligated to a DNA fragment library (as shown in FIG. 1B) and sequenced with paired end reads, the total number of possible ways a molecule could be labeled is $4^4*4^4=65,536$. If a fully degenerate 8 base pair SMI sequence were incorporated into a Duplex Adaptor and ligated to a DNA library for single end reading (as shown in FIG. 5C), the same 65,536 labeling combinations could be achieved. When generating complementary SMI tags with a polymerase extension method, these two means of achieving 65,536 labels would be equally feasible, however this is not the case when generating adaptor pools with individually-synthesized oligonucleotides. In the first scenario, a total of $4^4 \times 2=512$ oligonucleotides would need to be produced. In the latter scenario, $4^8 \times 2=131,072$ would need to be produced and individually annealed; this would greatly increase the financial cost and efforts required.

For some embodiments of Duplex Sequencing, the oligonucleotide synthesis method of SMI adapter production is preferable and a sufficiently diverse SMI-containing adapter population might not be practically achievable with only a single SMI on one end of a molecule, such as disclosed above.

The above-described method of double reading on non-paired end compatible platforms could be used to overcome this limitation by allowing an SMI sequence to be included in both adapters for sequencing in two steps of the same reaction. This is illustrated below.

For this, two types of adapters are needed, each bearing a different amplification primer site. At least one must contain an SDE and, in examples, both will contain a degenerate or semi-degenerate SMI sequence. As shown in FIG. 7A, the first adapter is similar to the adapter of FIG. 6A except it additionally includes an SMI sequence (here identified as "β"). The second adapter, as shown in FIG. 7B, is similar to the adapter shown in FIG. 6B and contains an SMI sequence (here, identified as "α").

It will be obvious to one experienced in the art that the relative arrangements of the SMI and SDE features of the two adapters can be interchanged to achieve the same outcome. The SDE shown above in the latter adapter could be placed in the former instead. Any form of SDE or SMI described previously could be substituted with equivalent effect for those used in this example.

Following ligation of this adapter mix to a DNA library, the product successfully bound to one of each adapter type will as shown in FIG. 7C.

After PCR amplification, the double-stranded product derived from the "top" strand will be as shown in FIG. 7D and the double-stranded product derived from the "bottom" strand will be as shown in FIG. 7E.

As described in the previous embodiment, the orientation of sequencing primer sites P1 and P2 and regions sequenced by each for the "top" strand are as shown in FIG. 7F and for the bottom strand are as shown in FIG. 7G.

The reads from the "top" strand-derived template will be as shown in FIG. 7H and the reads derived from the "bottom" stand-derived template will be as shown in FIG. 7I.

Again, the products of the two strands are readily distinguishable by virtue of their differing X and Y SDE labels. For Duplex Sequencing analysis, the sequences of SMI α and SMI β can be combined into a single identifying tag sequence.

Asymmetric SMIs in Y-shaped Duplex Sequencing Adapters

Several currently-available sequencing platforms require different primer sites on the opposite ends of DNA molecules to allow cluster amplification and sequencing. This can be accomplished with Y or bubble-shaped adapters with asymmetric primer binding sites or through the two adapter ligation method illustrated in the immediately previous three embodiments. Y-shaped adapters have been most commonly used on paired end sequencing-compatible platforms, such as those manufactured by Illumina®; however, they could be used on other platforms.

One general advantage of Y or "bubble-shaped" adapters for library preparation is that, theoretically, every double-adapted DNA molecules will be capable of being sequenced. However, with methods that use two different adaptors, only half of molecules produced will be capable of being sequenced they have one of each adaptor type whereas the other half of molecules produced will have two copies of the same adapter. In certain situations, e.g., where input DNA is limiting, a higher conversion of Y-shaped adapters may be desirable.

However, as illustrated in first embodiment described above (the originally-described Duplex Sequencing method), without the ability to do paired end-reads or complete read-throughs, originally-described Y-shaped Duplex Adapters do not readily allow Duplex Sequencing with single ended-reads.

However, use of a sequencing primer site in the complementary "stem" sequence of the Y-shaped adaptors allows single-ended reads for Duplex Sequencing, but only if an asymmetry is introduced by at least one SDE elsewhere in the adaptor sequence. A brief illustration follows.

In FIG. 8A, a Y-shaped adapter is shown which contains an unpaired SMI comprising sequences αi and αii. This sequence in this design will also serve as an SDE. Three primer sites are present: A and B, which are PCR primers on the free tails, and C (and C') which includes a sequencing primer site (and its complement).

Following adapter ligation to a DNA fragment the structure shown in FIG. 8B is produced in which two adapters with two distinct non-complementary SMIs are affixed to either end.

After PCR amplification using primers complementary to sites A and B, the double-stranded product derived from the "top" strand will be as shown in FIG. 8C and the double-stranded PCR product derived from the "bottom" strand will be as shown in FIG. 8D.

After sequencing from primer site C, two different types of sequencing reads will be obtained from single-ended reads of the PCR product of each strand depending on which single-stranded half happens to be sequenced. The sequencing reads from the "top" strand PCR product are as shown in FIG. 8E and the sequencing reads derived from the "bottom" strand PCR product are as shown in FIG. 8F.

During analysis, sequencing reads can be grouped by specific SMI sequences and their corresponding non-complementary partner based on a relationship known from a database produced at the time of and in conjunction with SMI adaptor library synthesis. In this, as shown in FIG. 8G, the paired "top" and "bottom" strand sequences of the original molecule are tagged with αi and αii for the reads originating on one end of the molecule and βi and βii for those on the opposite end.

Duplex sequence analysis can therefore be carried out. The analysis is analogous to that described above in the embodiment entitled "Introduction of strand-defining asymmetry using a non-complementary SMI sequence".

An alternate design, as exemplified in FIG. 8H, for this type of Y-shaped adapter includes a closed loop which is advantageous to prevent exonuclease digestion or potentially non-specific ligation to the free arms of the Y as well as "daisy chaining" of the free arms. A closed "loop" linkage (marked by an arrow) can be achieved by a conventional phosphodiester linkage or by any other natural or non-natural chemical linker group. This link could be chemically or enzymatically cleavable to achieve an "open" end after ligation has been carried out, such as would often be desirable prior to PCR amplification to prevent a rolling-circle-type amplicon. Alternatively, a bulky chemical group or modified nucleotide at this link site could be used to prevent a polymerase from traversing beyond the end of the loop and serve the same purpose. Alternatively, as exemplified in FIG. 8I, a restriction endonuclease recognition site is introduced at a hairpin complementarity region within the loop (marked by an arrow); this could be used to achieve the "open" conformation, with resultant release of a small hairpin fragment.

In some situations, it is preferable not to be required to perform additional enzymatic steps after adapter ligation prior to PCR. An adapter design, as exemplified in FIG. 8J, in which the tails of the adapters are complementary, yet not covalently connected may still overcome problems caused by free unpaired DNA tails, in the absence of need for additional steps.

Asymmetric SMIs in Y-Shaped Duplex Sequencing Adapters

Another variation on the concept of unpaired SMIs in Y-shaped or loop-shaped adapters, includes these unpaired SMIs located in the free single-stranded tail regions between PCR primer sites and a complementary stem. One advantage of this design is that it allows the SMIs to be completely sequenced as part of "dual-indexing" reads, such as are available on select Illumina® sequencing systems (Kircher et al (2012) *Nucleic Acid Res.* Vol. 40, No. 1, e3). Not having SMIs included in the main sequencing read would maximize read-length of a DNA insert for applications where long reads are particularly desirable. An example follows.

FIG. 9A shows a Y-shaped Duplex-Sequencing adapter containing unpaired PCR primer sites A and B. $\alpha i$ and $\alpha ii$ represent a pair of at least partially non-complementary degenerate or semi-degenerate SMIs. P and P' is a sequencing primer site and its complement.

Following adapter ligation to a DNA fragment the structure shown in FIG. 9B is produced whereby two adapters with two at least partially non-complementary SMIs are affixed to either end.

After PCR amplification using primers complementary to sites A and B, the double-stranded product derived from the "top" strand will be as shown in FIG. 9C and the double-stranded product derived from the "bottom" strand will be as shown in FIG. 9D.

On the Illumina® platform, as an example, when using paired-end sequencing with dual-indexing, after completing one sequencing read and one indexing read, the complementary strand may be generated and the corresponding sequencing and index read of the other strand may be carried out.

However, it should be noted that neither paired end sequencing nor dual indexing as techniques allows Duplex Sequencing by itself. While both single-strands of a given PCR product are effectively sequenced together, each PCR product derives from only one of the two strands of an original DNA duplex, and thus, sequencing both strands of a PCR product does not equate to sequencing both strands of an original DNA duplex.

A possible relative orientation of a sequencing primer and an indexing primer and the regions they sequence is shown in FIG. 9E for reads in both directions from the PCR product derived from the "top" strand and shown in FIG. 9F for reads in both directions from the PCR product derived from the "bottom" strand.

It would also suffice to sequence both the SMI and the sequence itself in a single sequencing read rather than in two separate reads. It is apparent that many different configurations and numbers of primers can be utilized to sequence the SMI and the read sequence. In some embodiments, such as nanopore sequencing, sequencing of the SMI and/or DNA sequence might not require specific primer sites at all. Moreover, while this example describes use of PCR, this and other embodiments can be amplified by any other method known in the art, including rolling circle amplification and other approaches. See, Kircher et al (2012).

When comparing the different pattern of sequences in all four reads with regard to those derived from the "top" and "bottom" strands (as shown in FIG. 9G), it is apparent that they can be distinguished from each other because one carries the SMI tags $\alpha i'$ and $\beta i$ and the other carries tags $\alpha ii$ and $\beta ii'$. Although the two strands do not share any tags in common in this non-limiting example, they can still be related to each other because the relationship between $\alpha i$ and $\alpha ii$ and between $\beta i$ and $\beta ii$ is known from when the adapters were prepared and can thus be looked up from a database as a component of analysis.

Use of a Single Circular Vector to Introduce Primer Sites, an SMI and an SDE for Duplex Sequencing Illustrated in FIG. 10 is an alternate structure that introduces all elements necessary for Duplex Sequencing in a single molecule rather than two paired adapters.

In this embodiment, a circular structure is formed by attaching the two ends of a linear double-stranded molecule (comprising the elements necessary for Duplex Sequencing) with the two ends of a DNA fragment with compatible ligation sites.

In FIG. 10A, A/A' and BB' represent two different primer sites and their reverse complement; $\alpha$ and $\alpha'$ entails a degenerate or semi-degenerate SMI sequence; and X and Y are respective non-complementary halves of an SDE.

After ligation of a double-stranded DNA fragment into the double-stranded molecule of FIG. 10A, a closed loop is produced, as shown in FIG. 10B.

After generating the ligated product of FIG. 10B, amplification is carried out from the primer sites using PCR. Alternatively, rolling circle amplification could be carried out first. Selective destruction of unligated library and adapters may be advantageous and accomplished with a 5'-3' or 3'-5' exonuclease. The circular design uniquely offers these opportunities, which are not readily possible with many other designs.

It will be readily apparent that any of the forms of SMIs and SDEs described above and below could be substituted for those shown or the order of them rearranged.

As an example of another embodiment, as shown in FIG. 10C, a single element near one ligation site that serves as both an SMI and SDE, such as discussed in the embodiment entitled "Introduction of strand-defining asymmetry using a non-complementary SMI sequence" could be used.

Alternatively, as shown in FIG. 10D and FIG. 10E, an SDE and SMI could be designed into the sequences near each of the adapter ligation sites to facilitate paired end sequencing.

In this design it should be noted that it is not mandatory for the SMI sequences on opposite strands to be complementary (as shown in FIG. 10E), so long as the relationship between the corresponding sequences (i.e. $\alpha i$ and $\alpha ii$) are known and can be looked up in a database during analysis.

Duplex Sequencing Through Asymmetric Chemical Labeling and Strand Isolation

As discussed above, Duplex Sequencing fundamentally relies on sequencing both strands of a DNA duplex in a way that they can be distinguished. In an originally-described embodiment of Duplex Sequencing (in WO2013142389A1), both strands could be linked together with a hairpin sequence to sequence paired strands together. WO2013142389A1, as well as in the multiple embodiments disclosed-above, describes ways in which two strands of a unique DNA duplex can be distinguished using DNA tagging. This latter approach involves labeling each DNA molecule with a unique DNA sequence (an endogenous SMI comprising the coordinates of one or both ends of a DNA fragment or an exogenous SMI comprising a degenerate or semi-degenerate sequence) and introducing strand-defining asymmetry through at least one form of an SDE (e.g., an asymmetric primer sites with paired end-reading, a "bubble" sequence, a non-complementary SMI sequence, and a non-standard nucleotide which either naturally or chemically is converted to a mismatch).

Below is disclosed another approach for carrying out Duplex Sequencing which includes asymmetric chemical labeling of the two strands in a duplex such that they can be physically separated for sequencing in independent reactions. One example of this follows.

As shown in FIG. 11A, two different adapters are used. The first adapter contains primer site P with complement P' and an SMI sequence $\alpha$ with complement $\alpha'$. One strand of the first adapter additionally carries a chemical tag that is capable of binding or being bound by known substance, e.g., a solid surface, a bead, a fixed structure, and a binding partner, in a way that the other DNA strand is not. As shown in FIG. 11A, the chemical tag is biotin, which has a binding partner of and affinity for streptavidin.

Other binding partner pairs known in the art may be used, preferably in the form of a small molecule, a peptide or any other uniquely bindeable moiety. This label could also be in the form of a nucleic acid sequence (e.g., DNA, RNA, or a combination thereof and a modified nucleic acid such as peptide-nucleic acids or locked nucleic acid), preferably in single-stranded form, where a substantially complementary "bait" sequence affixed to a solid substrate (e.g., a solid surface, a bead, or a similar other fixed structure) could be used to bind to, and selectively capture and isolate one strand of the adapter-ligated molecule from the other.

The second adapter does not carry a chemical tag in this non-limiting example. As shown in FIG. 11B, the second adapter bears a different primer site O with complement O'.

After the adapters of FIG. 11A and FIG. 11B are ligated to a DNA fragment the (preferred) structure shown in FIG. 11C is produced.

In addition, two other types of structures will be produced: one that has two primer site P containing adapters and another that is ligated to two primer site O containing adapters. As discussed above in the embodiment entitled "Using combinations of Duplex Sequencing adapter designs to introduce different primer sites on opposite ends of DNA molecules", enrichment for the preferred structure over the other two types of structures can be routinely achieved with specific amplification conditions prior to sequencing, such that the other two types of structures can be ignored.

As shown in FIG. 11D, following ligation, the DNA strands can be thermally or chemically melted apart and then the strand bearing the chemical tag with a selective affinity for a particular binding partner (in this case streptavidin, for example bound to paramagnetic beads) can be separated from the other strand. The two, now separated, strands can be independently sequenced, optionally with a preceding step in which the two separated strands are independently amplified (sequencing can occur in physically different reactions or in the same reaction after applying different indexes to each, for example with labeled PCR primers and recombining).

Alternately, both strands may be labeled with different chemical tags with affinities for two different types of baits. Tags found in one sequencing reaction or index group can then be compared to corresponding tags in the other population and Duplex Sequencing analysis carried out. In this example, an SDE is still used, but it entails an asymmetrically-affixed chemical tag that can be used to physically separate the strands. Their physically-different compartmentalization allows the two strands to either be sequenced individually or undergo a subsequent differential labeling step (e.g., PCR with primers carrying different index sequences on their tails) prior to pooling and combined sequencing that can later be informatically-deconvolved.

Another embodiment of this concept would be to use labels (i.e., physical groups) with other properties that allow strand separation by means other than chemical affinity. As examples, a nucleic acid strand comprising a molecule with a strong positive charge (e.g., a physical group having a charge property) could be preferentially separated from its paired unlabeled paired strand through application of an electric field (e.g., by electrophoresis) or a nucleic acid strand comprising a molecule with a strong magnetic capacity (e.g., a physical group having a magnetic property) could be preferentially separated from its paired unlabeled paired strand through application of a magnetic field. A nucleic acid strand comprising a chemical group that is sensitive to precipitation (e.g., a physical group having an insolubility property) could be preferentially separated from is paired unlabeled paired strand when in solution under certain applied conditions, such that DNA itself is soluble, but DNA comprising the physical group is insoluble.

Yet another variation on the concept of physical separation of paired strands after an SMI is applied (either as an exogenous tag within a ligated adapter sequencer or as an endogenous SMI comprising the unique shear points of the DNA fragment) is to use dilution following thermal or chemical melting of DNA duplexes into their component single-strands. Instead of applying a purifiable chemical label to one strand to separate it from the other, the single-strands are diluted into multiple (i.e., two or more) physically-separated reaction chambers such that the probability of the two originally paired strands sharing the same container is small. For example, if the mixture were split among one hundred containers, by random chance, only about 1% of partner strands would be placed in the same container. Containers could entail a set of physical vessels, such as containers, test tubes, or wells in a microwell plate, or physically separated, non-communicating droplets, for example an aqueous-in-hydrophobic phase emulsion. Any other method may be used in which the contents of two or more spatially-distinct volumes of a fluid or a solid which contains nucleic acid molecules are prevented from substantially intermixing the nucleic acid molecules. In each container, PCR amplification could be carried out, preferably using primers carrying a different tag sequence in each. This unique tag sequence added by the different primer in every container would most conveniently be situated where it could be recorded during a sequencing index read (e.g., see FIG. 9E). These labels would serve as an SDE. In this example, approximately 99% of the partner strands carrying the same SMI label would be assigned a different SDE label than their partner strand. Only about 1% would be assigned the same label. Duplex Sequencing analysis and consensus-making could proceed as usual using the SMI and these SDEs. In the small number of cases where partner strands acquire the same SDE by chance, these molecules will inherently be ignored during Duplex Analysis and will not contribute false mutations.

Introducing an SDE During Nick Translation

In some settings, such as in commercially available kits used for adapter ligation for the Ion Torrent™ platform, double-stranded adapters are ligated to a double-stranded target DNA molecule that is to be sequenced. However, here, only one of the two strands of the target DNA molecule is ligated to the adapter. A common embodiment of this is when the 5' strand of the ligation domain is non-phosphorylated. A polymerase with strand displacement activity is then used to copy the sequence from the ligated strand onto the unligated strand, in a process commonly known as "nick translation". If the adapter designs disclosed herein are used this way and without modification, in many cases the SDE would be lost during the nick-translation step; thereby, preventing Duplex Sequencing. This is exemplified below.

Figure 12A:
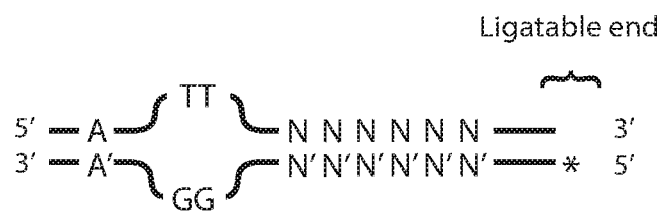
Figure 12B:
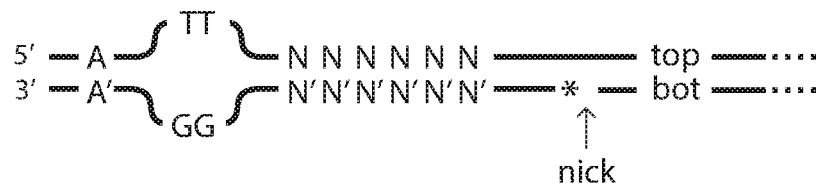

Shown in FIG. 12A, is one type of Duplex Sequencing adapter. N's represent degenerate or semi-degenerate SMI sequence; TT opposite GG is a non complementary SDE region; and the asterisk represents a non-ligateable, dephosphorylated 5' base:

After ligation of the adapter of FIG. 12A to a double-stranded DNA molecule, one unligated nick remains as shown in FIG. 12B.

Figure 12C:
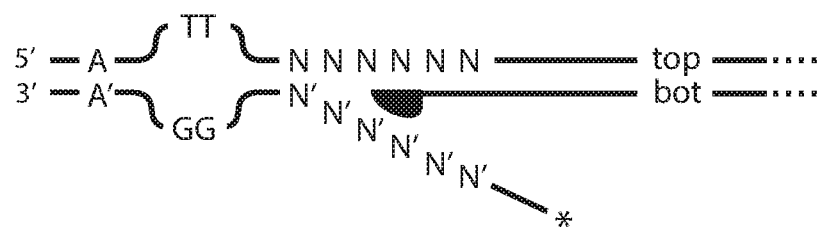
Figure 12D:
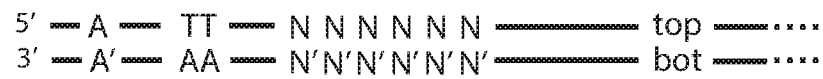
Figure 12E:
Figure 12F:
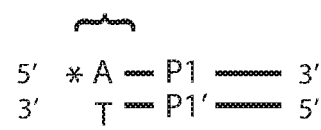

With standard "nick-translation" approaches, a strand-displacing polymerase is used to extend the 3' end of the library DNA molecule and displaces the unligated strand of the adapter. This is shown in FIG. 12C. After extension, the non-complementary SDE is lost as shown in FIG. 12D. When the SDE is lost, Duplex Sequencing cannot occur because the strands are indistinguishable.

One approach to allow use of the nick-translation method of adapter ligation and which retains the SDE is as follows.

Shown in FIG. 12E is an example of an Ion Torrent™ adapter "A" that has been modified to include a degenerate or semi-degenerate SMI sequence. Note that no SDE is present. "A" is the primer site. Asterisk represents non-phosphorylated 5' base. Shown in FIG. 12F is an example of an Ion Torrent™ P1 primer. P1 represents primer site. Asterisk indicates a dephosphorylated 5' base.

Figure 12G:

After ligation of each adapter of FIG. 12E and FIG. 12F to a double-stranded DNA, the structure of FIG. 12G is formed. Products with two P1 or two A primer sites are not shown, as they will not cluster amplify. For clarity, the non-ligated adapter strands are not shown either.

Figure 12H:
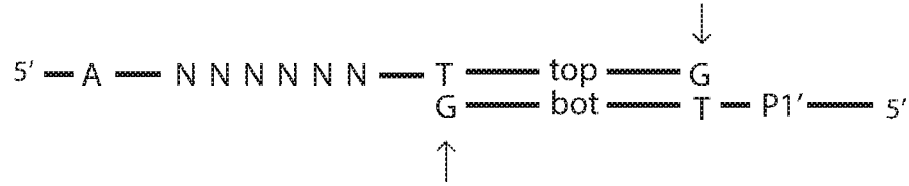
Figure 12I:
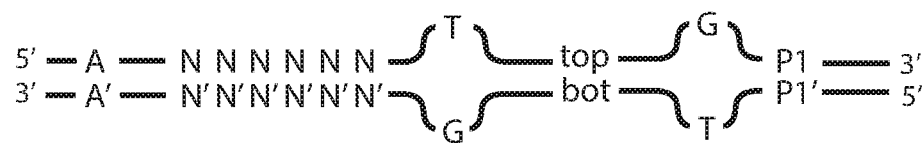

Next, a strand-displacing polymerase is added as per the typical nick translation protocol (e.g., Bst polymerase, as used in some commercial kits, due to its strong strand-displacement activity). However, as shown in FIG. 12H, only one of the four dNTPs is initially added, in this example dGTP, and thus a T-dGTP mis-incorporation will occur (of note, this mis-incorporation event can be made to occur with a number of DNA polymerases under appropriate reaction conditions; see, e.g., McCulloch and Kunkel, *Cell Research* 18:148-161(2008) and the references cited therein).

While mismatch incorporation can be fairly efficient under certain conditions, mismatch extension and creation of a second mismatch is fairly inefficient (McCulloch and Kunkel, 2008). Thus, with appropriate conditions, nucleotide incorporation will cease after the mismatch occurs. At this time, the remaining three dNTPs can be added such that the polymerase has access to all four dNTPs. The remainder of the adapter sequence will be copied to form the structure shown in FIG. 12I, which has a non-complementary position such that amplification products of the "top" strand will be distinguishable from amplification products of the "bottom" strand.

Figure 12J:
Figure 12K:
Figure 12L:
Figure 12M:

After PCR the product arising from the original "top" strand will be as shown in FIG. 12J and the PCR the product arising from the original "bottom" strand will be as shown in FIG. 12K.

Sequencing of the "top" strand product will yield the structure shown in FIG. 12L and sequencing of the "bottom" strand product will yield the structure shown in FIG. 12M.

Note that the sequencing products are can be distinguished from each other on the basis of the introduced mismatch.

A specific example of reducing this concept to practice with Ion Torrent™ adapters is shown below.

Ion Torrent™ adapters can use the following sequences:

Adapter P1

(SEQ ID NO: 15)
5'      CCACTACGCCTCCGCTTTCCTCTCTATGGGCAGTCGGTGAT
3'

(SEQ ID NO: 16)
3'  T*T*GGTGATGCGGAGGCGAAAGGAGAGATACCCGTCAGCCACTA
5'

Adapter A (SEQ ID NO: 17)
5'      CCATCTCATCCCTGCGTGTCTCCGACTCAG 3'

(SEQ ID NO: 18)
3'  T*T*GGTAGAGTAGGGACGCACAGAGGCTGAGTC 5'

The asterisk "*" represents a phosphorothioate bond.

The sequence of Adapter A could be modified as follows. NNNN indicates a degenerate or semi-degenerate SMI sequence (four nucleotides are shown, but the length of this sequence is arbitrary), and MMMM indicates the complement of the NNNN. As previously described, Duplex Sequencing can be performed without SMI sequences but an SMI is shown here as a specific example of applying the concept with double-stranded molecular tagging.

Modified adapter A (SEQ ID NO: 19)
5'      CCATCTCATCCCTGCGTGTCTCCGACTCAG NNNN AAC 3'

(SEQ ID NO: 20)
3'  T*T*GGTAGAGTAGGGACGCACAGAGGCTGAGTC MMMM TTG 5'

Adapters A and P1 are attached to opposite ends of a DNA molecule to be sequenced. For simplicity, only the adapter A end of the molecule is shown, and also for simplicity, the two strands are shown as X's and Y's, respectively. Any DNA sequence of any length could be used, as long as the length of the sequenced fragment is compatible with the sequencing process being used.

The "top" strand is ligated, but the "bottom" strand is not ligated, leaving a nick (shown as |)

(SEQ ID NO: 21)
5'      CCATCTCATCCCTGCGTGTCTCCGACTCAGNNNNAACXXXXXX
XXX 3'

(SEQ ID NO: 22)
3'  T*T*GGTAGAGTAGGGACGCACAGAGGCTGAGTCMMMMTTG|YYYYY
YYYY 5'

A strand-displacing polymerase is added along with dGTP. G is incorporated at the first position encountered in the 5'-3' direction (correct incorporation of G opposite C), as well as at the second position encountered (incorrect incorporation of G opposite A). Because extension of an incorrect base after a mismatch is inefficient, under appropriate conditions of polymerase concentration, reaction time, and buffer conditions, the polymerase stalls and further incorporation does not occur. Note that the first two nucleotides of the "bottom" adapter strand are displaced during this reaction, and are shown below the adapter-DNA construct in the schematic below. Newly incorporated bases are indicated in bold.

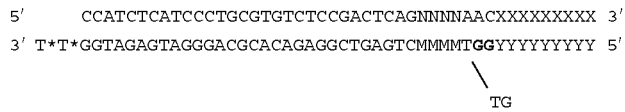

(Top: SEQ ID NO: 23 and Bottom: SEQ ID NO: 24)

Now, dCTP, dATP, and dTTP are added to the reaction, such that all four nucleotides are available to the polymerase. Strand-displacement synthesis can proceed, with an intermediate product shown below for illustration purposes:

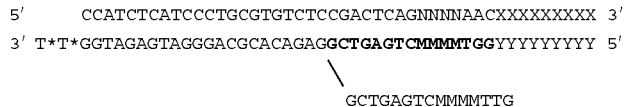

(Top: SEQ ID NO: 25, Middle: SEQ ID NO: 26, and Bottom: SEQ ID NO: 27)

After the end of the template is reached, the original "bottom" strand of the adapter is fully displaced (not shown) and a fully synthesized "bottom" strand is present with a single base pair that is not complementary (A:G basepair, underlined)

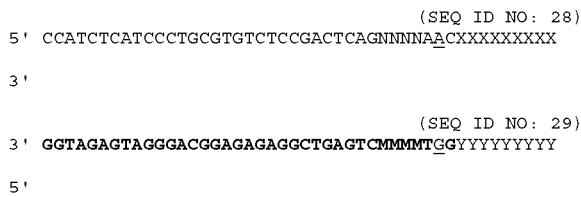

This construct can then be used for PCR amplification and sequencing per typical Ion Torrent™ protocols. Of note, PCR amplification results in products from both the "top" and "bottom" strand, and these products can be distinguished from one another by virtue of the non-complementary base pair introduced during nick translation.

Products arising from the "top" strand will be of the following form (position of base mismatch is underlined):

(SEQ ID NO: 30)

Products arising from the "bottom" strand, in contrast, will be of the following form (position of base mismatch is underlined):

(SEQ ID NO: 31)

Note that the "bottom" strand product is the reverse-complement of the sequence initially present in the "bottom" strand of the adapter-ligated DNA (and thus, the G nucleotide, which was the base mis-insertion introduced during nick-translation, is read out during sequencing as a C nucleotide).

Now, amplification duplicates arising from each of the two strands can be compared to one another for error correction. "Top strand" products arising from a given molecule of double-stranded DNA will have tag sequence NNNNAAC. "Bottom" strand products, in contrast, will have tag sequence NNNNACC. Thus duplicates from the two strands can be resolved for purposes of error correction, as previously described (Schmitt et al, PNAS 2012).

Introducing a Mismatch After Nick Translation

An alternative approach to the above would be to complete nick translation with all four nucleotides present, and then to change a base in the template strand to a different base.

An adapter containing a primer sequence and its complement (P/P'), a U-A base pair (U=uracil), and a single-stranded SMI sequence and its complement (α/α') is shown in FIG. 13A; the asterisk represents a dephosphorylated 5' end.

After the adapter of FIG. 13A is ligated to a double-stranded DNA molecule to be sequenced a single stranded nick remains at the dephosphorylated site, as shown in FIG. 13B. Here, the "top" strand ligates by virtue of the 5' phosphate in the target DNA molecule, but the "bottom" strand does not ligate to the target DNA due to the lack of a 5' phosphate in the adapter, leaving the nick.

Strand displacement synthesis can be performed with a polymerase (e.g., Bst polymerase) and all four dNTPs, resulting in the structure shown in FIG. 13C.

The resulting extended product now re-appears as it did in the original adapter. As shown in FIG. 13D, no site of asymmetry is yet present.

A purification step can be performed to remove the polymerase and dNTPs. The uracil can then be removed from the "top" strand (of the structure shown in FIG. 13D) by adding uracil DNA glycosylase and an appropriate AP endonuclease, resulting in a single nucleotide gap as shown in FIG. 13E.

Next, a non-strand-displacing polymerase is added (e.g., sulfolobus DNA polymerase IV, which is highly error-prone and facilitates base mis-incorporation) along with a single nucleotide, e.g., dGTP but no other nucleotides. In this example, this would result in mis-incorporation of G opposite A. The resultant nick could be sealed with DNA ligase, resulting in a product with a mismatch in the adapter as shown in FIG. 13F.

As shown in FIG. 13G, after amplification and sequencing, the products arising from the "top" strand are distinguishable from those arising from the "bottom" strand by virtue of having either a G or T base on sequencing reads carrying the same SMI sequence.

This example is illustrated with creation of a G-A mismatch but it will be apparent that any other mismatch of one or more bases, at any position in the molecule, would have the same effect A specific example of applying this concept on the Ion Torrent™ platform is shown below.

Consider the following "Modified adapter A" with additions to the standard sequence in bold (U=uracil):

```
                                            (SEQ ID NO: 32)
5'     CCATCTCATCCCTGCGTGTCTCCGACTCAG U NNNN C 3'

(SEQ ID NO: 33)
3' T*T*GGTAGAGTAGGGACGCACAGAGGCTGAGTC A MMMM G 5'
```

The adapter is ligated to a target DNA molecule as above, with the location of the nick shown as a "|":

```
                                            (SEQ ID NO: 34)
5'     CCATCTCATCCCTGCGTGTCTCCGACTCAGUNNNNCXXXXXXX
XX 3'

(SEQ ID NO: 35)
3' T*T*GGTAGAGTAGGGACGCACAGAGGCTGAGTCAMMMMG|YYYYYY
YYY 5'
```

Now, a strand displacement polymerase is used in the presence of all four dNTPs to allow full strand displacement of the "bottom strand" of the adapter (newly incorporated bases are in bold, original bottom adapter strand is displaced and is not shown):

```
                                            (SEQ ID NO: 36)
5' CCATCTCATCCCTGCGTGTCTCCGACTCAGUNNNNCXXXXXXXXX
3'

(SEQ ID NO: 37)
3' GGTAGAGTAGGGACGCACAGAGGCTGAGTCAMMMMGYYYYYYYYY
5'
```

The product is purified to remove dNTPs, then uracil DNA glycosylase and an AP endonuclease are added to remove the uracil from the "top" strand, leaving a single nucleotide gap:

```
                                            (SEQ ID NO: 38)
5' CCATCTCATCCCTGCGTGTCTCCGACTCAG NNNNCXXXXXXXXX
3'

(SEQ ID NO: 39)
3' GGTAGAGTAGGGACGCACAGAGGCTGAGTCAMMMMGYYYYYYYYY
5'
```

Next, a non-strand-displacing error-prone polymerase (e.g., sulfolobus DNA polymerase IV) is added along with dGTP, which results in incorporation of G opposite A at the single nucleotide gap; ligase can then be added to result in an intact adapter-DNA product on the "top" strand. This results in a non-complementary base-pair (location underlined).

```
                                            (SEQ ID NO: 40)
5' CCATCTCATCCCTGCGTGTCTCCGACTCAGGNNNNCXXXXXXXXX
3'

(SEQ ID NO: 41)
3' GGTAGAGTAGGGACGCACAGAGGCTGAGTCAMMMMGYYYYYYYYY
5'
```

This product can be used for error correction with a method analogous to that described in the immediately preceding embodiment.

Introducing a Mismatch After Nick Translation

The embodiment entitled "Introducing an SDE during nick translation" showed how an asymmetric SDE can be introduced during nick-translation within an adapter sequence. The same principle could be applied to a DNA molecule library itself such that an asymmetric site (an SDE) is incorporated into library molecules, possibly even before an adapter is added. This can be achieved a variety of ways. The following is merely one example.

A double-stranded DNA molecule with a "top" and "bottom" strand is shown in FIG. 14A. DNA molecules can be fragmented a variety of ways for library preparation. Some DNA sources, such as cell-free DNA in plasma, are already in small pieces and no separate fragmentation step is needed. Acoustic shearing is an often used method. Semi-random enzymatic shearing methods can be used. Non-random endonucleases that cut at defined recognition sites are another method. In this example, an endonuclease that leaves a 5' overhang is used to create a library of similarly 5' overhung fragments, as shown in FIG. 14B.

This asymmetric state can be converted into a sequence asymmetry by using a polymerase in the presence of only a single nucleotide that is not complementary to the first nucleotide to be copied by the polymerase. In this example dGTP is used which will lead to an T-dGTP mis-incorporation (such mis-incorporations can be made to occur with a number of DNA polymerases under appropriate reaction conditions; see McCulloch and Kunkel, Cell Research 18:148-161(2008) and the references cited therein). A partially double-stranded DNA molecule including two mismatches is shown in FIG. 14C.

Next the all four nucleotides are added to the reaction and copying continues to extend the end of the DNA molecule until the DNA molecule is double-stranded. A mismatch bubble is produced on each fragment end, forming two SDEs as shown in FIG. 14D.

Duplex Sequencing adapters can then be ligated to the DNA molecule. The exemplary adapters shown in FIG. 14E have primer site P with complement P', a different primer site O with complement O', and a degenerate or semi-degenerate SMI α with complement α'.

Ligation is carried out between the double-stranded DNA molecule of FIG. 14D and the adapters of FIG. 14E to produce the structure of FIG. 14F. As discussed in previous embodiments, products that are ligated to two of the same adapter sequences can be ignored, as under appropriate conditions they will not amplify.

After PCR the product derived from the "top" strand is as shown in FIG. 14G and the product derived from the "bottom" strand is as shown in FIG. 14H.

Sequencing using primer P will lead to the following sequences from the respective strands shown in FIG. 14I.

Note that the presence of a C vs. a T following the SMI sequence allows "top" strand reads to be distinguished from those derived from the "bottom" strand.

Similar SDE labeling could similarly be achieved with use of mutagenic nucleotide analogs to fill in the 3' recessed end gaps or other methods.

Other shearing methods could be used and 3' recessed ends created with an exonuclease prior to filling in in a way that creates an SDE.

In broad terms, this example illustrates that an SDE can be introduced in a way that is independent of adapters themselves. For Duplex Sequencing to occur, only some form of an SMI and an SDE in each final adapted molecule allows the sequences derived from each strand of a Duplex to be related back to each other, yet also definitively distinguished from each other. These elements come in a variety of forms, as considered above, and can be introduced before, during, or after adapter ligation.

Variations on Assembling Molecules Appropriate for Duplex Sequencing

The embodiments disclosed above illustrate improved methods for Duplex Sequencing, wherein a final molecule that is assembled comprises at least one strand-defining element (SDE) and at least one single molecule identifier (SMI) sequence; both of the SDE and SMI are attached to a double-stranded or partially double-stranded molecule of DNA that is to be sequenced. However, the SMI and SDE do not need to be included in a single adapter; they simply need to be present in the final molecule, ideally prior to or during any amplification and/or sequencing step.

For example, an SDE can be created in an adapter after ligation via an enzymatic reaction, as shown in FIG. 4D. Similarly, as originally-described (in WO2013142389A1), in some embodiments, the specific sequences at the shear points of individual DNA library fragments can serve as an endogenous SMI sequence, without need for addition of an exogenous SMI included within an adapter. "Shear points" can be considered as the mapping coordinates of either end of a DNA fragment, when the fragment is aligned to a reference genome. The coordinates of either one end, or both ends, can be used as an "endogenous SMI" to distinguish distinct DNA molecules from one another, either alone, or in combination with the sequences of one or more exogenous SMI sequences.

The following list includes non-limiting variants of such adapters:

The SDE is present in both strands, but the SMI and primer binding site are present in only one adapter strand. These elements are then copied to the other strand with a polymerase.

No SDE is present; the SMI and primer binding site are in only one strand. A polymerase is used with only one incorrect dNTP present to create an SDE, and then the remaining dNTPs are added to allow the polymerase to make the SMI and primer binding sites double stranded.

A ligation domain is only present in one adapter strand (such that the second adapter strand is not attached). A new second adapter strand is then copied from the first adapter strand with a polymerase. This creates the SMI and primer binding domain. As above, only one incorrect dNTP is added initially to create an SDE; then, the remaining dNTPs are added. This approach is shown in an above-disclosed embodiment.

A ligation domain is only present in one adapter strand (such that the second adapter strand is not attached); this adapter strand includes a uracil. A new second adapter strand is then copied from the first adapter strand with a polymerase with all four nucleotides present. Then, the uracil base in the original adapter strand is enzymatically removed with uracil DNA glycosylase and an appropriate AP endonuclease. Then, a DNA polymerase is used with a single incorrect nucleotide present to insert a mismatch into the gap in the DNA, and then the gap is ligated with DNA ligase. This approach is shown in more detail in the embodiment disclosed above which relates to FIG. 4.

A first attached adapter has SMI domains alone in both strands. A second adapter is then attached to this, which has the primer binding domain and SDE, also in both strands.

A first attached adapter has SMI and SDE domains in both strands. A second adapter is attached which has a primer binding domain in both strands.

A first attached adapter has SMI domains in both strands. A second "Y adapter" is then attached which has two non-complementary or partially non-complementary primer binding domains.

A first attached adapter has an SMI in both strands, as well as a single-stranded region, with a ligation domain as well. An oligonucleotide is annealed and ligated into the single-stranded region; a mismatch is included within the oligonucleotide which creates an SDE domain.

In other embodiments, the location of the bubble can be changed, the length of the n-mer can be altered, an n-mer can be eliminated altogether with duplicates from each strand identified instead from the shear points at the ends of DNA molecules. Variant nucleotide or nucleotide-like molecules can be used within the DNA (e.g., locked nucleic acids (LNAs) and peptide nucleic acids (PNAs), and RNA).

Each of the variants disclosed herein are included in the present invention.

In each of these variants, the same general concept applies: the final molecule for Duplex Sequencing comprises the core elements of a SDE and an SMI connected to a segment of DNA that is to be sequenced. Also note that the same general concept applies to the original description of Duplex Sequencing (in WO2013142389A1), wherein Duplex Sequencing is performed with an adapter comprising two asymmetric primer binding sites (e.g., in a "Y" configuration), which serve as the SDE in this case, and an SMI sequence attached to a double-stranded DNA molecule. These components can be assembled onto a target DNA molecule in a variety of ways, so long as the requisite components are present in the final molecule, ideally prior to or during any amplification or sequencing step.

Alternative Data Processing Scheme for Duplex Sequencing

Duplex Sequencing can be performed by obtaining a "consensus" of amplified duplicates arising from each of the two individual DNA strands to obtain two single-strand consensus sequences, then comparing the resultant single-strand consensuses to obtain a Duplex consensus sequence. This approach of "averaging" the sequence of amplified duplicates of a single molecule, position-by-position, may not be desirable in some settings (e.g., if recurrent amplification errors might occur at a given position in heavily damaged DNA) and more reliable results could thus be obtained in some settings with a different data processing scheme.

Alternate approaches include the following:

Among molecules with a given tag sequence corresponding to the "top" and "bottom" strands, arbitrarily pick one "top" strand and one "bottom" strand, and compare the sequence of the two strands. Keep positions at which both strands agree; mark disagreeing positions as undefined. Call the resulting sequence read a Duplex read.

Repeat this process for arbitrarily selected "top" and "bottom" strands sharing the same tag sequence to obtain a series of "Duplex reads".

Among the resultant "Duplex reads" with a given tag sequence, select the Duplex read with, for example, the fewest sequence changes relative to the reference sequence, and/or the fewest undefined positions within the read. This read can then be considered the read most likely to represent the true sequence of the starting DNA duplex.

In one embodiment, such an approach could be specifically enabled with the algorithm described below. It is understood that this is only a single example for the purposes of illustration, and many other algorithms could be used to form duplex consensus reads. Moreover the example is shown for a specific embodiment of Duplex Sequencing, but similar examples could be prepared appropriate for many other embodiments of Duplex Sequencing.

The following steps may be used in an embodiment disclosed herein which uses a "bubble" sequence to result in "top" strands of each duplex being labeled GCGC, and "bottom" strands being labeled TATA, with both strands sharing the same single molecule identifier (SMI) sequence.
1. Prepare a file containing all sequencing reads from the experiment;
2. Split the file into two files: one file called "GCGC" containing reads labeled GCGC, and a second file called "TATA" containing reads labeled TATA;
3. Pick an arbitrary read in the "GCGC" file, read its SMI tag, and search for a matching SMI tag in the "TATA" file;
4. If a match is found: create a new sequence from these two sequences. In the new sequence, maintain all sequence positions within the reads that agree, and mark all disagreeing positions among the two reads as being undefined. Write this new sequence to a file called "duplexes", and remove the two sequences from the "GCGC" and "TATA" files If a match is not found: remove the sequence from the "GCGC" file and write it to a file called "unmatched";
5. Pick another arbitrary read from the "GCGC" file, and carry out steps 3 to 4 again; and
6. Continue until no reads remain in the "GCGC" file.

Within the resultant "duplexes" file, consider all reads that have a matching SMI tag sequence. In some cases, there may be multiple "duplex" reads that have the same SMI tag (these may be due to, for example, multiple PCR duplicates of a single starting DNA molecule). These can be converted to a single duplex read by any of the following approaches:

Among these reads, select the read with the fewest mismatches relative to the reference genome sequence and discard the remaining reads.

Alternatively, select the read with the fewest undefined positions relative to the reference genome sequence and discard the remaining reads.

Alternatively, create a consensus among reads that have a shared SMI tag sequence to create duplex consensus reads.

It will be apparent to one skilled in the art that combinations of the above options can be used to develop duplex consensus reads, or that several other methods not described above could be used.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of sequencing a double-stranded target nucleic acid molecule comprising the steps of:
    (1) ligating a pair of adapter nucleic acid sequences to at least one terminus of a double-stranded target nucleic acid molecule, thereby forming a double-stranded adapter-target nucleic acid molecule comprising a first strand adapter-target nucleic acid sequence and a second strand adapter-target nucleic acid sequence, wherein
        the first strand adapter-target nucleic acid sequence has a first single molecule identifier (SMI) domain and the second strand adapter-target nucleic acid sequence has a second SMI domain relatable to the first SMI domain;
    (2) denaturing the double-stranded adapter-target nucleic acid molecule to obtain single strands of each of the first and second strand adapter-target nucleic acid sequences;
    (3) physically separating the single strand of the first strand adapter-target nucleic acid sequence and the single strand of the second strand adapter-target nucleic acid sequence into physically-separated reaction chambers;
    wherein physically separating in step (3) comprises separating the single strand of the first strand adapter-target nucleic acid sequence and the single strand of the second strand adapter-target nucleic acid sequence by dilution;
    (4) amplifying in the physically-separated reaction chambers:
        the first strand adapter-target nucleic acid sequence, thereby producing a first set of amplified products comprising a plurality of first strand adapter-target nucleic acid molecules and a plurality of first strand complementary molecules, and
        the second strand adapter-target nucleic acid sequence, thereby producing a second set of amplified products comprising a plurality of second strand adapter-target nucleic acid molecules and a plurality of second strand complementary molecules;
    (5) relating the second set of amplified products to the first set of amplified products by the first and second SMI domains;
    (6) distinguishing the second set of amplified products from the first set of amplified products by the physical separation of the first strand adapter-target nucleic acid sequence from the second strand adapter-target nucleic acid sequence prior to amplification;
    (7) sequencing the first set of amplified products;
    (8) sequencing the second set of amplified products; and
    (9) comparing at least one sequence obtained from the first set of amplified products with at least one sequence obtained from the second set of amplified products to generate a consensus sequence of the double-stranded target nucleic acid molecule.

2. The method of claim 1, wherein the double-stranded adapter-target nucleic acid molecule comprises a non-nucleotide molecule or affinity label capable of being bound by an affinity partner, the non-nucleotide molecule or affinity label being present on one strand of the double-stranded adapter-target nucleic acid molecule, and wherein step (3) comprises separating the first strand adapter nucleic acid sequence from the second strand adapter nucleic acid sequence using the affinity partner to capture the strand comprising the non-nucleotide molecule or affinity label.

3. The method of claim 2, wherein the non-nucleotide molecule or affinity label is selected from the group comprising Colicin E2, Im2, glutathione, glutathione-s-transferase (GST), Nickel, poly-histidine, FLAG-tag, myc-tag, or biotin.

4. The method of claim 2, wherein the non-nucleotide molecule or affinity label is selected from a small molecule, a nucleic acid, a peptide, and a uniquely bindeable moiety which is capable of being bound by the affinity partner.

5. The method of claim 4, wherein the affinity label comprises a nucleic acid, and wherein the nucleic acid includes DNA, RNA, or a combination thereof, and optionally, comprising a peptide-nucleic acid or a locked nucleic acid.

6. The method of claim 1, wherein either the first strand adapter-target nucleic acid sequence or the second strand adapter-target nucleic acid sequence comprises a physical group having a magnetic property, a charge property, or an insolubility property.

7. The method of claim 6, wherein the physical group has a magnetic property, and wherein step (3) comprises applying a magnetic field to the first and second strand adapter-target nucleic acid sequences to separate the said adapter-target nucleic acid sequence having the magnetic property from the other adapter-target nucleic acid sequence.

8. The method of claim 6, wherein the physical group has a charge property, and wherein step (3) comprises applying an electric field to the first and second strand adapter-target nucleic acid sequences to separate the said adapter-target nucleic acid sequence having the charge property from the other adapter-target nucleic acid sequence.

9. The method of claim 6, wherein the physical group has an insolubility property, and wherein step (3) comprises precipitating the said adapter-target nucleic acid sequence comprising the physical group to separate the first and second strand adapter-target nucleic acid sequences.

10. The method of claim 1, wherein step (4) includes amplifying the first and second strand adapter-target nucleic acid sequences through use of a primer specific to a portion of the sequence of the target nucleic acid molecule.

11. The method of claim 1, wherein step (1) includes ligating a first pair of adapter nucleic acid sequences to a first terminus and a second pair of adapter nucleic acid sequences to a second terminus of the double-stranded target nucleic acid molecule such that the double-stranded adapter-target nucleic acid molecule has a first related set of first and second SMI domains and a second related set of first and second SMI domains, and wherein the first related set of first and second SMI domains differs from the second related set of first and second SMI domains.

12. The method of claim 11, wherein the first pair of adapter nucleic acid sequences and the second pair of adapter nucleic acid sequences each include at least partially complementary primer binding domains.

13. The method of claim 11, wherein the first pair of adapter nucleic acid sequences has a first set of at least partially complementary primer binding domains and the second pair of adapter nucleic acid sequences has a second set of at least partially complementary primer binding domains, and wherein step (4) includes amplifying the first and second strand adapter-target nucleic acid sequences through use of a first primer pair specific to the first set of at least partially complementary primer binding domains and a second primer pair specific to the second set of at least partially complementary primer binding domains.

14. The method of claim 1, wherein sequencing the first set of amplified products includes generating a first strand consensus sequence and sequencing the second set of amplified products includes generating a second strand consensus sequence, and wherein the comparing step comprises comparing the first strand consensus sequence with the second strand consensus sequence to generate a consensus sequence of the double-stranded target nucleic acid molecule, and wherein a difference between the first strand consensus sequence and the second strand consensus sequence is considered an artifact.

15. The method of claim 1, wherein step (9) includes providing an error-corrected consensus sequence of the double-stranded target nucleic acid molecule by identifying the particular positions in both strands of the double-stranded target nucleic acid molecule that are not complementary, and wherein the method further comprises at least one of removing the identified particular positions or marking the identified particular positions as undefined.

16. The method of claim 1, wherein each of the first and second SMI domains comprises at least one degenerate or semi-degenerate nucleic acid sequence.

17. The method of claim 1, wherein the pair of adapter nucleic acid sequences comprises the first and second SMI domains.

18. The method of claim 1, wherein each of the first and second SMI domains is an endogenous SMI domain.

19. The method of claim 1, wherein each of the first and second SMI domains is an exogenous SMI domain, an endogenous SMI domain or a combination thereof.

20. The method of claim 1, wherein each of the first and second SMI domains comprise a first exogenous SMI sequence and a second endogenous SMI sequence, and wherein the second set of amplified products is related to the first set of amplified products by the first exogenous SMI sequence, the second endogenous SMI sequence, or a combination thereof.

21. A method of generating a high accuracy sequence read of a double-stranded target nucleic acid molecule comprising:
ligating a double-stranded adapter to at least one terminus of a double-stranded target nucleic acid molecule, thereby forming a double-stranded adapter-target nucleic acid complex comprising a first strand sequence and a second strand sequence, wherein—
the double-stranded adapter comprises a primer binding domain having a first strand primer binding sequence and a second strand primer binding sequence that is at least partially complementary to the first strand primer binding sequence, and
the double-stranded adapter-target nucleic acid complex has a single molecule identifier (SMI);
melting the first strand sequence from the second strand sequence to obtain single-stranded first and second strand sequences;
physically separating the single-stranded first strand sequence and the single-stranded second strand sequence into physically-separated reaction chambers;
wherein physically separating comprises separating the single-stranded first sequence and the single-stranded second sequence by dilution;
amplifying in the physically-separated reaction chamber the first strand sequence through use of a primer specific to the first strand primer binding sequence, thereby producing a first set of amplified products comprising a plurality of first strand molecules and a plurality of first strand complementary molecules;
amplifying in the other physically-separated reaction chamber the second strand sequence through use of a primer specific to the second strand primer binding sequence, thereby producing a second set of amplified products comprising a plurality of second strand adapter-target nucleic acid molecules and a plurality of second strand complementary molecules;
relating the second set of amplified products to the first set of amplified products by the SMI and distinguishing the second set of amplified products from the first set of amplified products by the physical separation of the single-stranded first strand sequence from the single-stranded second strand sequence prior to amplification;
generating a plurality of single-end sequencing reads of the first set of amplified products;
generating a plurality of single-end sequencing reads of the second set of amplified products; and
comparing at least one single-end sequencing read obtained from the first set of amplified products with at least one single-end sequencing read obtained from the second set of amplified products to generate a consensus sequence of the double-stranded target nucleic acid molecule, wherein a difference between the single-end sequencing reads is considered an artifact.

22. The method of claim 21, wherein the ligating step includes ligating a first double-stranded adapter having a first SMI to a first terminus of the double-stranded target nucleic acid molecule and a second double-stranded adapter having a second SMI to a second terminus of the double-stranded target nucleic acid molecule, and wherein the first SMI differs from the second SMI.

23. The method of claim 22, wherein the first double-stranded adapter has a first primer binding domain and the second double-stranded adapter has a second primer binding domain, and wherein amplifying the first and second strand sequences comprises amplifying the first and second strand sequences through use of primers specific to the first primer binding domain and primers specific to the second primer binding domain.

24. The method of claim 21, wherein the SMI is an exogenous SMI, an endogenous SMI, or a combination thereof.

25. The method of claim 1, wherein the physically separated reaction chambers are selected from containers, tubes, wells, and non-communicating droplets.

26. The method of claim 1, wherein:
step (4) is carried out for each physically separated reaction chamber through use of at least one primer carrying a tag sequence;
the tag sequence is substantially different within each reaction chamber such that the tag sequence operates as a strand defining element (SDE) domain; and
the first and second set of amplified products are recombined prior to steps (7) and (8).

27. The method of claim 3, wherein the non-nucleotide molecule or affinity label is biotin, and wherein the biotin is Biotin-16-Aminoallyl-2'-deoxyuridine-5'-Triphosphate, Biotin-16-Aminoallyl-2'-deoxycytidine-5'-Triphosphate, Biotin-16-Aminoallylcytidine-5'-Triphosphate, N4-Biotin-OBEA-2'-deoxycytidine-5'-Triphosphate, Biotin-16-Aminoallyluridine-5'-Triphosphate, Biotin-16-7-Deaza-7-Aminoallyl-2'-deoxyguanosine-5'-Triphosphate, Desthiobiotin-6-Aminoallyl-2'-deoxycytidine-5'-Triphosphate, 5'-Biotin-G-Monophosphate, 5'-Biotin-A-Monophosphate, 5'-Biotin-dG-Monophosphate, or 5'-Biotin-dA-Monophosphate.

28. The method of claim 3, wherein the non-nucleotide molecule or affinity label is biotin, and wherein the affinity partner is streptavidin attached to a substrate.

29. The method of claim 28, wherein the solid substrate is a solid surface, a bead, or another fixed structure.

30. The method of claim 2, wherein the non-nucleotide molecule or affinity label is located at a terminus of the first strand adapter-target nucleic acid sequence or the second strand adapter-adapter nucleic acid sequence.

31. The method of claim 21, wherein the physically separated reaction chambers are selected from containers, tubes, wells, and non-communicating droplets.

32. The method of claim 21, wherein:
amplification of the first strand sequence and amplification of the second strand sequence is carried out for each physically separated reaction chamber through use of at least one primer carrying a tag sequence;
the tag sequence is substantially different within each reaction chamber such that the tag sequence operates as a strand defining element (SDE) domain; and
the separated first and second sets of amplified products are recombined prior to generating a plurality of single-end sequencing reads for each of the first and second sets of amplified products.

33. The method of claim 21, wherein the double-stranded adapter target nucleic acid molecule comprises a non-nucleotide molecule or affinity label capable of being bound by an affinity partner, the non-nucleotide molecule or affinity label being present on one strand of the double-stranded adapter-target nucleic acid molecule, and wherein physically separating the single-stranded first strand sequence from the single-stranded second strand sequence comprises separating the single-stranded first strand sequence from the single-stranded second strand sequence using the affinity partner to capture the strand comprising the non-nucleotide molecule or affinity label.

34. The method of claim 33, wherein the non-nucleotide molecule or affinity label is selected from the group comprising Colicin E2, Im2, glutathione, glutathione-s-transferase (GST), Nickel, poly-histidine, FLAG-tag, myc-tag, biotin, a small molecule, a nucleic acid, a peptide, and a uniquely bindeable moiety which is capable of being bound by the affinity partner.

35. The method of claim 21, wherein either the first strand sequence or the second strand sequence comprises a physical group having a magnetic property, a charge property, or an insolubility property.

36. The method of claim 35, wherein the physical group has a magnetic property, and wherein physically separating the single-stranded first strand sequence from the single-stranded second strand sequence comprises applying a magnetic field to the single-stranded first and second strand sequences to separate the said strand sequence having the magnetic property from the other strand sequence.

37. The method of claim 35, wherein the physical group has a charge property, and wherein physically separating the single-stranded first strand sequence from the single-stranded second strand sequence comprises applying an electric field to the single-stranded first and second strand sequences to separate the said strand sequence having the charge property from the other strand sequence.

38. The method of claim 35, wherein the physical group has an insolubility property, and wherein physically separating the single-stranded first strand sequence from the single-stranded second strand sequence comprises precipitating the said strand sequence comprising the physical group to separate the single-stranded first and second strand sequences.

39. The method of claim 1, wherein the first strand adapter-target nucleic acid sequence and the second strand adapter-target nucleic acid sequence are differentially labeled prior to the sequencing steps (7) and (8).

40. The method of claim 21, wherein the first strand sequence and the second strand sequence are differentially labeled prior to generating the single-end sequencing reads of the first and second sets of amplified products.

* * * * *

SEQUENCE LISTING

<160> NUMBER OF SEQ ID NOS: 41

<210> SEQ ID NO 1
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 1
ccactacgcc tccgctttcc tctctatggg cagtcggtga t          41

<210> SEQ ID NO 2
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 2
ttggtgatgc ggaggcgaaa ggagagatac ccgtcagcca cta        43

<210> SEQ ID NO 3
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 3
ccatctcatc cctgcgtgtc tccgactcag                              30

<210> SEQ ID NO 4
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 4
ttggtagagt agggacgcac agaggctgag tc                           32

<210> SEQ ID NO 5
<211> LENGTH: 39
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (35)..(38)
<223> OTHER INFORMATION: n is a, c, g, or t

<400> SEQUENCE: 5
ccatctcatc cctgcgtgtc tccgactcag gcgcnnnng                    39

<210> SEQ ID NO 6
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (37)..(40)
<223> OTHER INFORMATION: n is a, c, g, or t

<400> SEQUENCE: 6
ttggtagagt agggacgcac agaggctgag tcatatnnnn c                 41

<210> SEQ ID NO 7
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 7
ccatctcatc cctgcgtgtc tccgactcag aaatgcagc                    39

<210> SEQ ID NO 8
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 8
ttggtagagt agggacgcac agaggctgag tcgggccgtc g                 41

<210> SEQ ID NO 9
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 9
ccatctcatc cctgcgtgtc tccgactcag atatgcagc               39

<210> SEQ ID NO 10
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 10
ttggtagagt agggacgcac agaggctgag tcgcgccgtc g            41

<210> SEQ ID NO 11
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 11
ccatctcatc cctgcgtgtc tccgactcag tattgcagc               39

<210> SEQ ID NO 12
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 12
ttggtagagt agggacgcac agaggctgag tcggcccgtc g            41

<210> SEQ ID NO 13
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 13
ccatctcatc cctgcgtgtc tccgactcag atttgcagc               39

<210> SEQ ID NO 14
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 14
ttggtagagt agggacgcac agaggctgag tccgggcgtc g            41

<210> SEQ ID NO 15
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 15
ccactacgcc tccgctttcc tctctatggg cagtcggtga t            41

<210> SEQ ID NO 16
<211> LENGTH: 43
<212> TYPE: DNA

```
<213> ORGANISM: Artificial Sequence
<220> FEATURE:
<223> OTHER INFORMATION: Synthetic Polynucleotide

<400> SEQUENCE: 16
ttggtgatgc ggaggcgaaa ggagagatac ccgtcagcca cta                    43

<210> SEQ ID NO 17
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 17
ccatctcatc cctgcgtgtc tccgactcag                                   30

<210> SEQ ID NO 18
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 18
ttggtagagt agggacgcac agaggctgag tc                                32

<210> SEQ ID NO 19
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t

<400> SEQUENCE: 19
ccatctcatc cctgcgtgtc tccgactcag nnnnaac                           37

<210> SEQ ID NO 20
<211> LENGTH: 39
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 20
ttggtagagt agggacgcac agaggctgag tcnnnnttg                         39

<210> SEQ ID NO 21
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (38)..(46)
<223> OTHER INFORMATION: n is a, c, g, or t
```

<400> SEQUENCE: 21
ccatctcatc cctgcgtgtc tccgactcag nnnnaacnnn nnnnnn       46

<210> SEQ ID NO 22
<211> LENGTH: 48
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t
<220> FEATURE:
<221> NAME/KEY: misc_feature
<222> LOCATION: (40)..(48)
<223> OTHER INFORMATION: n is a, c, g, or t

<400> SEQUENCE: 22
ttggtagagt agggacgcac agaggctgag tcnnnnttgn nnnnnnn       48

<210> SEQ ID NO 23
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (38)..(46)
<223> OTHER INFORMATION: n is a, c, g, or t

<400> SEQUENCE: 23
ccatctcatc cctgcgtgtc tccgactcag nnnnaacnnn nnnnn       46

<210> SEQ ID NO 24
<211> LENGTH: 48
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t
<220> FEATURE:
<221> NAME/KEY: misc_feature
<222> LOCATION: (40)..(48)
<223> OTHER INFORMATION: n is a, c, g, or t

<400> SEQUENCE: 24
ttggtagagt agggacgcac agaggctgag tcnnnntggn nnnnnnn       48

<210> SEQ ID NO 25
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (38)..(46)

<223> OTHER INFORMATION: n is a, c, g, or t

<400> SEQUENCE: 25
ccatctcatc cctgcgtgtc tccgactcag nnnnaacnnn nnnnnn                46

<210> SEQ ID NO 26
<211> LENGTH: 48
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t
<220> FEATURE:
<221> NAME/KEY: misc_feature
<222> LOCATION: (40)..(48)
<223> OTHER INFORMATION: n is a, c, g, or t

<400> SEQUENCE: 26
ttggtagagt agggacgcac agaggctgag tcnnnntggn nnnnnnn               48

<210> SEQ ID NO 27
<211> LENGTH: 15
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(12)
<223> OTHER INFORMATION: n is a, c, g, or t

<400> SEQUENCE: 27
gctgagtcnn nnttg                                                  15

<210> SEQ ID NO 28
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (38)..(46)
<223> OTHER INFORMATION: n is a, c, g, or t

<400> SEQUENCE: 28
ccatctcatc cctgcgtgtc tccgactcag nnnnaacnnn nnnnnn                46

<210> SEQ ID NO 29
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (38)..(46)
<223> OTHER INFORMATION: n is a, c, g, or t

<400> SEQUENCE: 29
ggtagagtag ggacgcacag aggctgagtc nnnntggnnn nnnnnn        46

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 30
tcagnnnnaa cnnnnnnnnn        20

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 31
tcagnnnnac cnnnnnnnnn        20

<210> SEQ ID NO 32
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, t or u

<400> SEQUENCE: 32
ccatctcatc cctgcgtgtc tccgactcag unnnnc        36

<210> SEQ ID NO 33
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(37)
<223> OTHER INFORMATION: n is a, c, g, or t

<400> SEQUENCE: 33
ttggtagagt agggacgcac agaggctgag tcannnng        38

<210> SEQ ID NO 34
<211> LENGTH: 45
<212> TYPE: DNA

<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, t or u
<220> FEATURE:
<221> NAME/KEY: misc_feature
<222> LOCATION: (37)..(45)
<223> OTHER INFORMATION: n is a, c, g, t or u

<400> SEQUENCE: 34
ccatctcatc cctgcgtgtc tccgactcag unnnncnnnn nnnnn         45

<210> SEQ ID NO 35
<211> LENGTH: 47
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(37)
<223> OTHER INFORMATION: n is a, c, g, or t
<220> FEATURE:
<221> NAME/KEY: misc_feature
<222> LOCATION: (39)..(47)
<223> OTHER INFORMATION: n is a, c, g, or t

<400> SEQUENCE: 35
ttggtagagt agggacgcac agaggctgag tcannnngnn nnnnnnn       47

<210> SEQ ID NO 36
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, t or u
<220> FEATURE:
<221> NAME/KEY: misc_feature
<222> LOCATION: (37)..(45)
<223> OTHER INFORMATION: n is a, c, g, t or u

<400> SEQUENCE: 36
ccatctcatc cctgcgtgtc tccgactcag unnnncnnnn nnnnn         45

<210> SEQ ID NO 37
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, t or u
<220> FEATURE:
<221> NAME/KEY: misc_feature
<222> LOCATION: (37)..(45)
<223> OTHER INFORMATION: n is a, c, g, t or u

<400> SEQUENCE: 37
ggtagagtag ggacgcacag aggctgagtc annnngnnnn nnnnn         45

<210> SEQ ID NO 38
<211> LENGTH: 44

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (36)..(44)
<223> OTHER INFORMATION: n is a, c, g, or t

<400> SEQUENCE: 38
ccatctcatc cctgcgtgtc tccgactcag nnnncnnnnn nnnn            44

<210> SEQ ID NO 39
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, or t
<220> FEATURE:
<221> NAME/KEY: misc_feature
<222> LOCATION: (37)..(45)
<223> OTHER INFORMATION: n is a, c, g, or t

<400> SEQUENCE: 39
ggtagagtag ggacgcacag aggctgagtc annnngnnnn nnnnn           45

<210> SEQ ID NO 40
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, or t
<220> FEATURE:
<221> NAME/KEY: misc_feature
<222> LOCATION: (37)..(45)
<223> OTHER INFORMATION: n is a, c, g, or t

<400> SEQUENCE: 40
ccatctcatc cctgcgtgtc tccgactcag gnnnncnnnn nnnnn           45

<210> SEQ ID NO 41
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(35)
<223> OTHER INFORMATION: n is a, c, g, or t
<220> FEATURE:
<221> NAME/KEY: misc_feature
<222> LOCATION: (37)..(45)
<223> OTHER INFORMATION: n is a, c, g, or t

<400> SEQUENCE: 41
ggtagagtag ggacgcacag aggctgagtc annnngnnnn nnnnn           45
```